(12) United States Patent
Lin et al.

(10) Patent No.: US 7,183,413 B2
(45) Date of Patent: Feb. 27, 2007

(54) AMINOQUINOLINE COMPOUNDS

(75) Inventors: Chu-Chung Lin, Taichung (TW);
Jen-Fuh Liu, Taipei (TW); Chih-Wei Chang, Taipei (TW); Shu-Jen Chen, Taipei (TW); Yibin Xiang, Acton, MA (US); Pei-Chin Cheng, Changhun County (TW); Jiing-Jyh Jan, Taipei County (TW)

(73) Assignee: Taigen Biotechnology, Taipei (TW)

( * ) Notice: Subject to any disclaimer, the term of this patent is extended or adjusted under 35 U.S.C. 154(b) by 30 days.

(21) Appl. No.: 10/819,646

(22) Filed: Apr. 6, 2004

(65) Prior Publication Data

US 2004/0209902 A1  Oct. 21, 2004

Related U.S. Application Data

(60) Provisional application No. 60/551,750, filed on Mar. 9, 2004, provisional application No. 60/462,495, filed on Apr. 11, 2003.

(51) Int. Cl.
*C07D 215/16* (2006.01)
*C07D 215/38* (2006.01)

(52) U.S. Cl. ............... 546/157; 546/162; 514/312; 514/313; 514/314

(58) Field of Classification Search ............... 514/312, 514/313, 314; 546/157, 162
See application file for complete search history.

(56) References Cited

U.S. PATENT DOCUMENTS

| 5,756,517 | A | 5/1998 | Schohe-Loop et al. | 514/314 |
| 5,866,562 | A | 2/1999 | Schohe-Loop et al. | 514/183 |
| 6,174,897 | B1 | 1/2001 | Schohe-Loop et al. | 514/312 |
| 6,194,403 | B1 | 2/2001 | Hu et al. | 514/213.01 |
| 6,221,882 | B1 * | 4/2001 | Macfarlane | 514/313 |
| 6,399,630 | B1 * | 6/2002 | Macfarlane | 514/313 |
| 6,479,504 | B1 * | 11/2002 | Macfarlane et al. | 514/297 |
| 6,521,637 | B2 * | 2/2003 | Macfarlane | 514/313 |

FOREIGN PATENT DOCUMENTS

| WO | WO 95/23137 | 8/1995 |
| WO | WO 97/21681 | 6/1997 |
| WO | WO 98/55125 | 12/1998 |
| WO | 2000/76982 | * 12/2000 |
| WO | WO 2002/083143 | * 10/2002 |

OTHER PUBLICATIONS

Carlier et al., "Heterodimeric Tacrine-Based Acetylcholinesterase Inhibitors: Investigating Ligand-Peripheral Site Interactions", J. Med. Chem. 42:4225-4231, 1999.
Hu et al., "Homodimeric Tacrine Congeners as Acetylcholinesterase Inhibitors", J. Med. Chem. 45:2277-2282, 2002.
Srivastava et al., "Synthesis of Bisquinolines and their In Vitro bility to Produce Methemoglobin In Canine Hemolysate", Bioorganic & Medicinal Chemistry Letters 9:653-658, 1999.

* cited by examiner

*Primary Examiner*—D. Margaret Seaman
(74) *Attorney, Agent, or Firm*—Fish & Richardson P.C.

(57) ABSTRACT

This invention relates to treating inflammatory and immune diseases with certain aminoquinoline compounds that bind to CXCR3 receptors. The aminoquinoline compounds are covered by the formula (I) shown below. Each variable is defined in the specification.

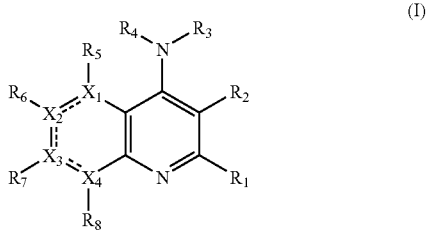

(I)

46 Claims, No Drawings

AMINOQUINOLINE COMPOUNDS

CROSS REFERENCE TO RELATED APPLICATIONS

Pursuant to 35 USC § 119(e), this application claims priority to U.S. Provisional Application Ser. No. 60/462,495, filed Apr. 11, 2003, and U.S. Provisional Application Ser. No. 60/551,750, filed Mar. 9, 2004, the contents of which are incorporated herein by reference.

BACKGROUND

Chemokines have been classified into four groups according to their structures. CXC and CC chemokines, the two large groups, feature the presence and absence of an amino acid, respectively, between the first two cysteine residues in a conserved four-cysteine motif (Mackay C. R., Nat. Immunol., (2001) 2:95; Olson et al., Am. J. Physiol. Regul. Integr. Comp. Physiol., (2002) 283:R7). CXCR3 is the first chemokine receptor found to be highly induced by T cell activation (Loetscher et al., J. Exp. Med., (1996) 184:963). CXCR3 is expressed on some circulating blood T cells, B cells, and natural killer cells (Qin et al., J. Clin. Invest., (1998) 101:746). For example, expression of CXCR3 is induced virtually by all T cells in synovial fluid of rheumatoid arthritis and in various inflamed tissues (e.g., ulcerative colitis, chronic vaginitis, and sarcoidosis), particularly in perivascular regions. However, few T cells in normal lymph nodes are induced to express CXCR3 (Agostini et al., J. Immunol., (1998) 161:6413). Expression and responsiveness of CXCR3 can be markedly increased by T cell activation (Rabin et al., J. Immunol., (1999) 162:3840). CXCR3 is also consistently detected in functional forms on transformed B cells obtained from chronic lymphocytic leukemia patients (Trentin et al., J. Clin. Invest., (1999) 104:115).

CXCR3 binds to three highly potent, inflammation-inducible, ELR-negative CXC chemokines, i.e., I-TAC, Mig, and IP-10. These three chemokines chemoattract and induce calcium influx in activated T cells, tumor-infiltrating lymphocytes, and CXCR3-transfected cells (Loetscher et al., Eur. J. Immunol., (1998) 28:3696; Cole et al., J. Exp. Med., (1998) 187:2009; Weng et al., J. Biol. Chem., (1998) 273: 18288). CXCR3 signaling appears to be an important mechanism for selective homing of activated/effector cells, which are known to accumulate preferentially at inflammatory sites and in many tumors. For example, IP-10 is expressed abundantly at various inflammatory sites, particularly those characterized by T cell infiltration, such as in tissues affected by delayed type hypersensitivity responses, experimental autoimmune encephalomyelitis, or a transplant undergoing rejection (Qin et al., J. Clin. Invest., (1998) 101:746). CXCR3 ligand-induced recruitment of leukocytes is thought to be an essential step in the pathogenesis of tissue-specific autoimmune inflammatory diseases, as well as in graft rejection (Hancock et al., J. Exp. Med., (2000) 192:1515).

SUMMARY

This invention is based on the discovery that certain aminoquinoline compounds are effective in treating inflammatory and immune diseases through their binding to CXCR3 receptors.

In one aspect, this invention features aminoquinoline compounds of formula (I) or their salts:

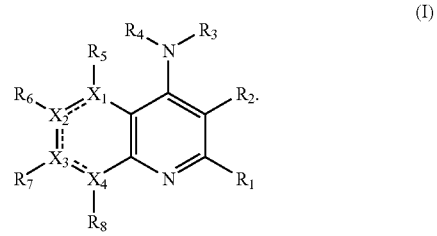

(I)

In this formula, each ==== is a single bond or a double bond; provided that if one ==== is a double bond, its neighboring ==== is not a double bond; each of ====$X_1$—, ====$X_2$—, ====$X_3$—, and ====$X_4$—, independently, is —C=, —$CR_a$—, —N=, —N—, —S—, —O—, or a single bond; at most one of ====$X_1$—, ====$X_2$—, ====$X_3$—, and ====$X_4$— being a single bond, and at most two of ====$X_1$—, ====$X_2$—, ====$X_3$—, and ====$X_4$— being —N=, —N—, —S—, or —O—; each of $R_1$ and $R_2$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $C_1$–$C_6$ alkylamino, $C_1$–$C_{12}$ dialkylamino, arylamino, diarylamino, —C(O)—$NR_bR_b'$, —C(O)—$OR_b$, —OC(O)—$R_b$, —C(O)—$R_b$, or halogen; or $R_1$ and $R_2$ together are $C_5$–$C_8$ heterocycloalkyl; each of $R_3$ and $R_4$, independently, is H or -A-N(B)-D; and each of $R_5$, $R_6$, $R_7$, and $R_8$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $NO_2$, CN, $C_1$–$C_6$ alkylamino, $C_1$–$C_{12}$ dialkylamino, arylamino, diarylamino, —C(O)—$NR_cR_c'$, —C(O)—$OR_c$, —OC(O)—$R_c$, —C(O)—$R_c$, halogen, or deleted; or $R_5$ and $R_6$ together are $C_5$–$C_7$ cycloalkyl or $C_5$–$C_7$ heterocycloalkyl; or $R_6$ and $R_7$ together are $C_5$–$C_7$ cycloalkyl or $C_5$–$C_7$ heterocycloalkyl; or $R_7$ and $R_8$ together are $C_5$–$C_7$ cycloalkyl or $C_5$–$C_7$ heterocycloalkyl; provided that if $R_5$ is deleted, ====$X_1$— is —N=, —S—, —O—, or a single bond; if $R_6$ is deleted, ====$X_2$— is —N=, —S—, —O—, or a single bond; if $R_7$ is deleted, ====$X_3$— is —N=, —S—, —O—, or a single bond; and if $R_8$ is deleted, ====$X_4$— is —N=, —S—, —O—, or a single bond. A is $C_1$–$C_{12}$ alkyl optionally containing 1–6 heteroatoms, $C_2$–$C_{12}$ alkenyl optionally containing 1–6 heteroatoms, $C_2$–$C_{12}$ alkynyl optionally containing 1–6 heteroatoms, aryl, heteroaryl, $C_1$–$C_{10}$ alkylsulfonyl, arylsulfonyl, $C_1$–$C_{10}$ alkylcarbonyl containing 1–6 heteroatoms, $C_2$–$C_{20}$ alkylaryl optionally containing 1–6 heteroatoms, $C_2$–$C_{20}$ arylalkyl optionally containing 1–6 heteroatoms, $C_2$–$C_{20}$ alkylheteroaryl containing 1–6 heteroatoms, or $C_2$–$C_{20}$ heteroarylalkyl containing 1–6 heteroatoms. B is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, or heteroaryl; or B and A together are heteroaryl. D is H, aryl, heteroaryl, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, —C(O)—$R_d$, —$SO_2$—$R_d$, —C(S)—$R_d$, —C(O)—$NR_dR_d'$, —C(O)—$OR_d$, —OC(O)—$R_d$, —C(O)—$SR_d$, or —SC(O)—$R_d$; or D and A together are heteroaryl. Each of $R_a$, $R_b$, $R_b'$, $R_c$, $R_c'$, $R_d$, and $R_d'$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, or heteroaryl; or $R_d$ and $R_d'$ together being $C_5$–$C_7$ heterocycloalkyl.

Referring to formula (I), a subset of the compounds described above are those in which D is of formula (II):

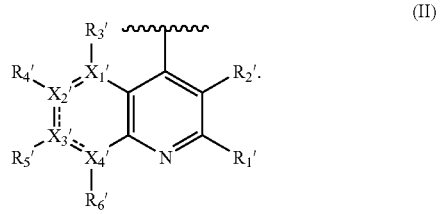

(II)

In formula (II), each ═══ is a single bond or a double bond; provided that if one ═══ is a double bond, its neighboring ═══ is not a double bond; each of ═══$X_1'$—, ═══$X_2'$—, ═══$X_3'$—, and ═══$X_4'$—, independently, is —C═, —$CR_e$—, —N═, —N—, —S—, —O—, or a single bond; at most one of ═══$X_1'$—, ═══$X_2'$—, ═══$X_3'$—, and ═══$X_4'$—, being a single bond, and at most two of ═══$X_1'$—, ═══$X_2'$—, ═══$X_3'$—, and ═══$X_4'$—, being —N═, —N—, —S—, or —O—; each of $R_1'$ and $R_2'$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $C_1$–$C_6$ alkylamino, $C_1$–$C_{12}$ dialkylamino, arylamino, diarylamino, —C(O)—$NR_fR_f'$, —C(O)—$OR_f$, —OC(O)—$R_f$, —C(O)—$R_f$, or halogen; or $R_1'$ and $R_2'$ together are $C_5$–$C_8$ cycloalkyl or $C_5$–$C_8$ heterocycloalkyl; each of $R_3'$, $R_4'$, $R_5'$, and $R_6'$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $NO_2$, CN, $C_1$–$C_6$ alkylamino, $C_1$–$C_{12}$ dialkylamino, arylamino, diarylamino, —C(O)—$NR_gR_g'$, —C(O)—$OR_g$, —OC(O)—$R_g$, —C(O)—$R_g$, halogen, or deleted; or $R_3'$ and $R_4'$ together are $C_5$–$C_7$ cycloalkyl or $C_5$–$C_7$ heterocycloalkyl; or $R_4'$ and $R_5'$ together are $C_5$–$C_7$ cycloalkyl or $C_5$–$C_7$ heterocycloalkyl; or $R_5'$ and $R_6'$ together are $C_5$–$C_7$ cycloalkyl or $C_5$–$C_7$ heterocycloalkyl; provided that if $R_3'$ is deleted, ═══$X_1'$— is —N═, —S—, —O—, or a single bond; if $R_4'$ is deleted, ═══$X_2'$— is —N═, —S—, —O—, or a single bond; if $R_5'$ is deleted, ═══$X_3'$— is —N═, —S—, —O—, or a single bond; and if $R_6'$ is deleted, ═══$X_4'$— is —N═, —S—, —O—, or a single bond. Each of $R_e$, $R_f$, $R_f'$, $R_g$, and $R_g'$, independently, being H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, or heteroaryl. Referring to formula (I), another subset of the compounds described above are those in which A is $C_1$–$C_{12}$ alkyl; $C_1$–$C_{12}$ alkyl containing 1–6 heteroatoms and optionally substituted with sulfonyl, $C_1$–$C_6$ alkylsulfonyl, arylsulfonyl, or heteroarylsulfonyl; $C_2$–$C_{20}$ alkylaryl optionally containing 1–6 heteroatoms; or aryl; or A and B together are heteroaryl.

The term "alkyl" refers to a saturated, linear or branched hydrocarbon moiety, such as —$CH_3$, —$CH_2$—, or branched —$C_3H_7$. The term "alkenyl" refers to a linear or branched, non-aromatic hydrocarbon moiety having at least one double bond, such as —CH═$CH_2$ or —CH═CH—. The term "alkynyl" refers to a linear or branched, non-aromatic hydrocarbon moiety having at least one triple bond, such as —C≡CH or —C≡C—. The term "cycloalkyl" refers to a saturated cyclic hydrocarbon moiety, such as cyclohexyl. The term "cycloalkenyl" refers to a non-aromatic cyclic hydrocarbon moiety having at least one double bond in the ring, such as 2-cyclopentenyl. The term "heterocycloalkyl" refers to a saturated non-aromatic cyclic moiety having at least one ring heteroatom (e.g., O, N, and S), such as 4-tetrahydropyranyl. The term "heterocycloalkenyl" refers to a non-aromatic cyclic moiety having at least one ring heteroatom and at least one double bond in the ring, such as 3,4-dihydropyran-4-yl. The term "alkoxy" refers to a linear or branched, saturated or unsaturated, non-aromatic hydrocarbon moiety containing an oxygen radical, such as —$OCH_3$ or —OCH═$C_2H_5$. The term "aryloxy" refers to a moiety having at least one aromatic ring and an oxygen radical bonded to the aromatic ring, such as phenoxy. The term "heteroaryloxy" refers to a moiety having at least one aromatic ring that contains at least one ring heteroatom and an oxygen radical bonded to the aromatic ring, such as 4-pyrindinoxy. The term "aryl" refers to a hydrocarbon moiety having one or more aromatic rings. Examples of an aryl moiety include phenyl, phenylene, naphthyl, naphthylene, pyrenyl, anthryl, and phenanthryl. The term "heteroaryl" refers to a moiety having one or more aromatic rings that contain at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "alkylaryl" refers to an aryl moiety substituted with unsubstituted or substituted alkyl, such as

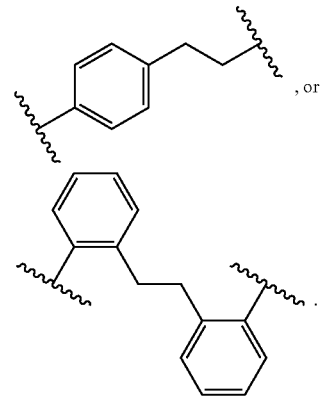

, or

The term "alkylheteroaryl" refers to a heteroaryl moiety substituted with unsubstituted or substituted alkyl. The terms "arylalkyl" and "heteroarylalkyl" respectively refer to an alkyl moiety substituted with unsubstituted or substituted aryl and an alkyl moiety substituted with unsubstituted or substituted heteroaryl, such as benzyl or pyridinylmethyl. Alkylaryl and arylalkyl may optionally contain 1–6 heteroatoms. Alkylheteroaryl and heteroarylalkyl contain 1–6 heteroatoms.

Alkyl, alkenyl, alkynyl, cycloalkyl, cycloalkenyl, heterocycloalkyl, heterocycloalkenyl, alkoxy, aryloxy, heteroaryloxy, aryl, and heteroaryl mentioned herein include both substituted and unsubstituted moieties. Examples of substituents for cycloalkyl, cycloalkenyl, heterocycloalkyl, heterocycloalkenyl, aryloxy, heteroaryloxy, aryl, and heteroaryl include $C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_1$–$C_{10}$ alkoxy, aryl, aryloxy, heteroaryl, heteroaryloxy, $C_1$–$C_{10}$ alkylsulfonyl, arylsulfonyl, heteroarylsulfonyl, amino, $C_1$–$C_{10}$ alkylaamino, $C_1$–$C_{20}$ dialkylamino, arylamino, diarylamino, $C_1$–$C_{10}$ alkylimino, arylimino, amido, carbamoyl, thioamido, thiocarbamoyl, hydroxyl, halogen, thio, $C_1$–$C_{10}$ alkylthio, arylthio, cyano, nitro, acyl, acyloxy, carboxyl, and carboxylic ester. Examples of substituents for alkyl, alkenyl, alkynyl, and alkoxy include all of the above substitutents except $C_1$–$C_{10}$ alkyl, $C_2$–$C_{10}$ alkenyl, and $C_2$–$C_{10}$ alkynyl. Cycloalkyl, cycloalkenyl, heterocycloalkyl heterocycloalkenyl, aryl, and heteroaryl also include fused groups.

In another aspect, this invention features aminoquinoline compounds of formula (I) shown above except that each of $R_1$ and $R_2$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $C_1$–$C_6$ alkylamino, $C_1$–$C_{12}$ dialkylamino, arylamino, diarylamino, —C(O)—$NR_bR_b'$, —OC(O)—$R_b$, —C(O)—$R_b$, or halogen; or $R_1$ and $R_2$ together are $C_5$–$C_8$ cycloalkyl or $C_5$–$C_8$ heterocycloalkyl; each of $R_5$, $R_6$, $R_7$, and $R_8$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $NO_2$, CN, $C_1$–$C_6$ alkylamino, $C_1$–$C_{12}$ dialkylamino, arylamino, diarylamino, —C(O)—$NR_cR_c'$, —C(O)—$OR_c$, —OC(O)—$R_c$, —C(O)—$R_c$, or deleted; or $R_5$ and $R_6$ together are $C_5$–$C_7$ cycloalkyl or $C_5$–$C_7$ heterocycloalkyl; or $R_6$ and $R_7$ together are $C_5$–$C_7$ cycloalkyl or $C_5$–$C_7$ heterocycloalkyl; or $R_7$ and $R_8$ together are $C_5$–$C_7$ cycloalkyl or $C_5$–$C_7$ heterocycloalkyl; provided that if $R_5$ is deleted, ====$X_1$— is —N=, —S—, —O—, or a single bond; if $R_6$ is deleted, ====$X_2$— is —N=, —S—, —O—, or a single bond; if $R_7$ is deleted, ====$X_3$— is —N=, —S—, —O—, or a single bond; and if $R_8$ is deleted, ====$X_4$— is —N=, —S—, —O—, or a single bond; and further provided that not all of $R_5$, $R_6$, $R_7$, and $R_8$ are H;

In still another aspect, this invention features a method for treating an inflammatory or immune disease. The method includes administering to a subject in need of treatment of an effective amount of one or more compounds of formula (I) shown above except that each of $R_1$ and $R_2$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $C_1$–$C_6$ alkylamino, $C_1$–$C_{12}$ dialkylamino, arylamino, diarylamino, —C(O)—$NR_bR_b'$, —C(O)—$OR_b$, —OC(O)—$R_b$, —C(O)—$R_b$, or halogen; or $R_1$ and $R_2$ together are $C_5$–$C_8$ cycloalkyl or $C_5$–$C_8$ heterocycloalkyl; each of $R_5$, $R_6$, $R_7$, and $R_8$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $NO_2$, CN, $C_1$–$C_6$ alkylamino, $C_1$–$C_{12}$ dialkylamino, arylamino, diarylamino, —C(O)—$NR_cR_c'$, —C(O)—$OR_c$, —OC(O)—$R_c$, —C(O)—$R_c$, halogen, or deleted; or $R_5$ and $R_6$ together are $C_5$–$C_7$ cycloalkyl or $C_5$–$C_7$ heterocycloalkyl; or $R_6$ and $R_7$ together are $C_5$–$C_7$ cycloalkyl or $C_5$–$C_7$ heterocycloalkyl; or $R_7$ and $R_8$ together are $C_5$–$C_7$ cycloalkyl or $C_5$–$C_7$ heterocycloalkyl; provided that if $R_5$ is deleted, ====$X_1$— is —N=, —S—, —O—, or a single bond; if $R_6$ is deleted, ====$X_2$— is —N=, —S—, —O—, or a single bond; if $R_7$ is deleted, ====$X_3$— is —N=, —S—, —O—, or a single bond; and if $R_8$ is deleted, ====$X_4$— is —N=, —S—, —O—, or a single bond; in which B is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, or heteroaryl; or B and A together are $C_5$–$C_7$ heterocycloalkyl or heteroaryl; and D is H, aryl, heteroaryl, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, —C(O)—$R_d$, —$SO_2$—$R_d$, —C(S)—$R_d$, —C(O)—$NR_dR_d'$, —C(O)—$OR_d$, —OC(O)—$R_d$, —C(O)—$SR_d$, or —SC(O)—$R_d$; or D and A together are $C_5$–$C_7$ heterocycloalkyl or heteroaryl.

"Treatment" refers to administering one or more aminoquinoline compounds to a subject, who has an inflammatory or immune disease, a symptom of such a disease, or a predisposition toward such a disease, with the purpose to confer a therapeutic effect, e.g., to cure, relieve, alter, affect, ameliorate, or prevent the inflammatory or immune disease, the symptom of it, or the predisposition toward it. "An effective amount" refers to the amount of one or more active aminoquinoline compounds that is required to confer a therapeutic effect on a treated subject.

An inflammatory disease is characterized by a local or systemic, acute or chronic inflammation. An immune disease is characterized by a hyper- or hypo-reaction of the immune system. Examples of inflammatory or immune diseases include multiple sclerosis, systemic lupus erythematosus, rheumatoid arthritis, atherosclerosis, encephalitis, meningitis, hepatitis, nephritis, sepsis, sarcoidosis, psoriasis, eczema, uticaria, Type I diabetes, asthma, conjunctivitis, otitis, allergic rhinitis, chronic obstructive pulmonary disease, sinusitis, dermatitis, inflammatory bowel disease, ulcerative colitis, Crohn's disease, Behcet's syndrome, gout, cancer, viral infections, bacterial infections, organ transplant conditions, skin transplant conditions, graft rejection (including allograft rejection and graft-versus-host disease), spondyloarthropathies, scleroderma, vasculitis, and psoriasis (including T-cell mediated psoriasis).

A subject in need of treatment of an inflammatory or immune disease can also be concurrently administered with an aminoquinoline compound described above and one or more other therapeutic agents at the same time or at different times during the period of treatment. Examples of such a therapeutic agent include a steroidal or a non-steroidal anti-inflammatory drug, a COX2 inhibitor, a leukotriene receptor inhibitor, a prostaglandin modulator, a TNF modulator, and an immunosuppressive agent (e.g., cyclosporine A).

In a further aspect, this invention features a pharmaceutical composition that contains an effective amount of at least one of the above-mentioned aminoquinoline compounds and a pharmaceutically acceptable carrier.

The aminoquinoline compounds described above include the compounds themselves, as well as their salts and their prodrugs, if applicable. A salt, for example, can be formed between an anion and a positively charged group (e.g., amino) on an aminoquinoline compound. Suitable anions include chloride, bromide, iodide, sulfate, bisulfate, sulfamate, nitrate, phosphate, citrate, methanesulfonate, trifluoroacetate, maleate, succinate, fumarate, tartrate, salicylate, lactate, naphthalenesulfonate, and acetate. Likewise, a salt can also be formed between a cation and a negatively charged group (e.g., carboxylate) on an aminoquinoline compound. Suitable cations include sodium ion, potassium ion, magnesium ion, calcium ion, and an ammonium cation such as tetramethylammonium ion. The aminoquinoline compounds also include those salts containing quaternary nitrogen atoms. Examples of prodrugs include esters and other pharmaceutically acceptable derivatives, which, upon administration to a subject, are capable of providing active aminoquinoline compounds.

Also within the scope of this invention is a composition containing one or more of the aminoquinoline compounds described above for use in treating an inflammatory disease or an immune disease, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are exemplary compounds, compounds 1–190, of this invention.

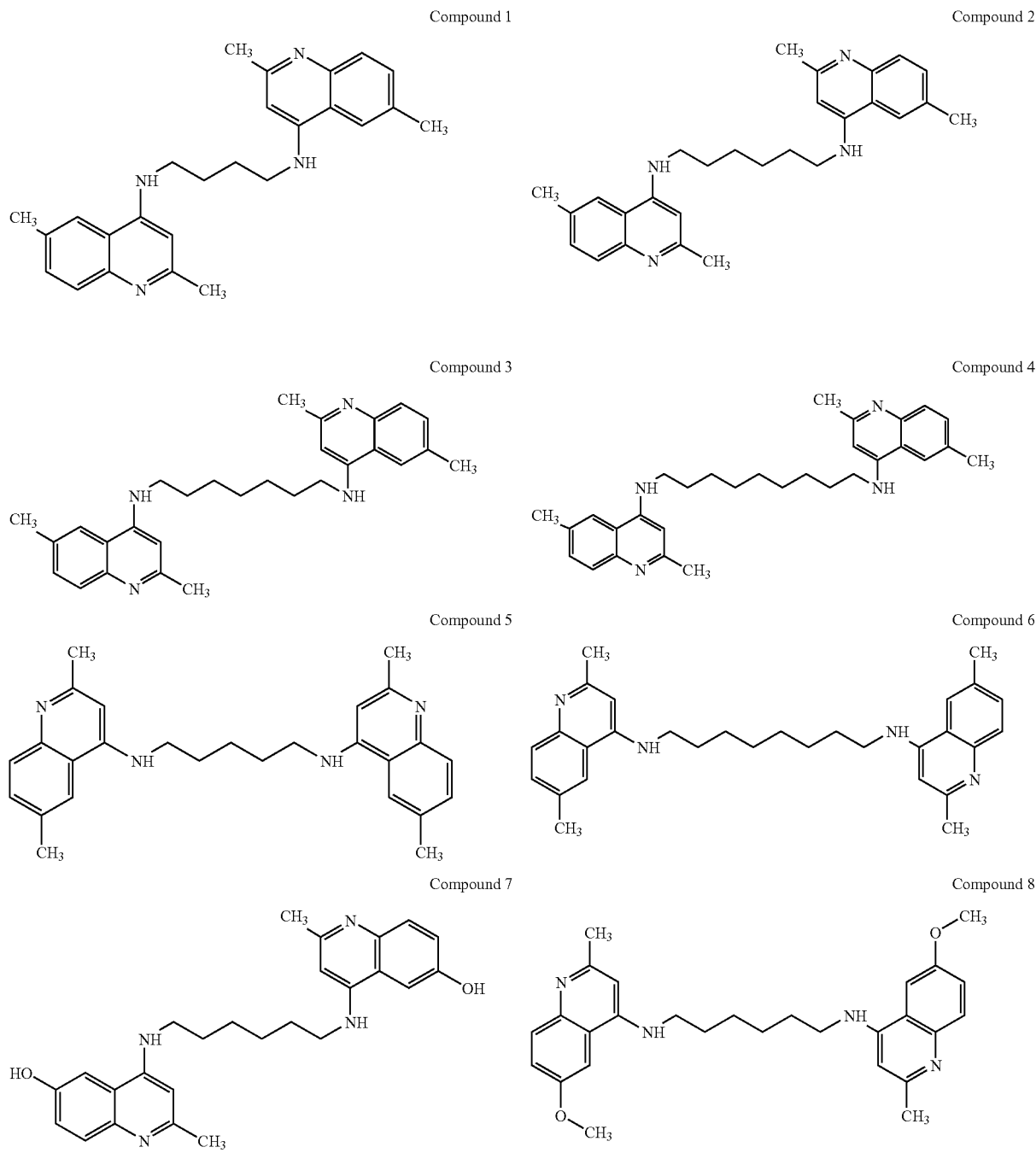

-continued
Compound 9
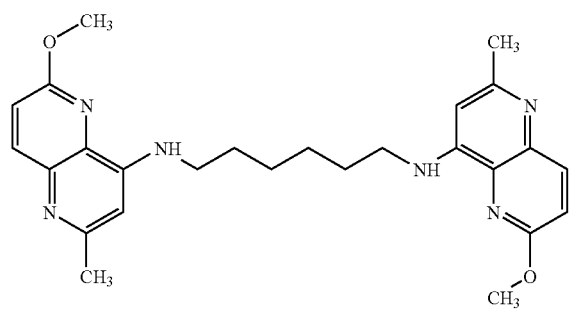
Compound 10
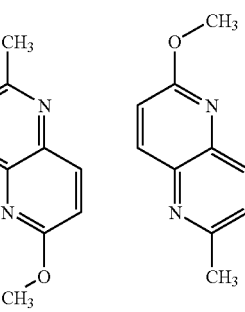
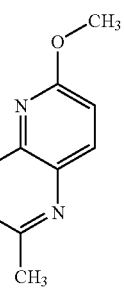
Compound 11
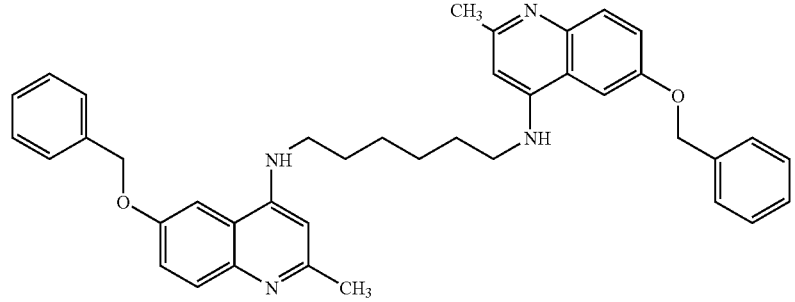
Compound 12
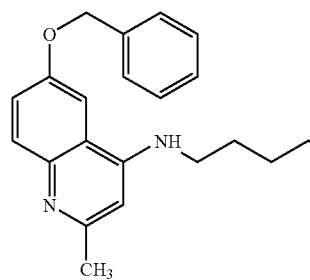
Compound 13
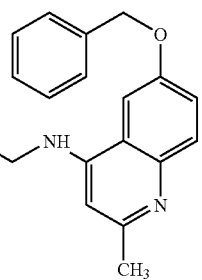
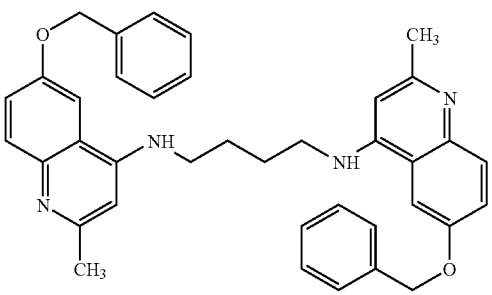
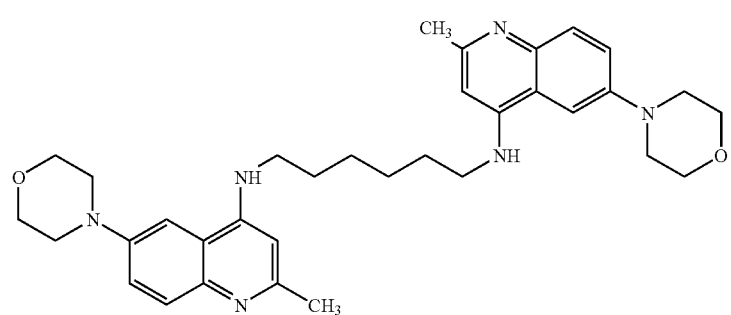
Compound 15
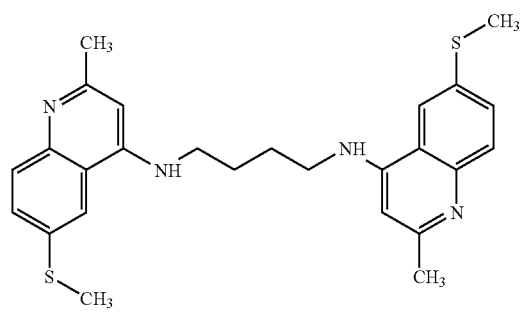
Compound 16
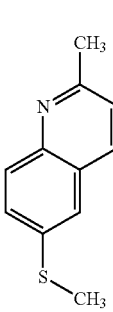
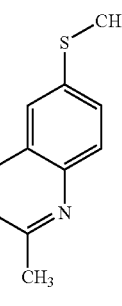

-continued
Compound 17
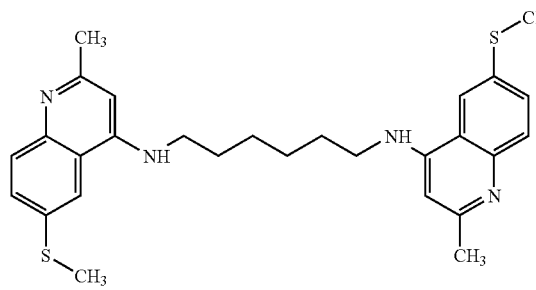
Compound 18
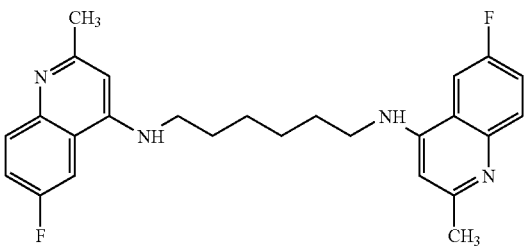
Compound 19
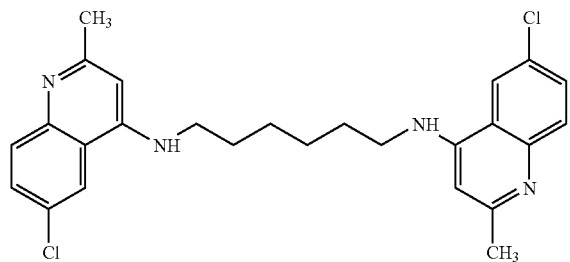
Compound 20
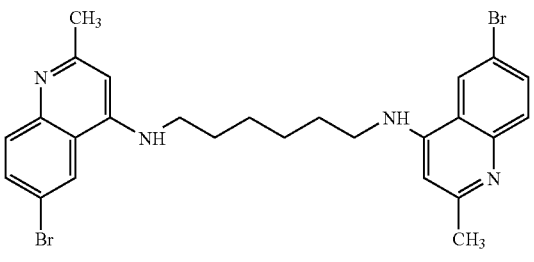
Compound 21
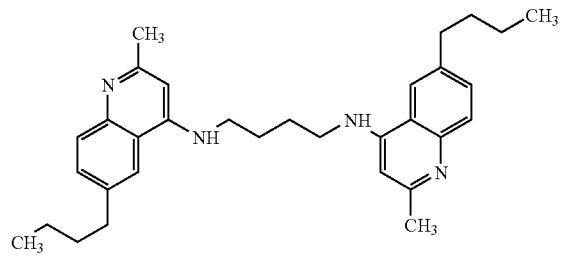
Compound 22
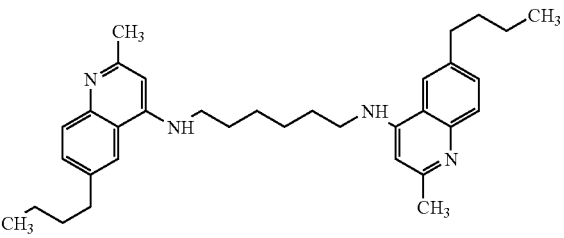
Compound 23
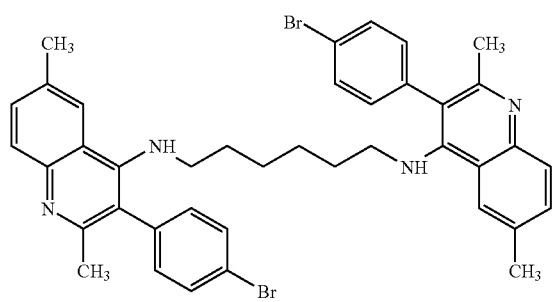
Compound 24
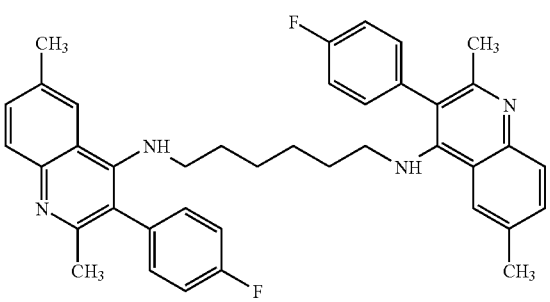
Compound 25
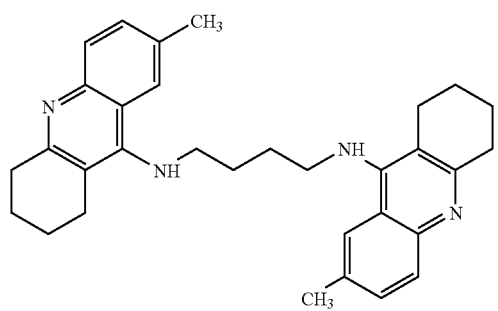
Compound 26
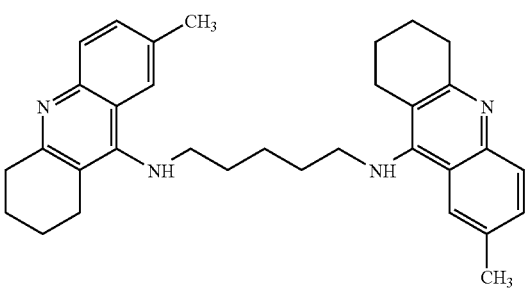

-continued
Compound 27
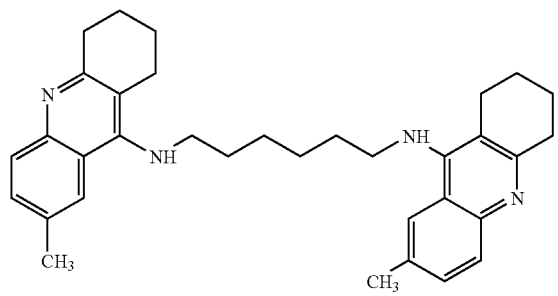
Compound 28
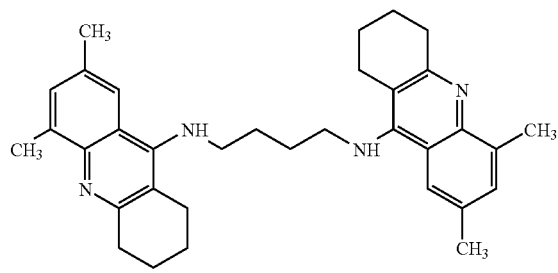
Compound 29
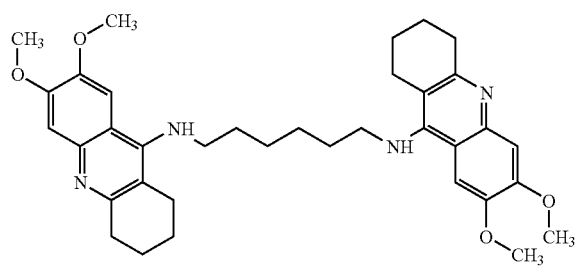
Compound 30
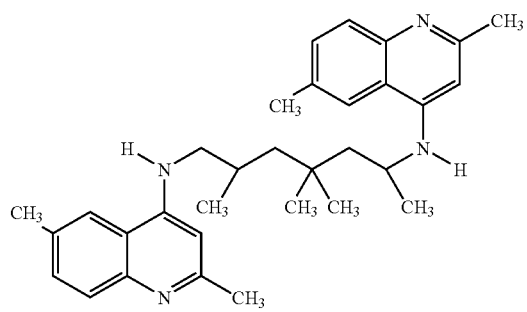
Compound 31
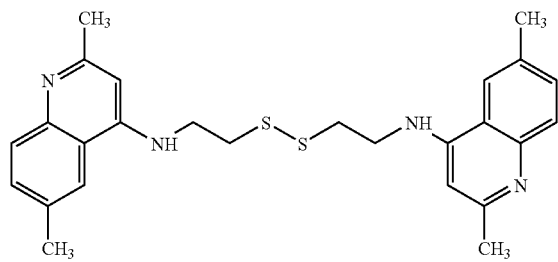
Compound 32
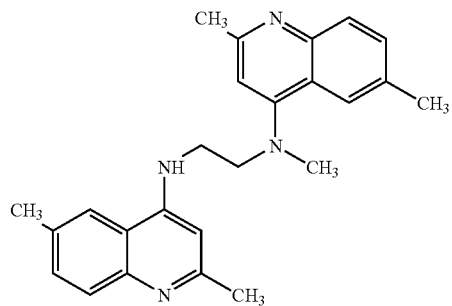
Compound 33
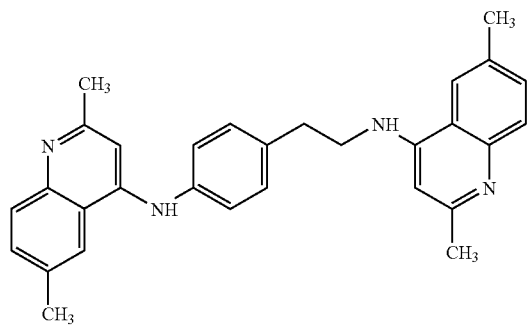
Compound 34
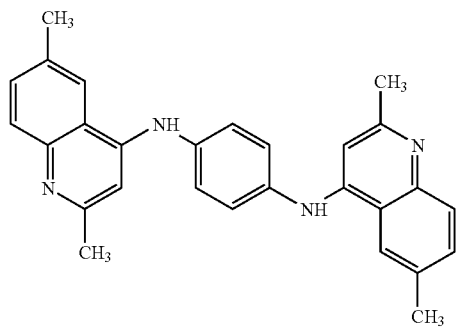

-continued
Compound 35
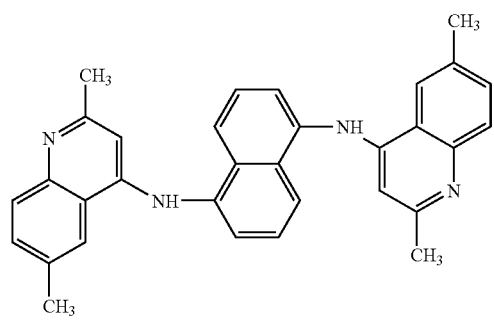
Compound 36
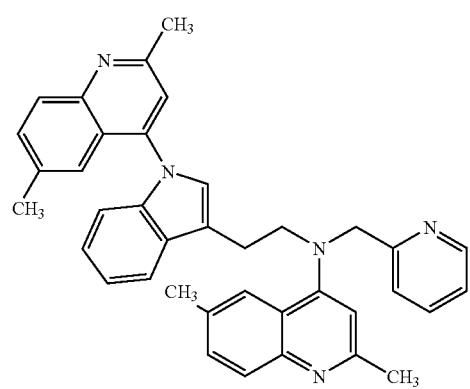 (at left column position shifted)
Compound 37
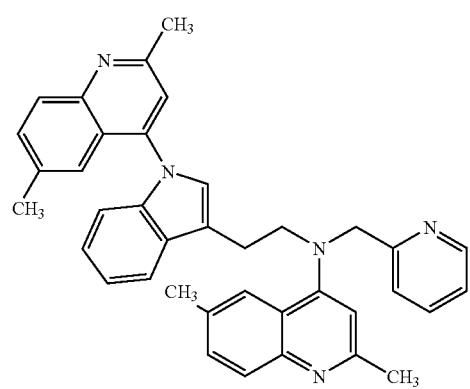
Compound 38
Compound 39
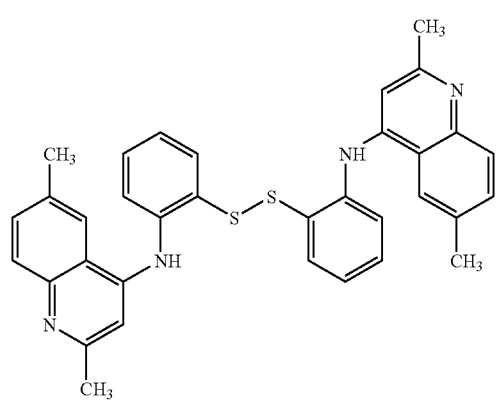
Compound 40
Compound 41
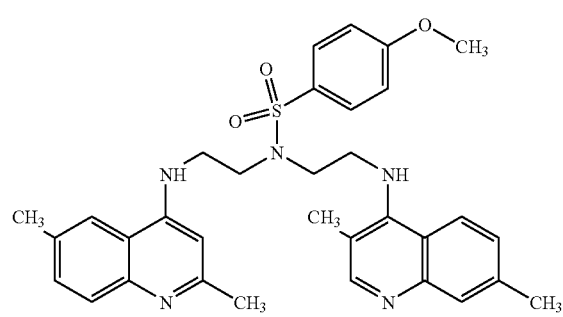
Compound 42
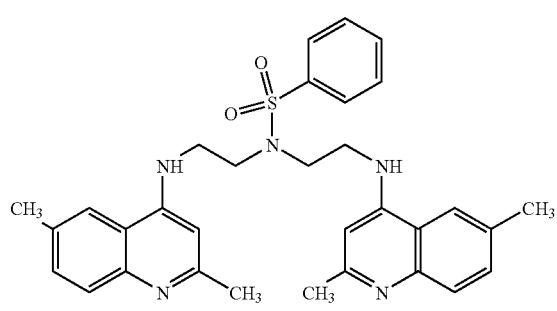

-continued
Compound 43
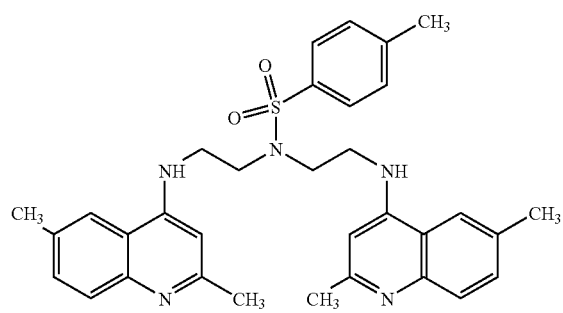
Compound 44
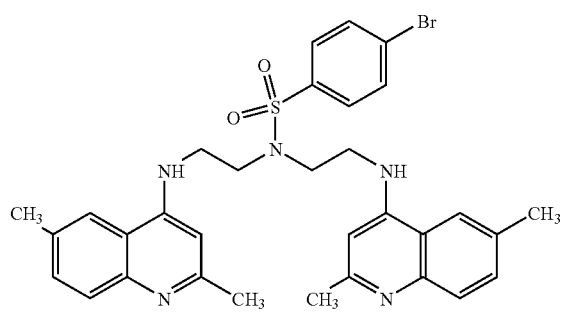
Compound 45
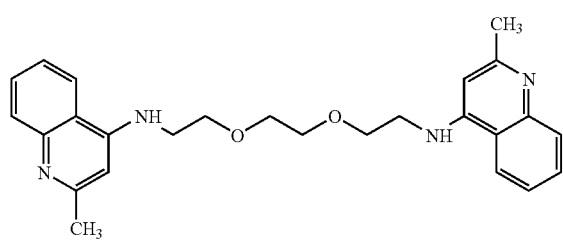
Compound 46
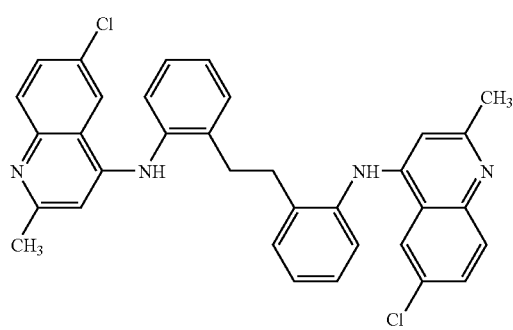
Compound 47
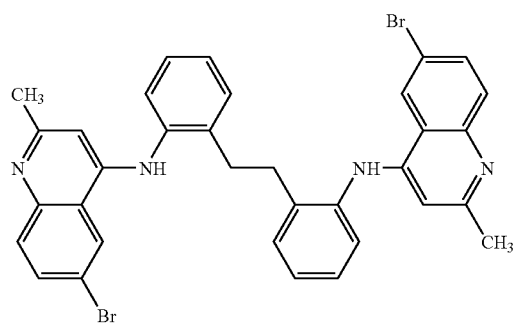
Compound 48
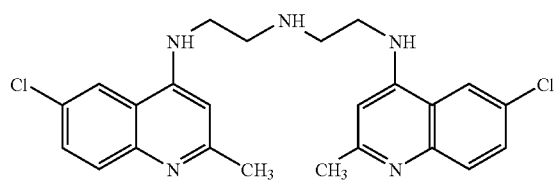
Compound 49
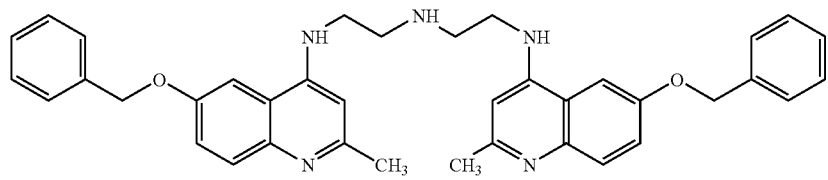
Compound 50
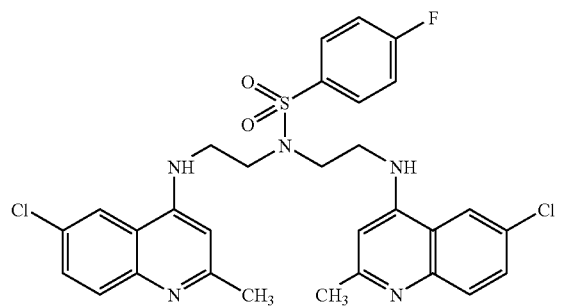
Compound 51
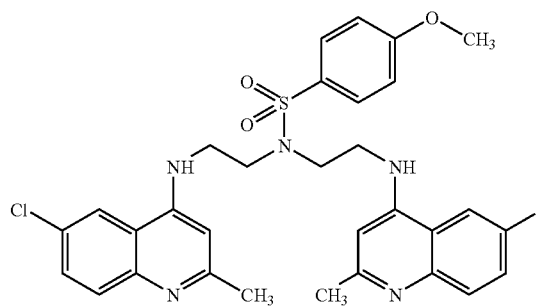

-continued
Compound 52
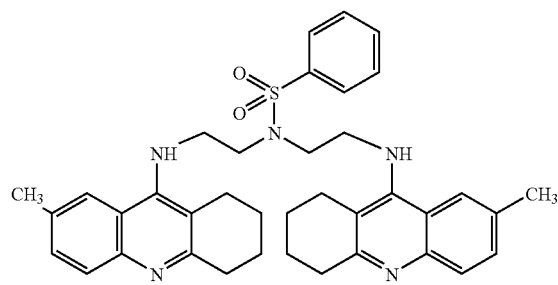
Compound 53
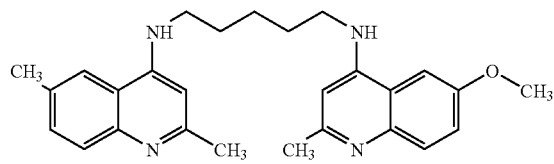
Compound 54
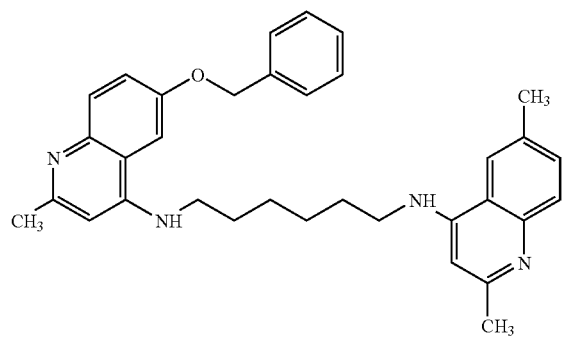
Compound 55
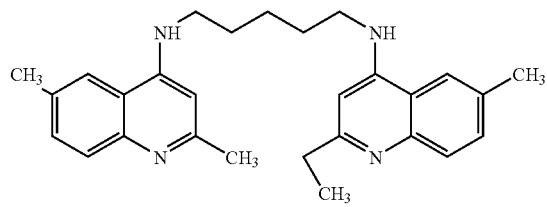
Compound 56
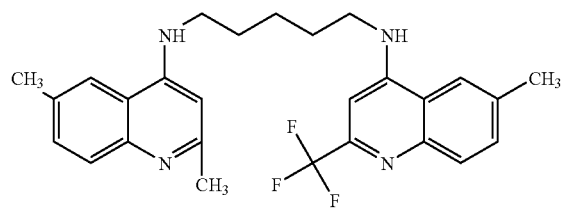
Compound 57
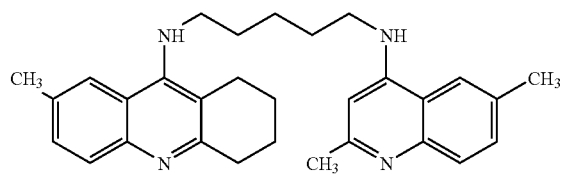
Compound 58
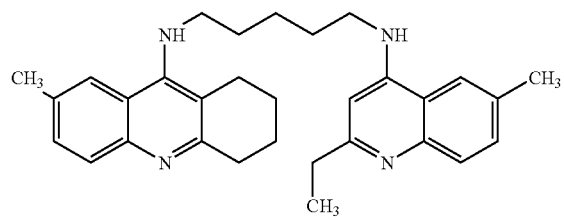
Compound 59
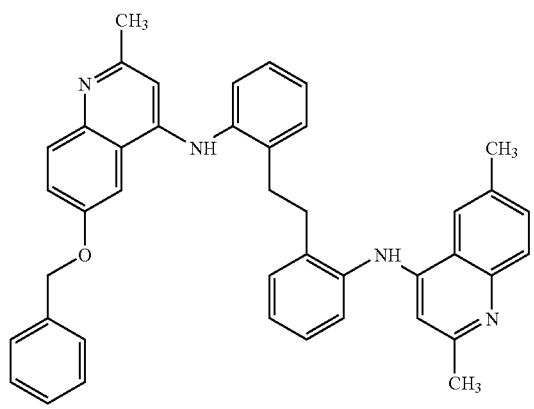

-continued
Compound 60
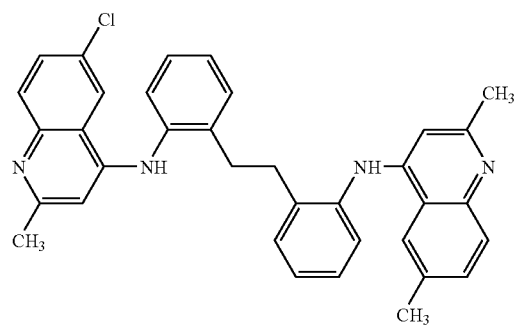
Compound 61
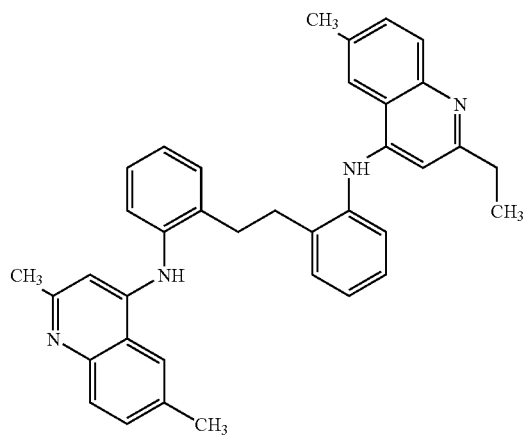
Compound 62
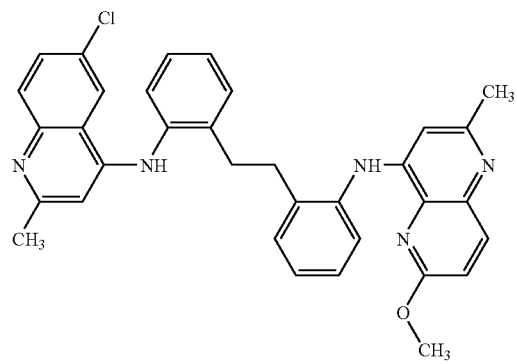
Compound 63
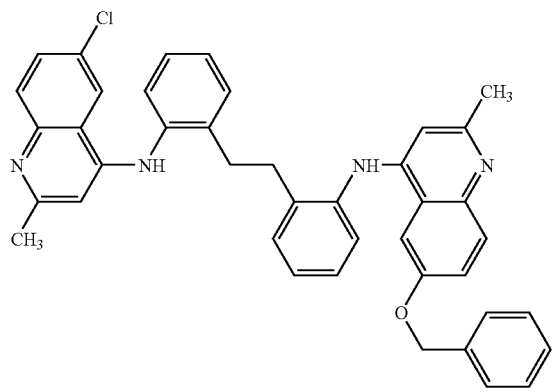
Compound 64
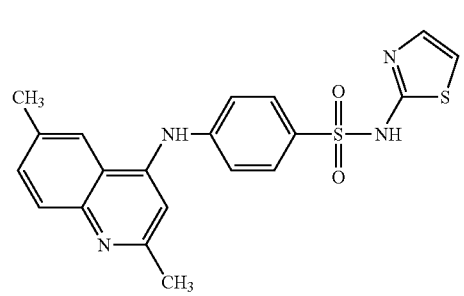
Compound 65
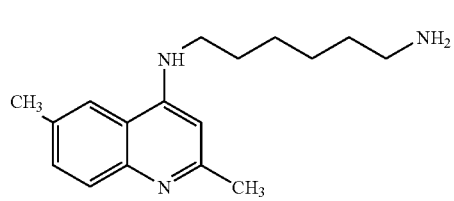
Compound 66
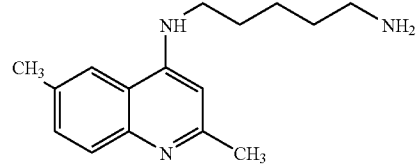
Compound 67
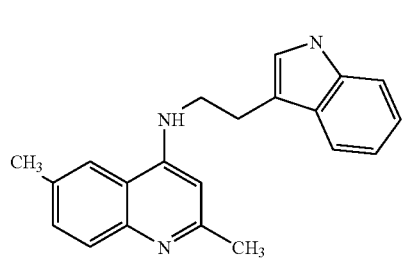

-continued
Compound 68
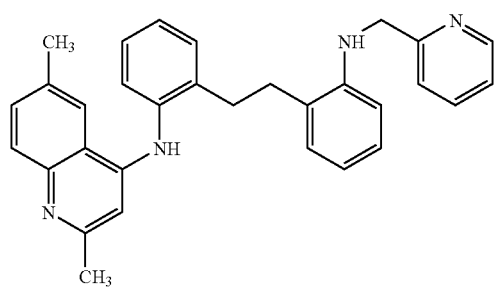
Compound 69
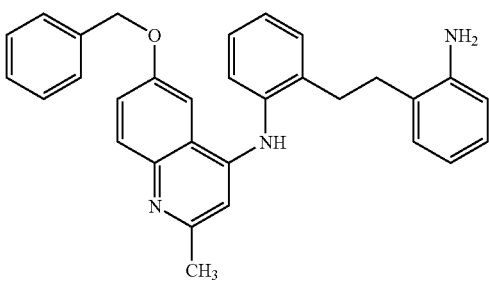
Compound 70
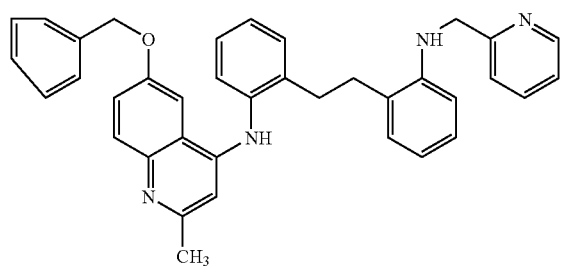
Compound 71
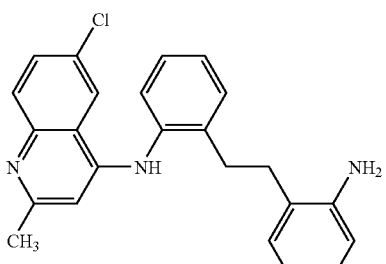
Compound 72
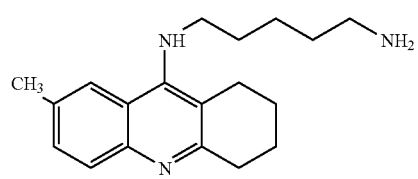
Compound 73
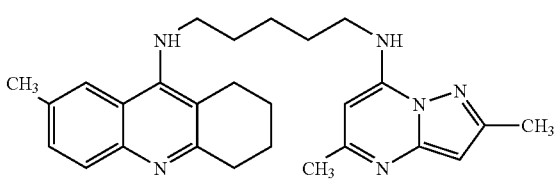
Compound 74
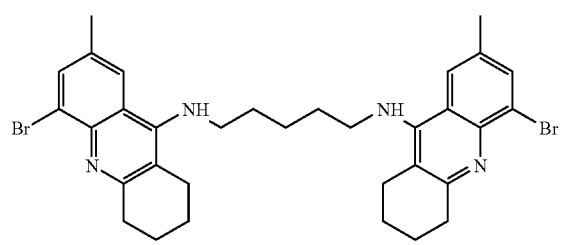
Compound 75
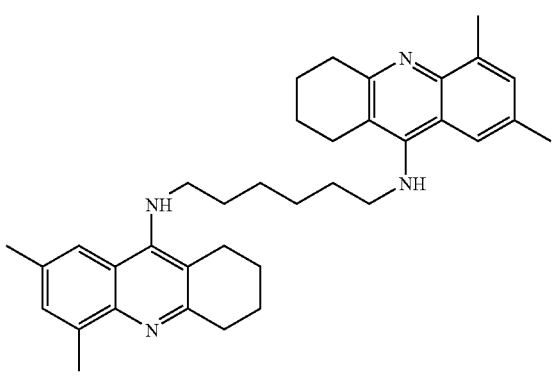
Compound 76
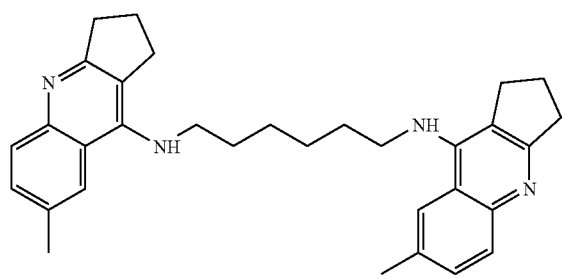
Compound 77
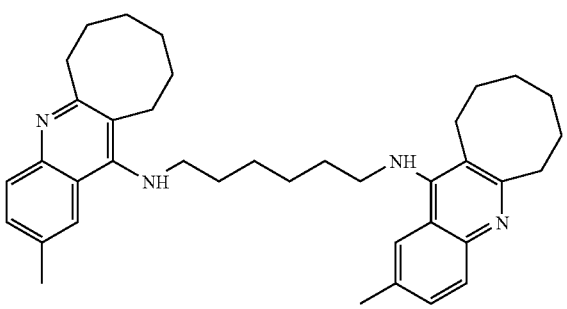

-continued
Compound 78
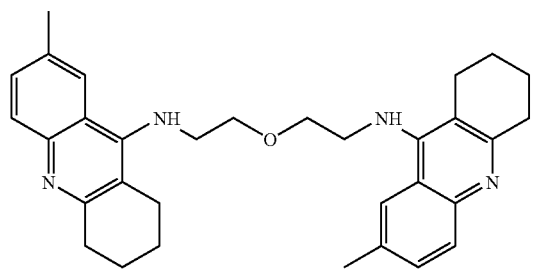
Compound 79
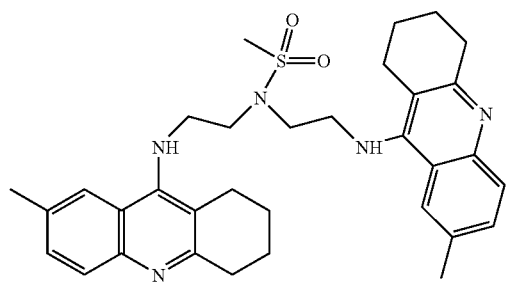
Compound 80
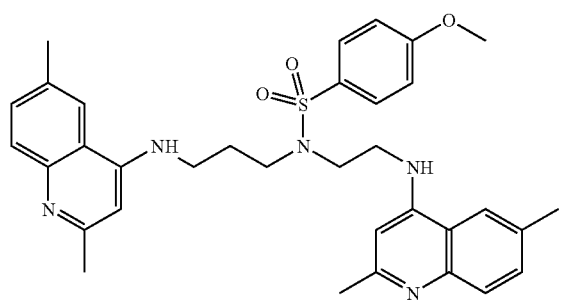
Compound 81
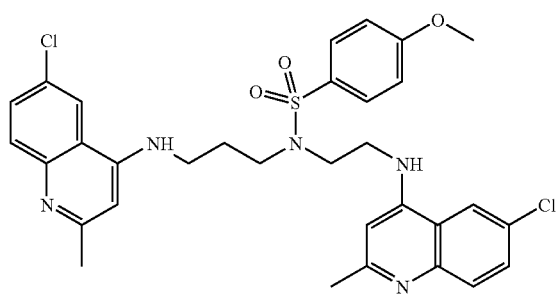
Compound 82
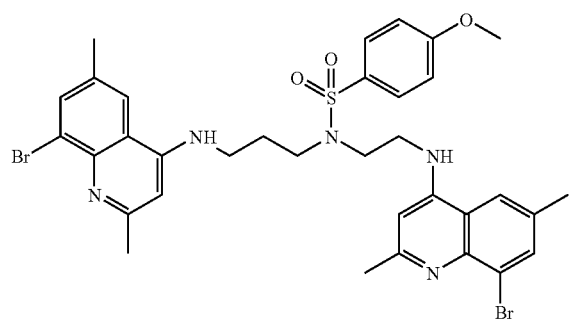
Compound 83
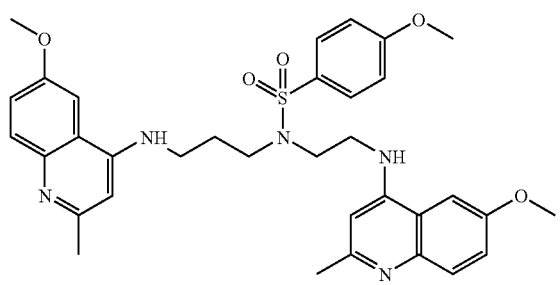
Compound 84
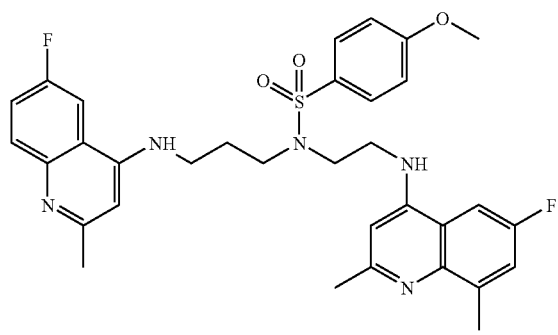
Compound 85
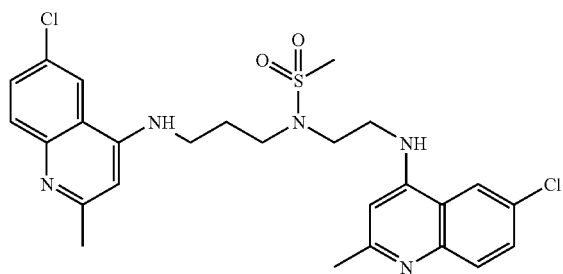

-continued
Compound 86
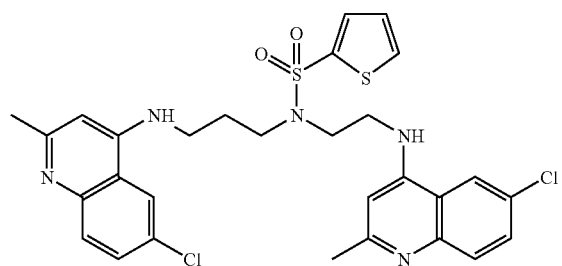
Compound 87
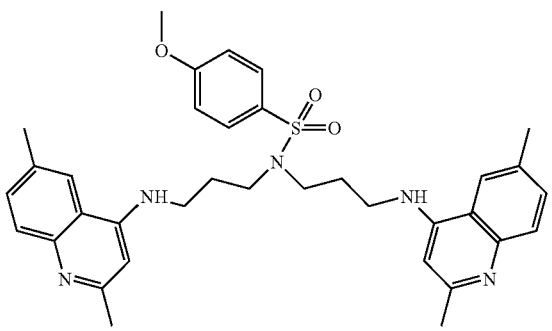
Compound 88
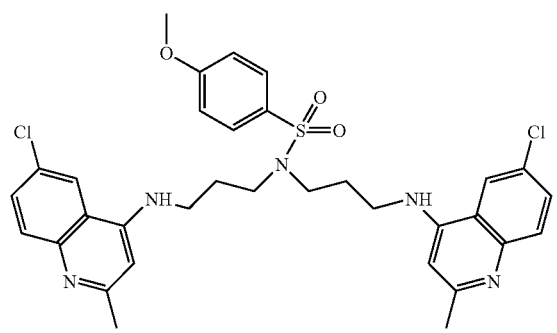
Compound 89
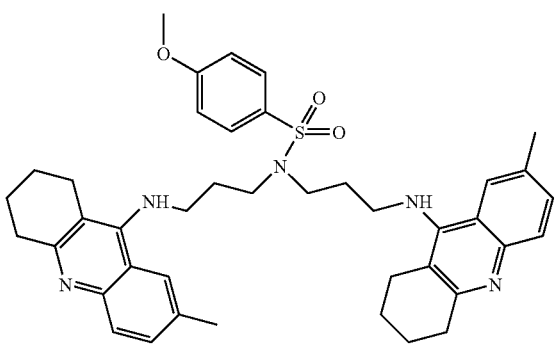
Compound 90
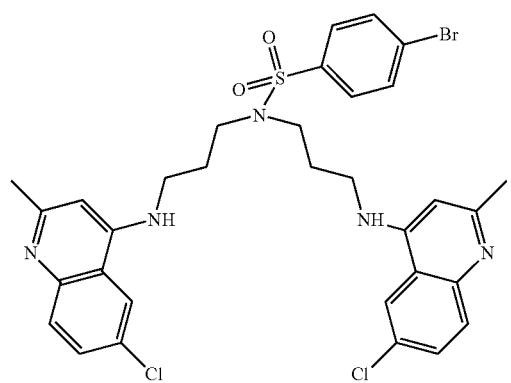
Compound 91
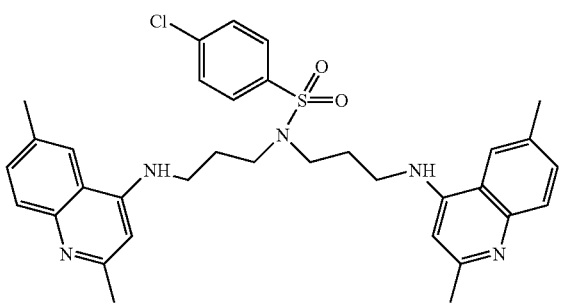
Compound 92
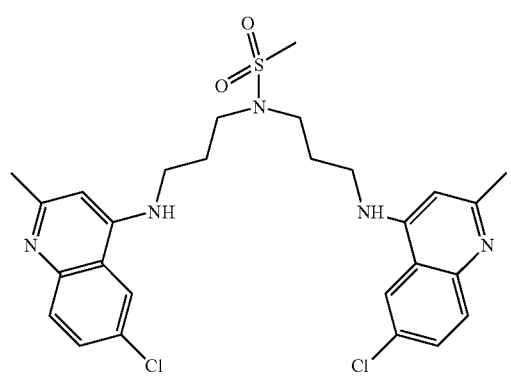
Compound 93
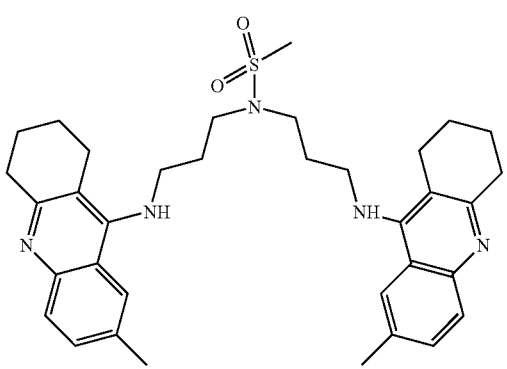

-continued
Compound 94
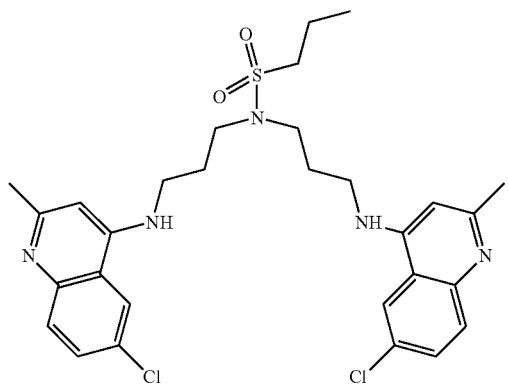
Compound 95
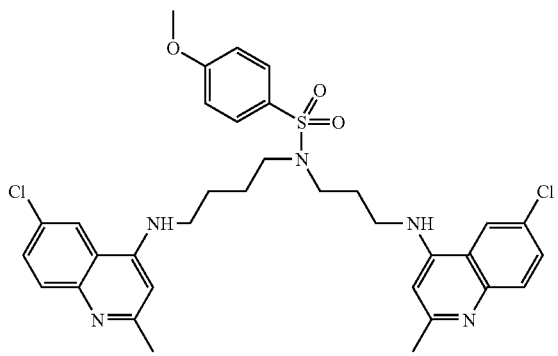
Compound 96
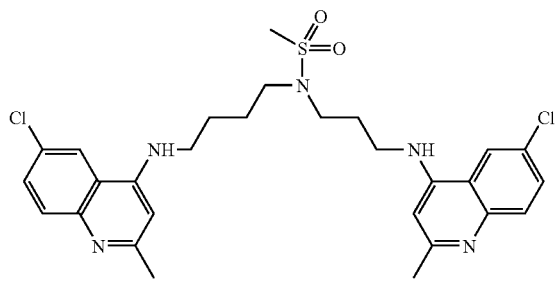
Compound 97
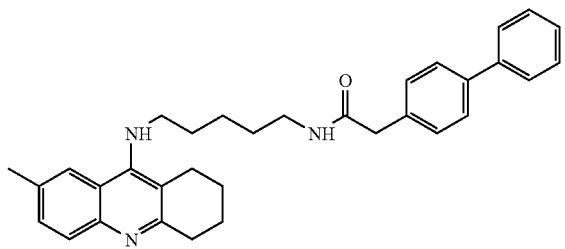
Compound 98
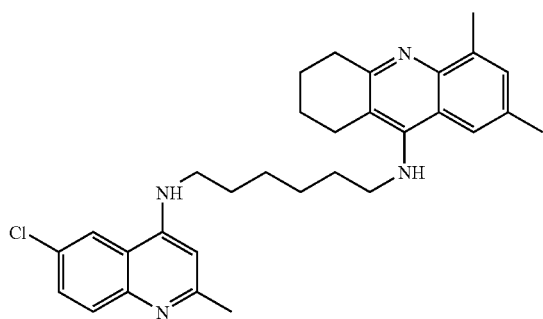
Compound 99
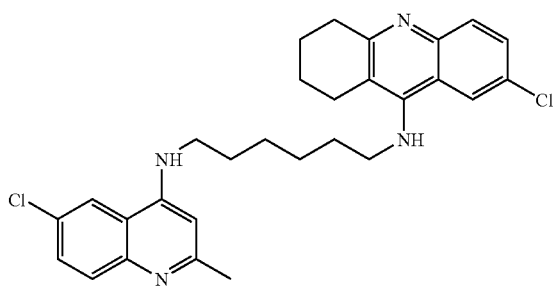
Compound 100
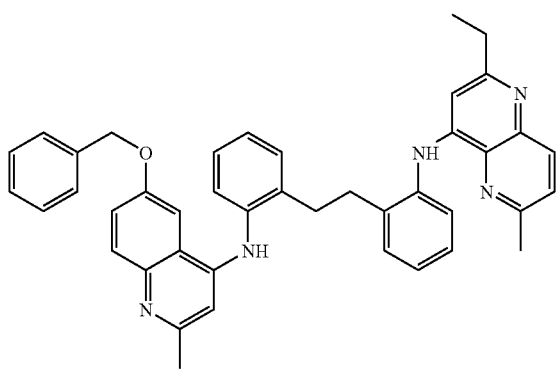
Compound 101
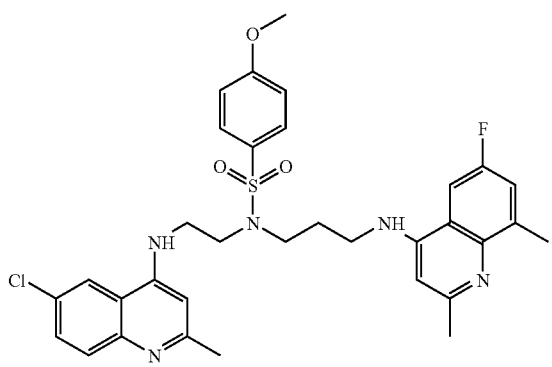

-continued
Compound 102
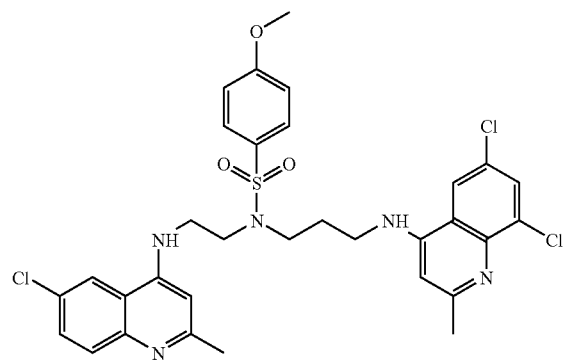
Compound 103
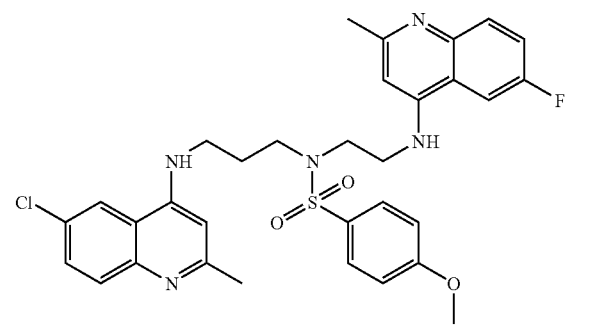
Compound 104
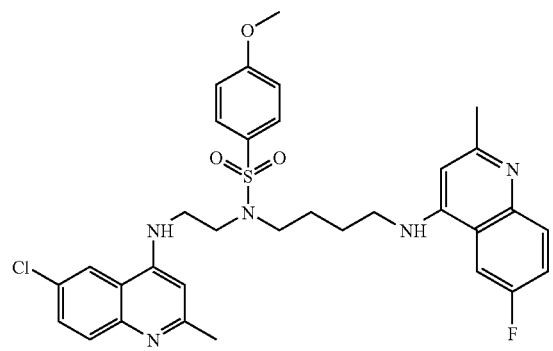
Compound 105
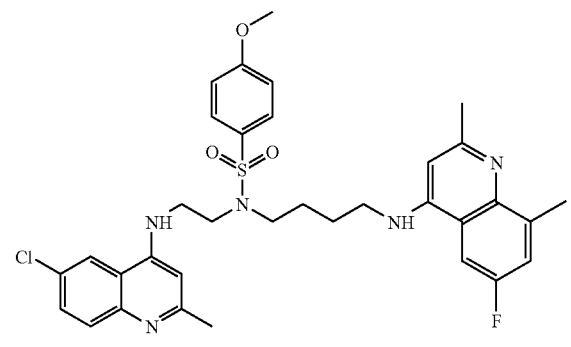
Compound 106
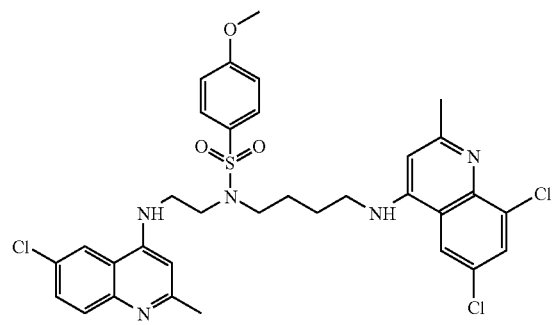
Compound 107
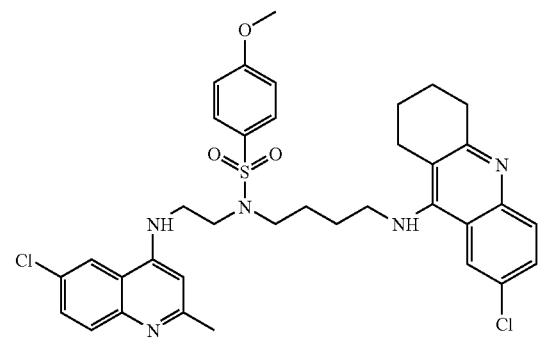
Compound 108
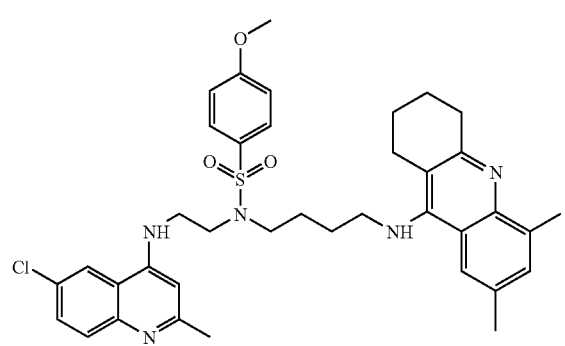
Compound 109
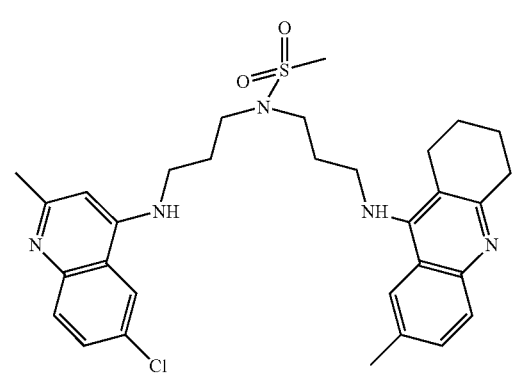

-continued
Compound 110
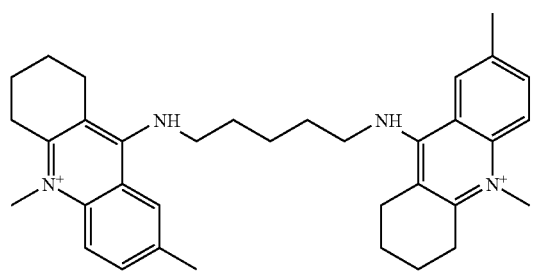
Compound 111
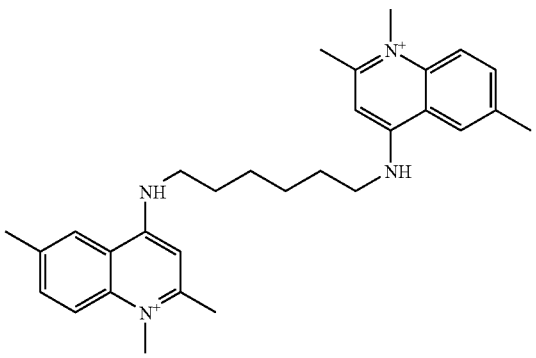
Compound 112
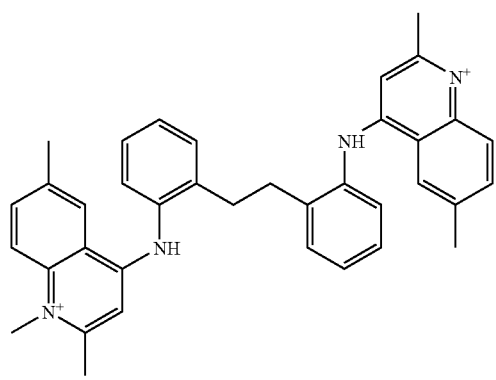
Compound 113
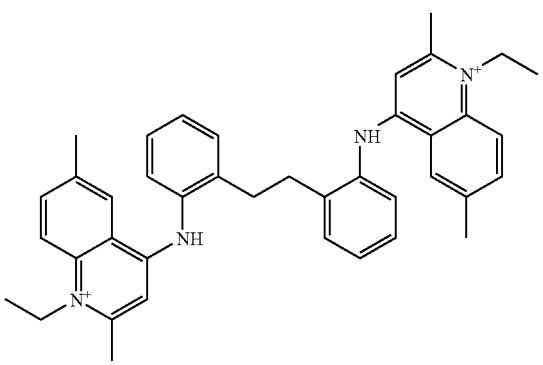
Compound 114
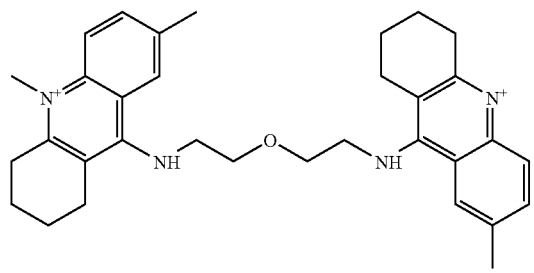
Compound 115
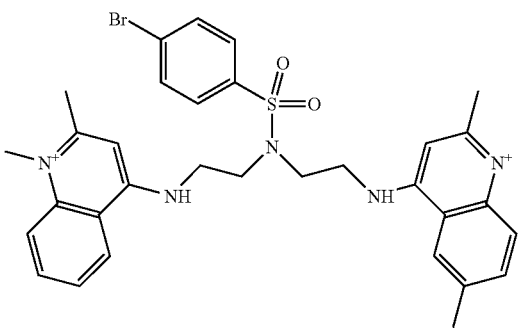
Compound 116
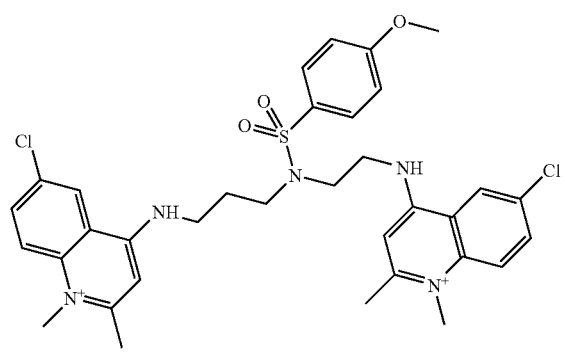
Compound 117
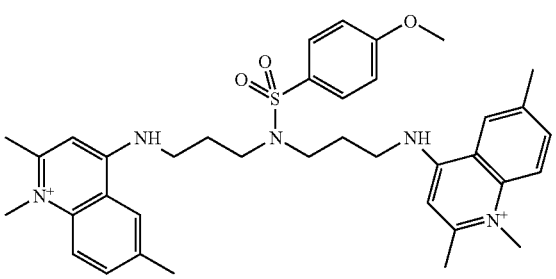

-continued
Compound 118
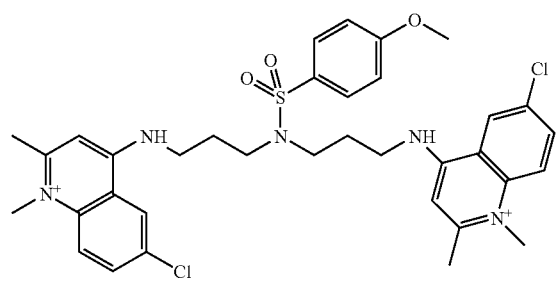
Compound 119
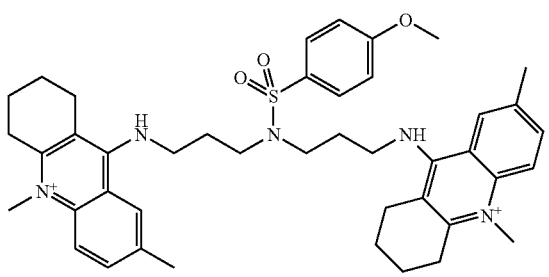
Compound 120
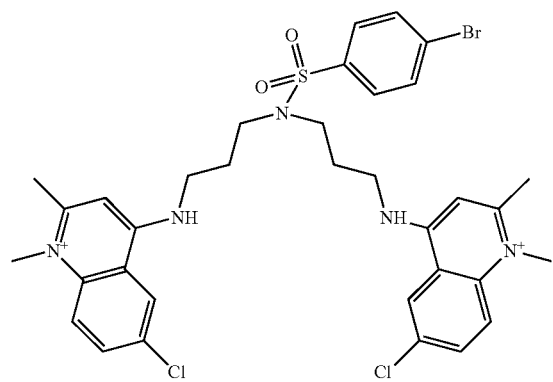
Compound 121
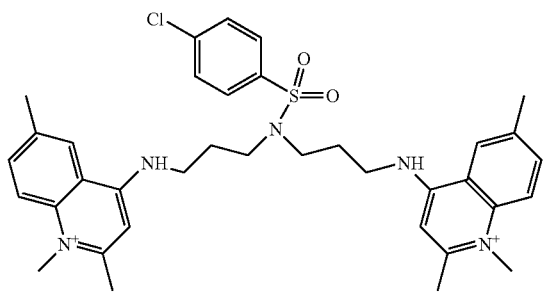
Compound 122
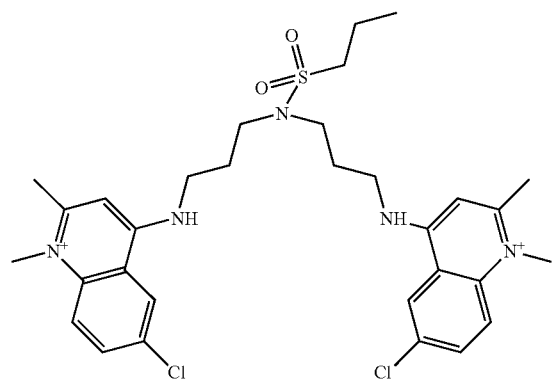
Compound 123
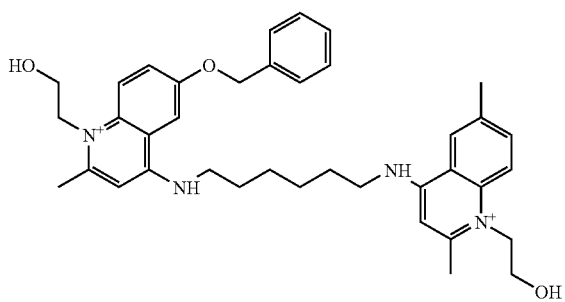
Compound 124
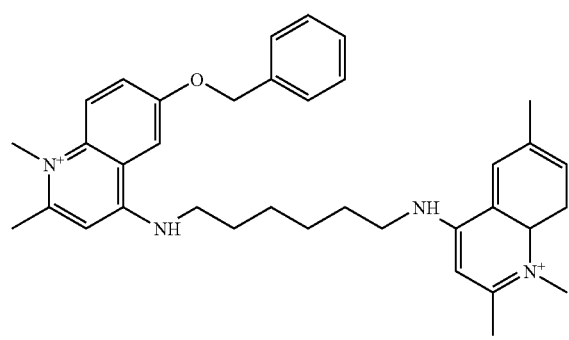
Compound 125
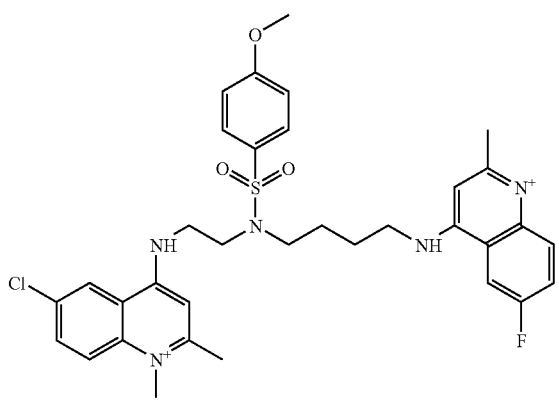

-continued
Compound 126
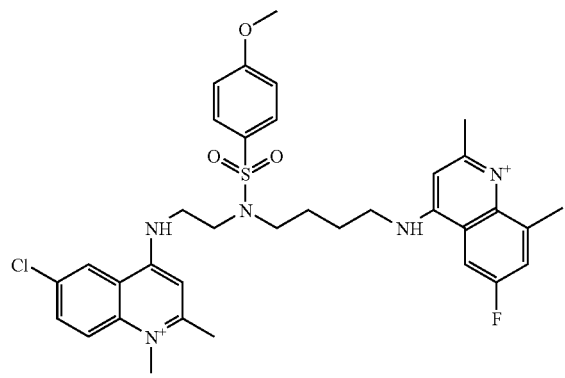
Compound 127
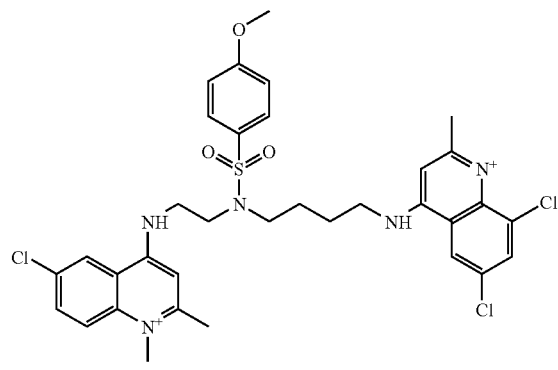
Compound 128
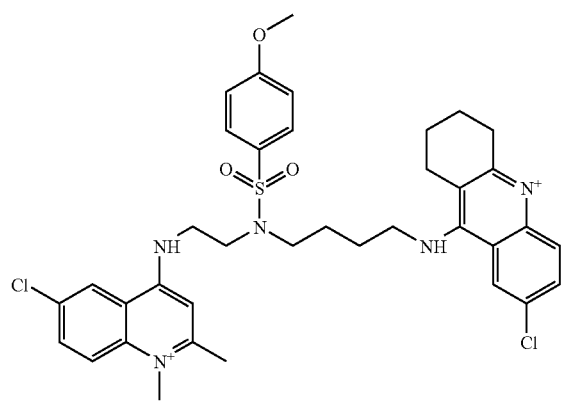
Compound 129
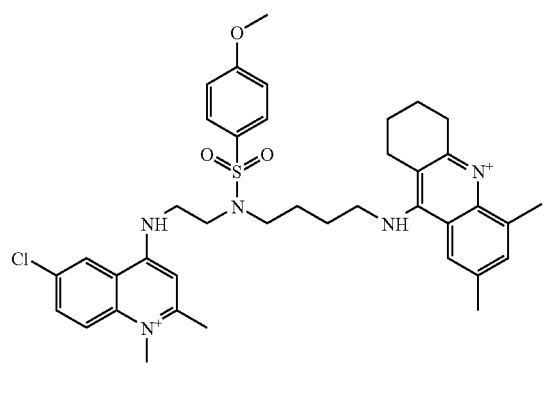
Compound 130
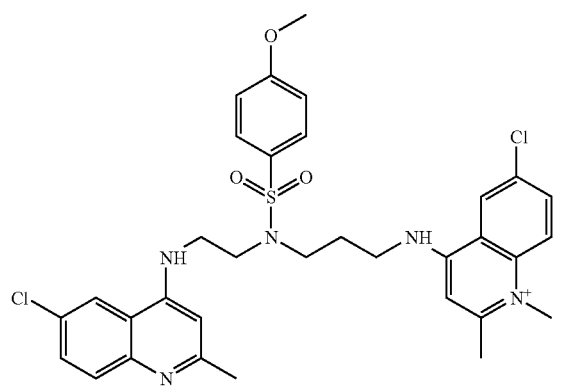
Compound 131
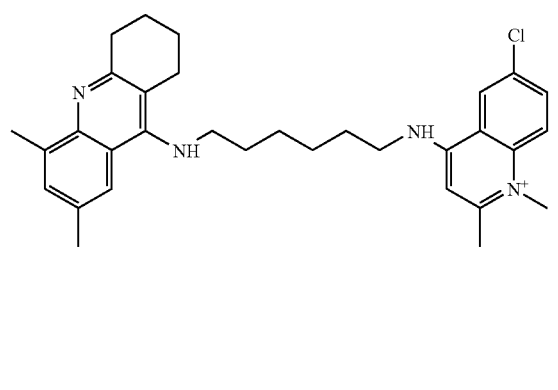
Compound 132
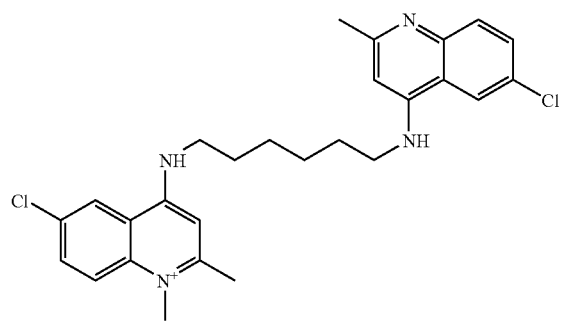
Compound 133
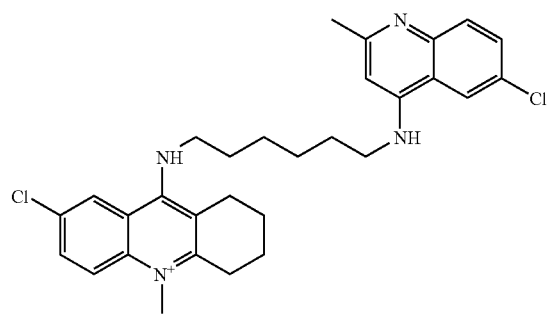

-continued
Compound 134
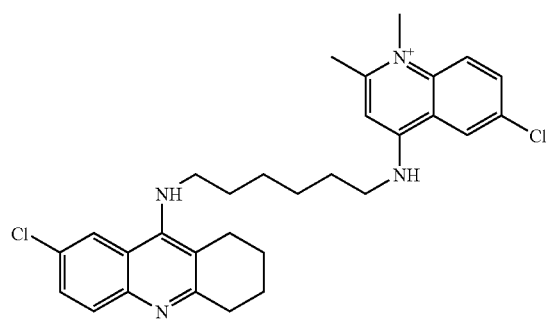
Compound 135
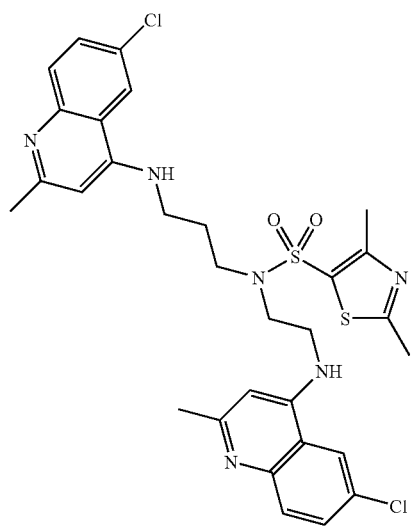
Compound 136
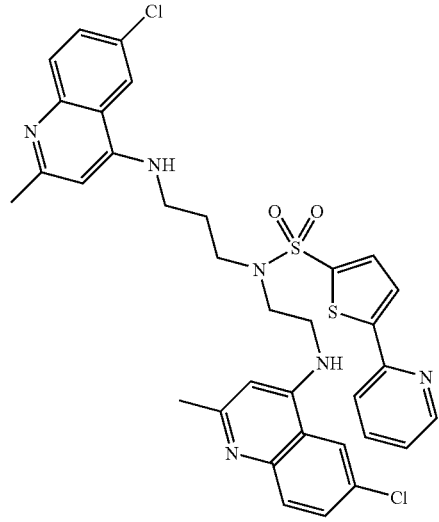
Compound 137
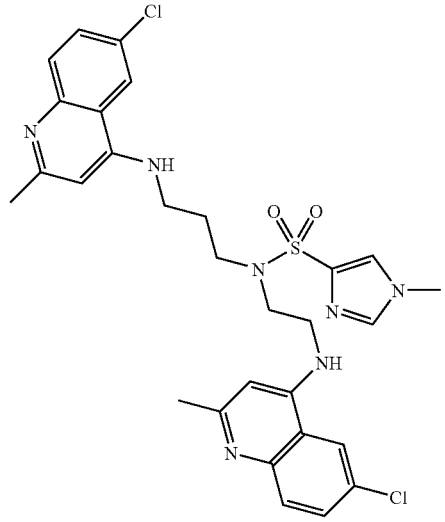
Compound 138
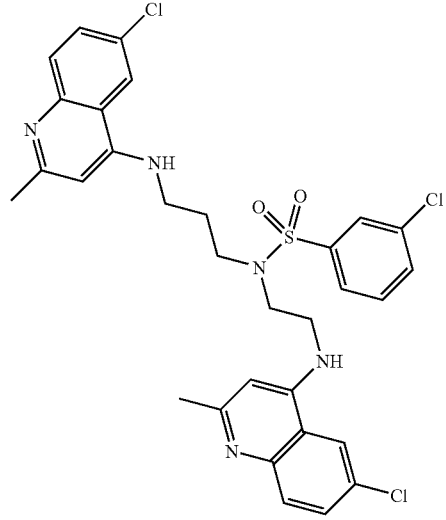
Compound 139
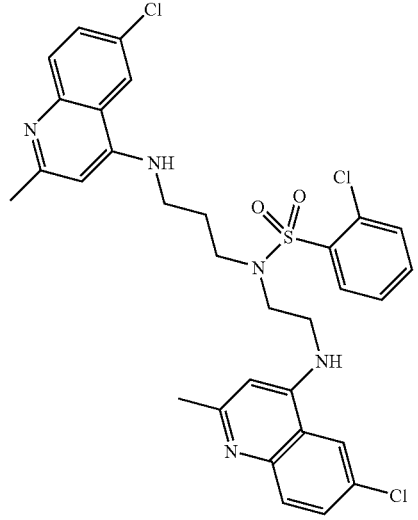

Compound 140
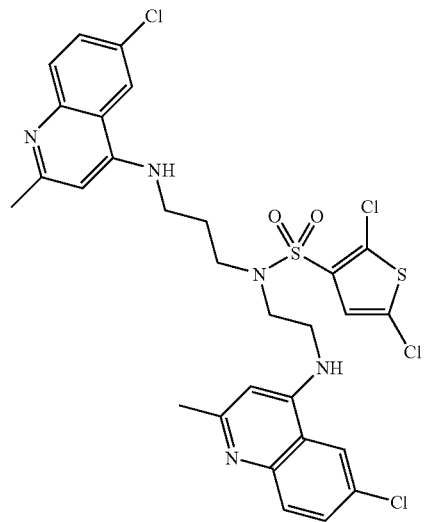
Compound 141
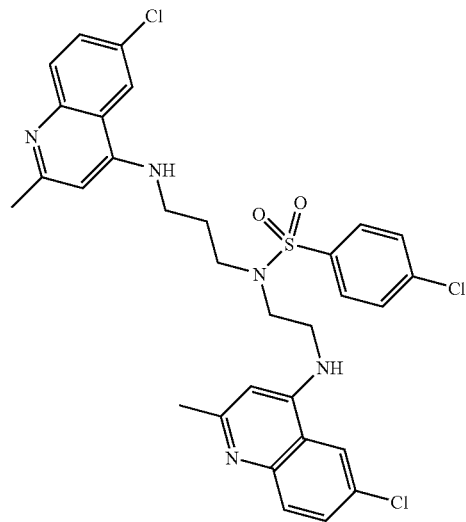
Compound 142
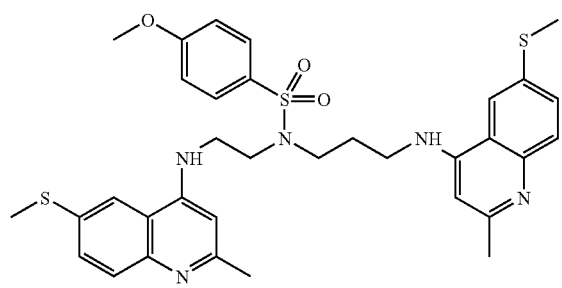
Compound 143
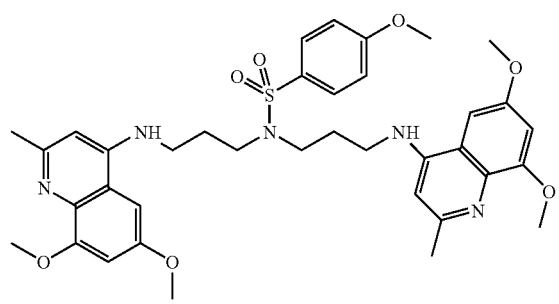
Compound 144
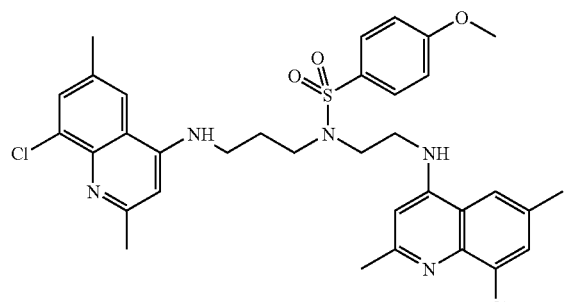
Compound 145
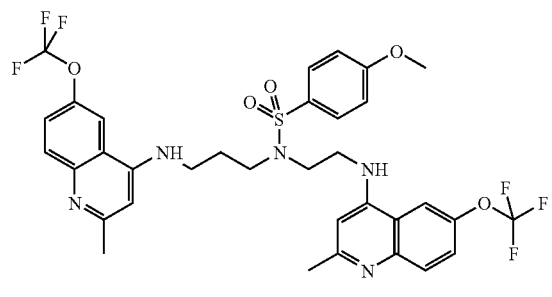
Compound 146
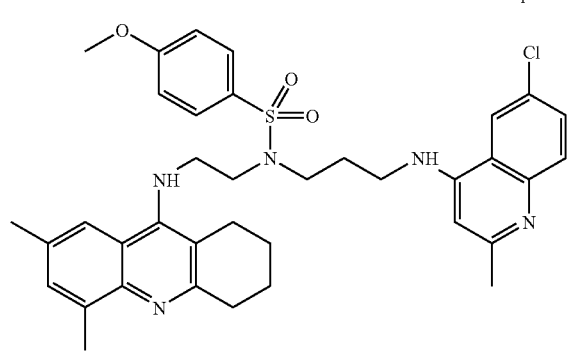
Compound 147
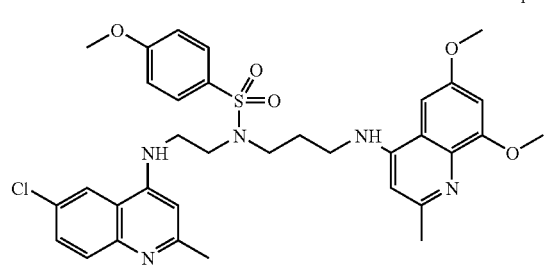

-continued
Compound 148
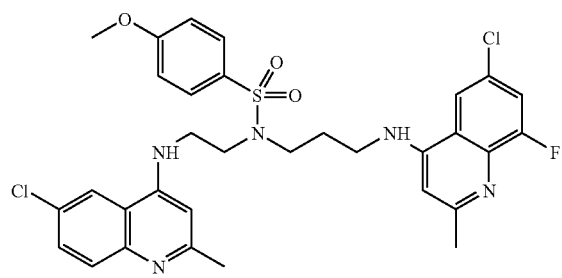
Compound 149
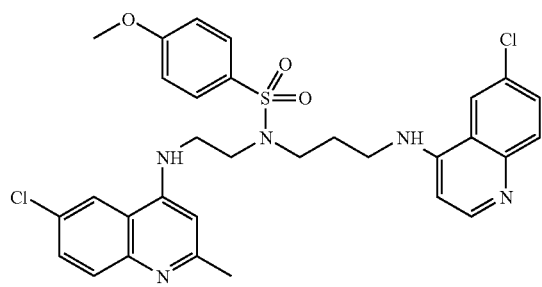
Compound 150
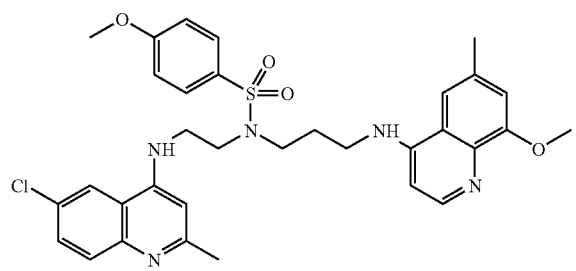
Compound 151
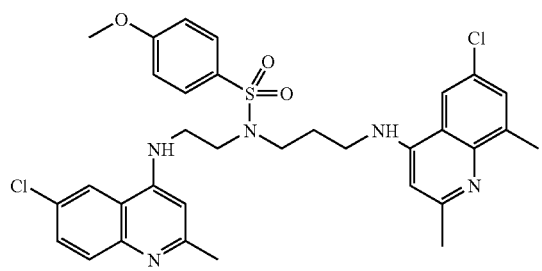
Compound 152
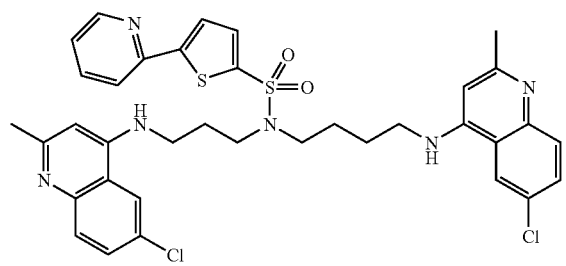
Compound 153
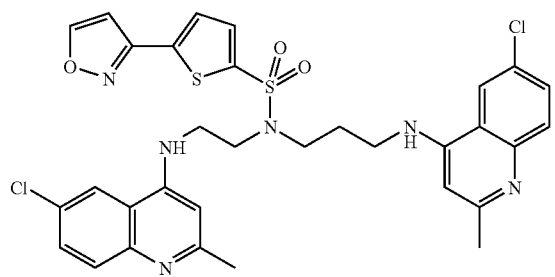
Compound 154
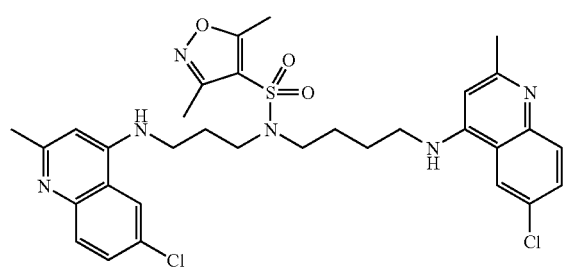
Compound 155
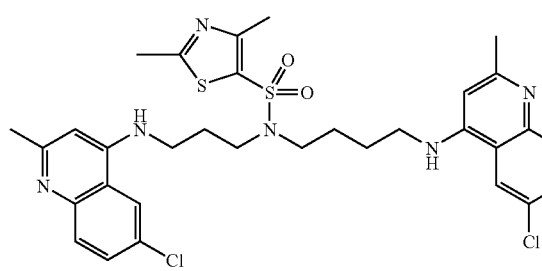
Compound 156
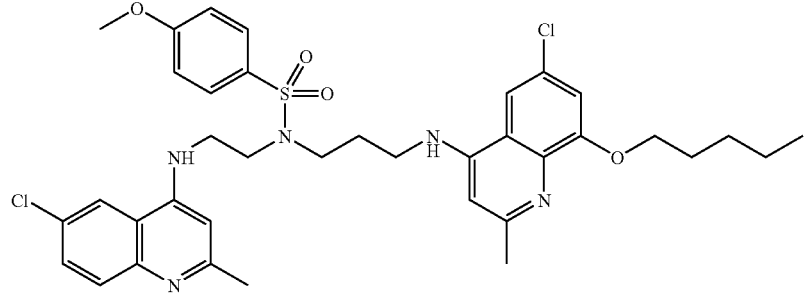

-continued
Compound 157
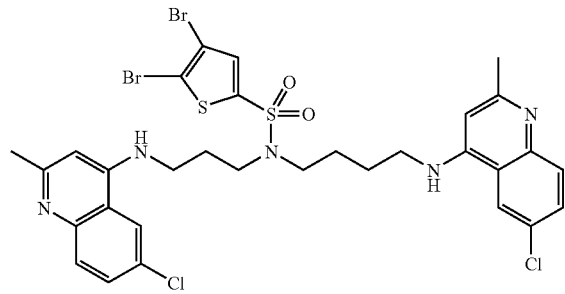
Compound 158
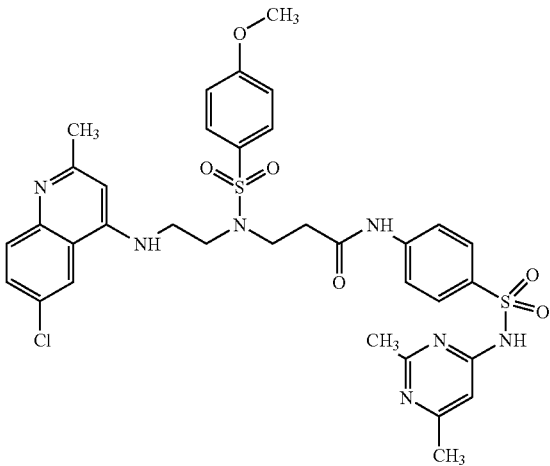
Compound 159
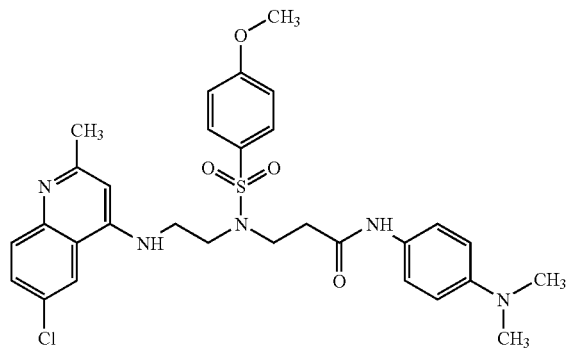
Compound 160
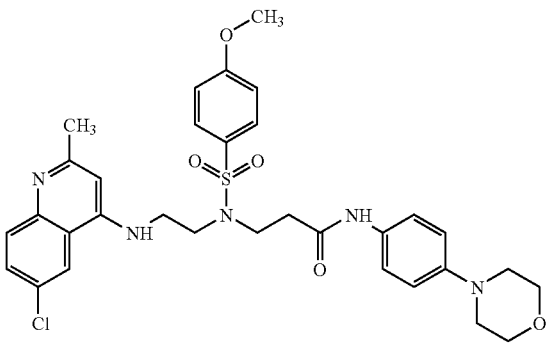
Compound 161
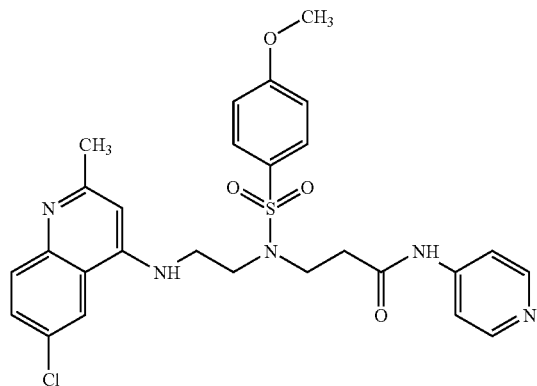
Compound 162
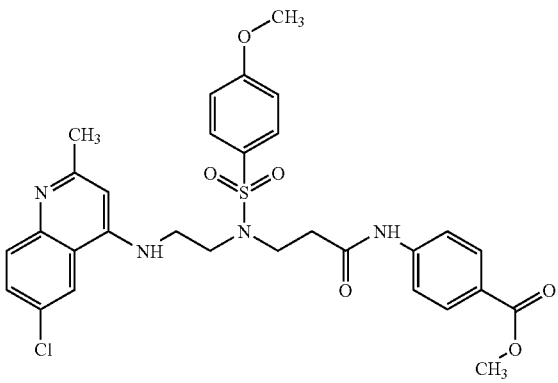

Compound 163
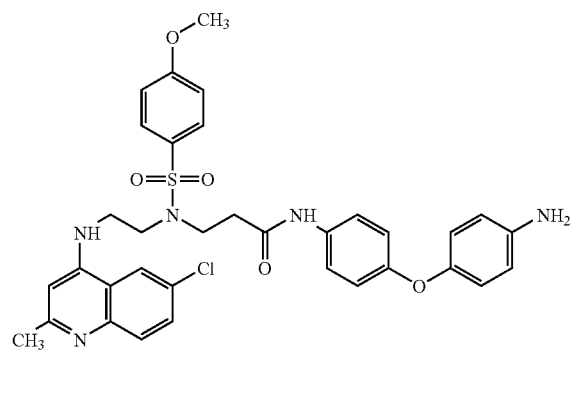
Compound 164
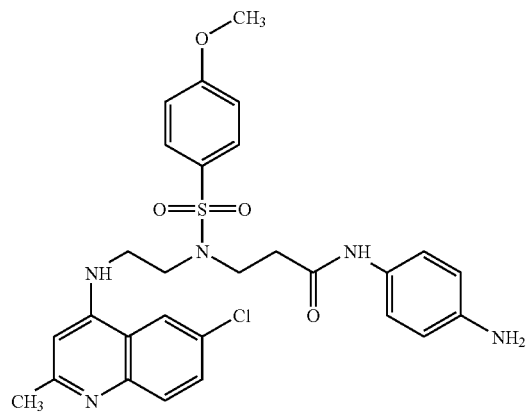
Compound 165
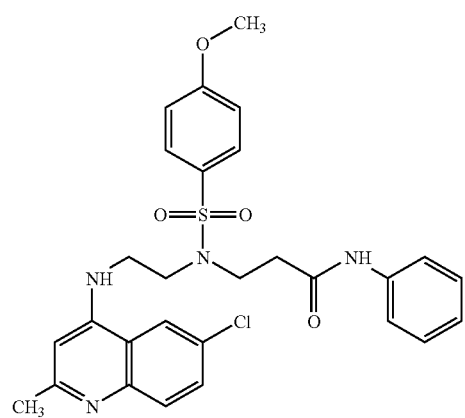
Compound 166
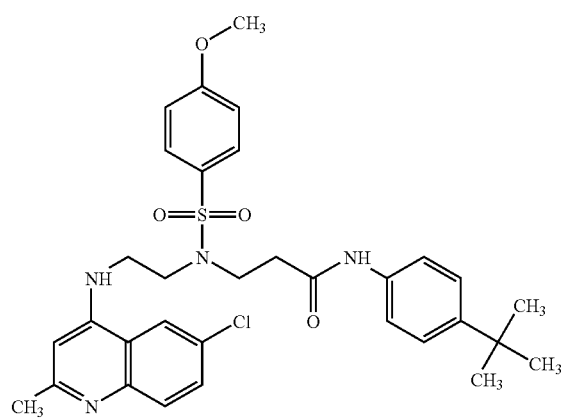
Compound 167
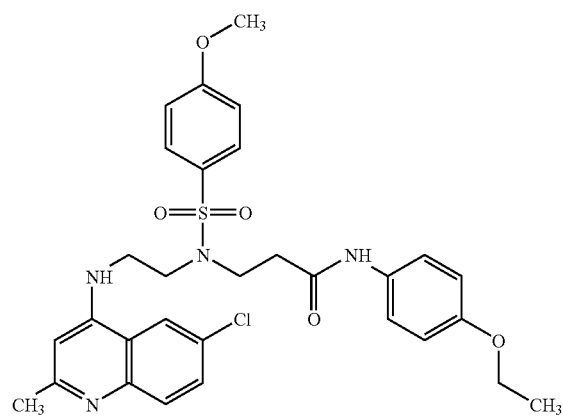
Compound 168
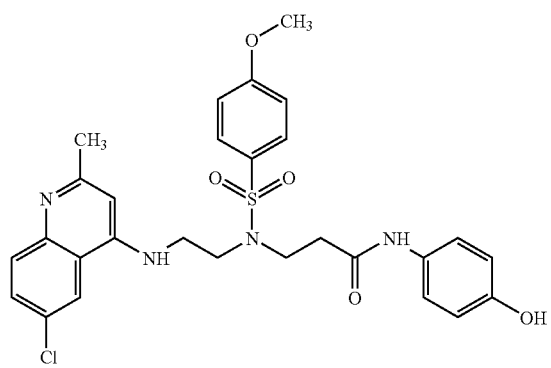

Compound 169
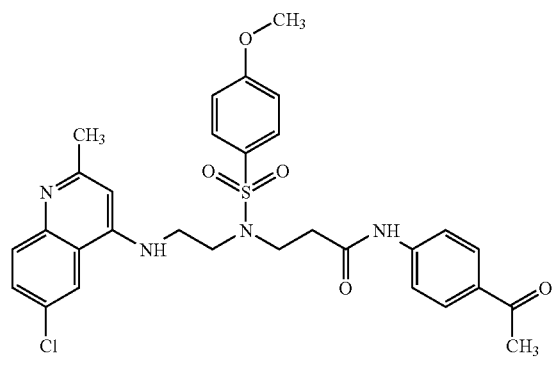
Compound 170
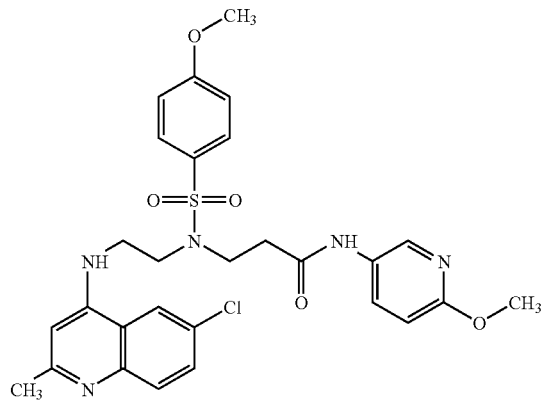
Compound 171
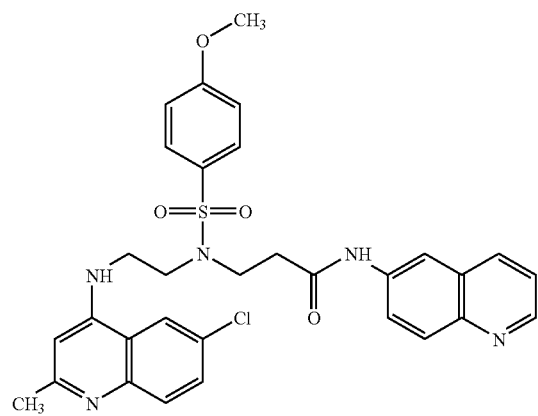
Compound 172
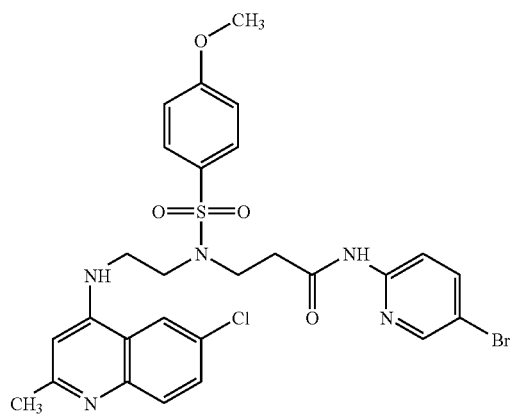
Compound 173
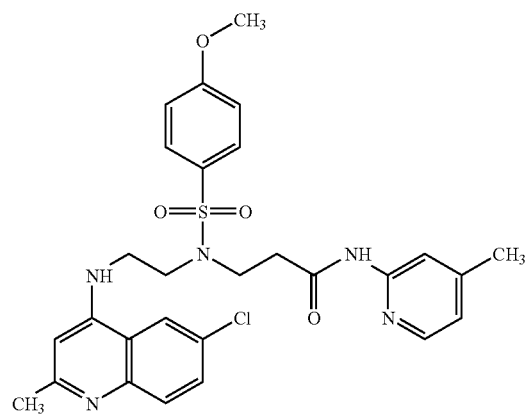
Compound 174
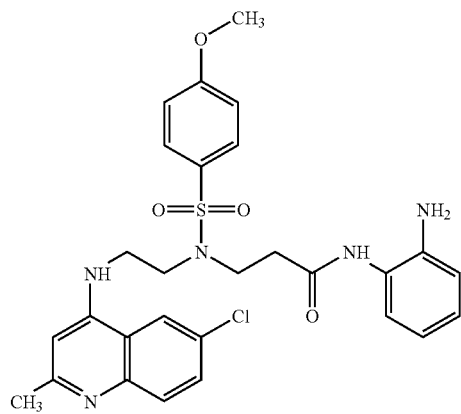

-continued
Compound 175
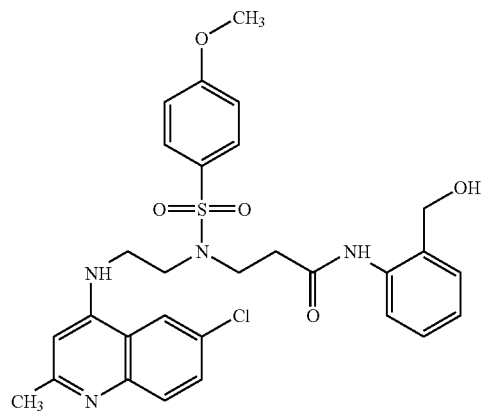
Compound 176
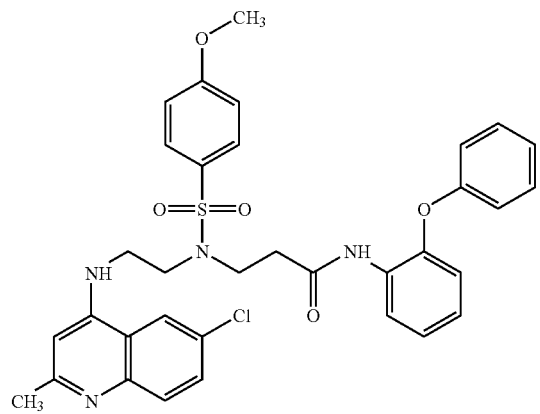
Compound 177
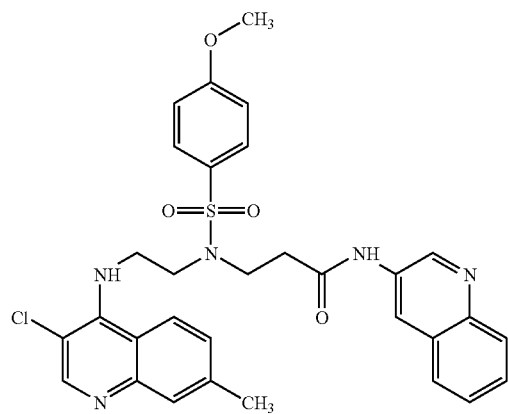
Compound 178
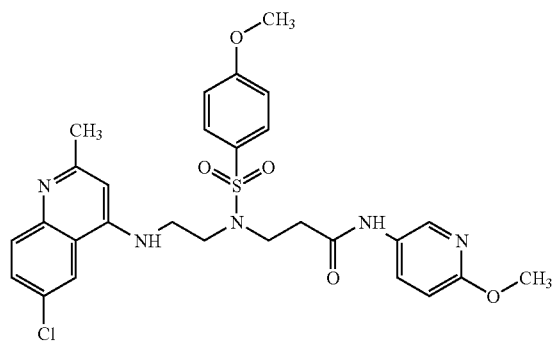
Compound 179
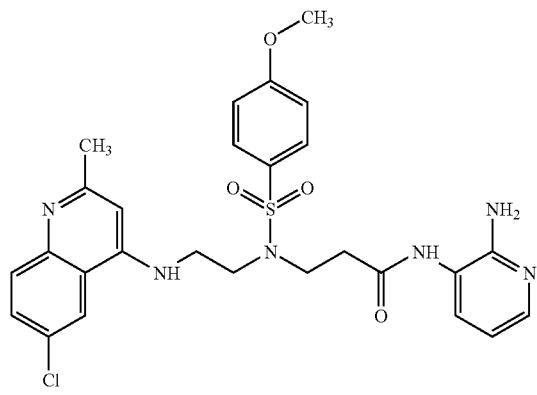
Compound 180
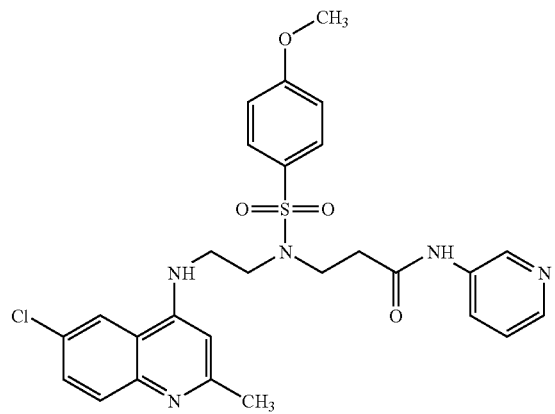

-continued
Compound 181
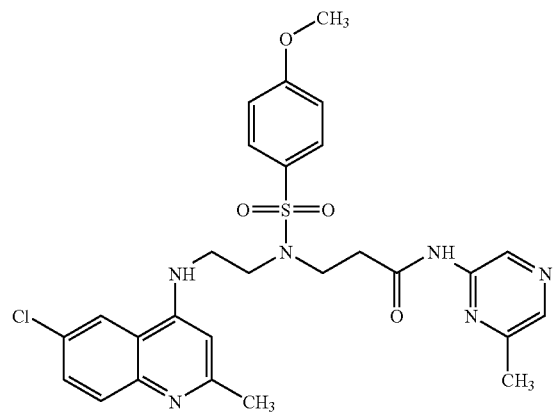
Compound 182
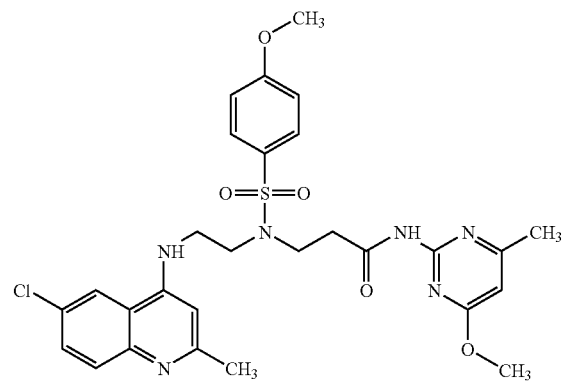
Compound 183
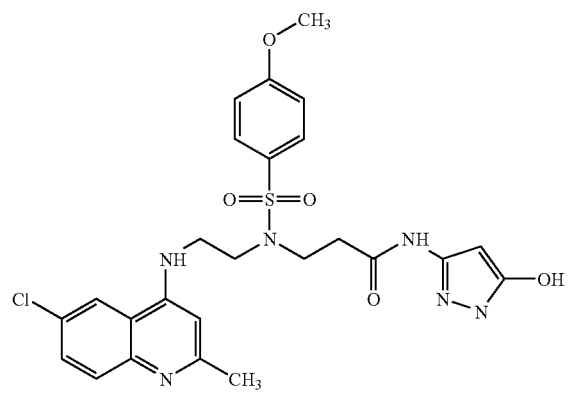
Compound 184
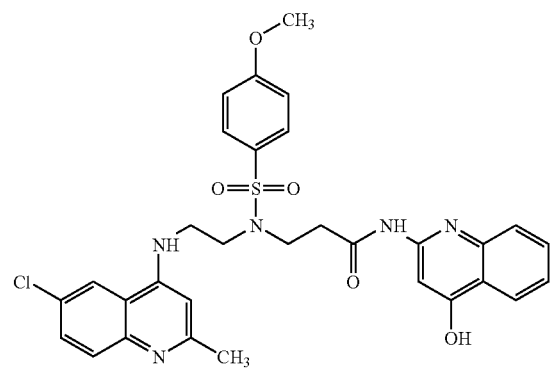
Compound 185
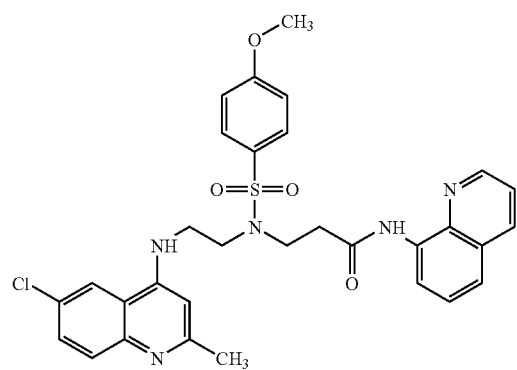
Compound 186
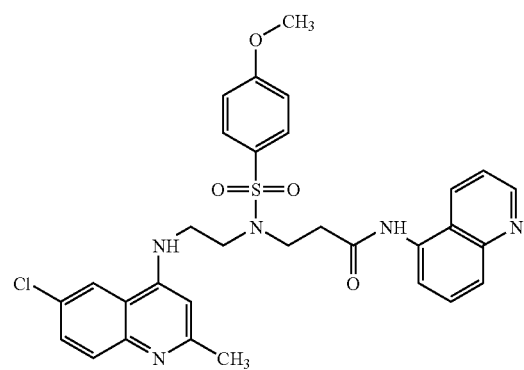

Compound 187
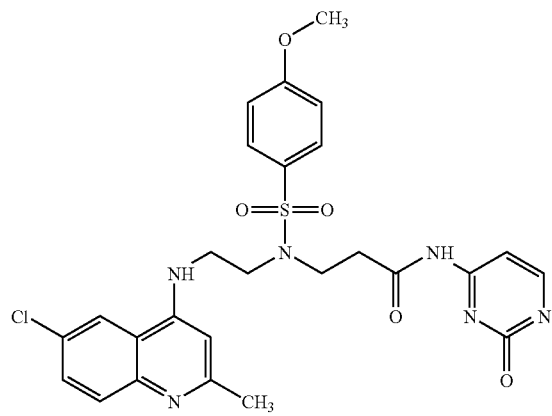
Compound 188
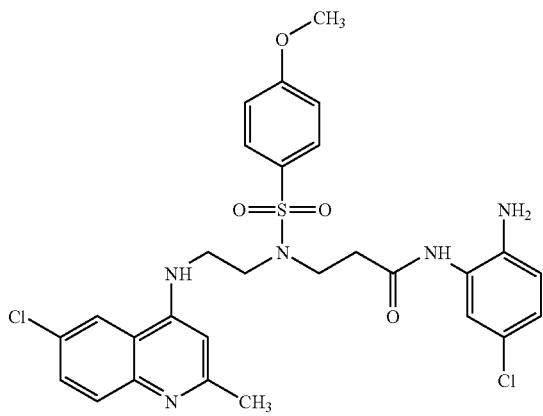
Compound 189
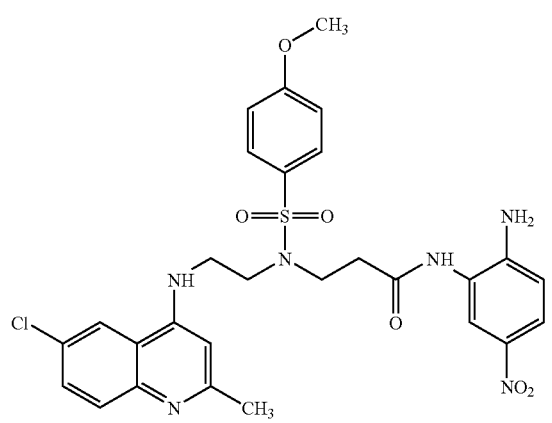
Compound 190
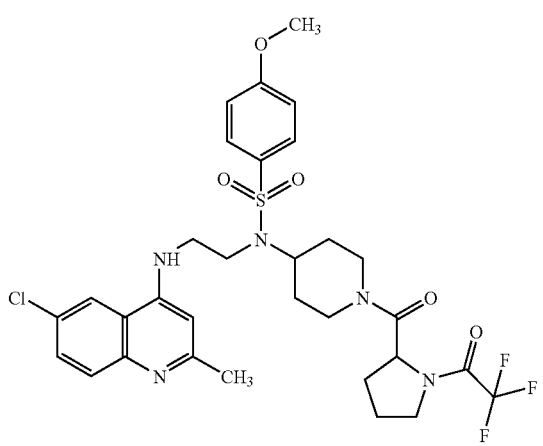
The scheme below depicts the syntheses of exemplary aminoquinoline compounds, i.e., compounds 1–190. Details of preparation of these compounds are provided in Examples 1–190, respectively.
Route I
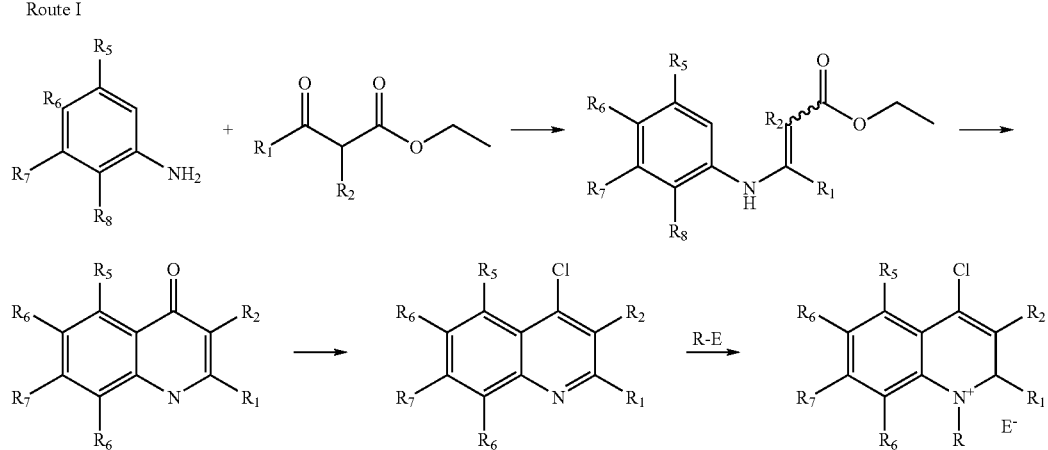

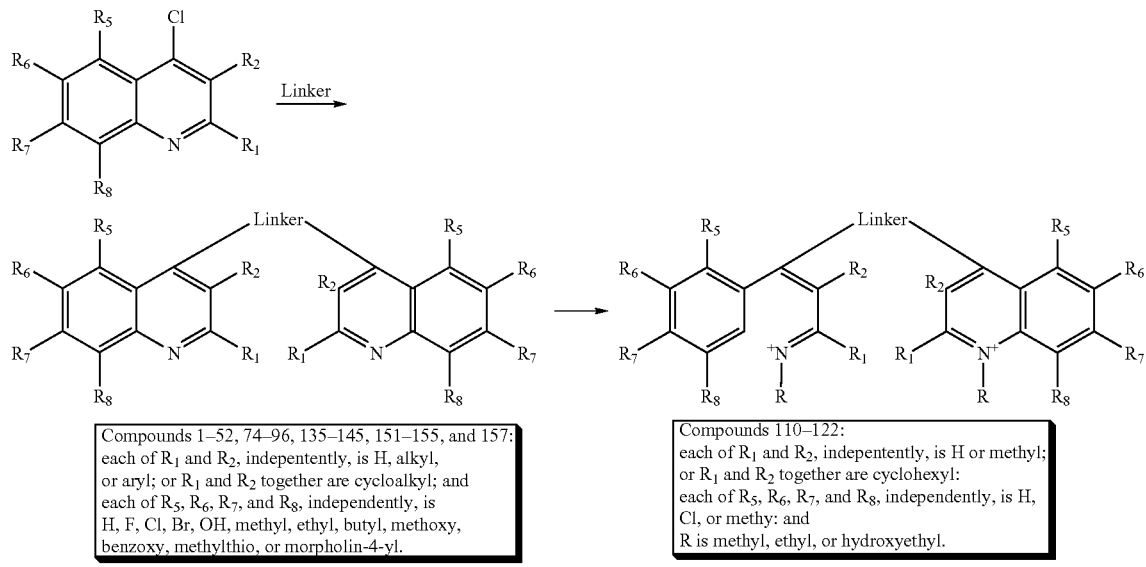
Route II
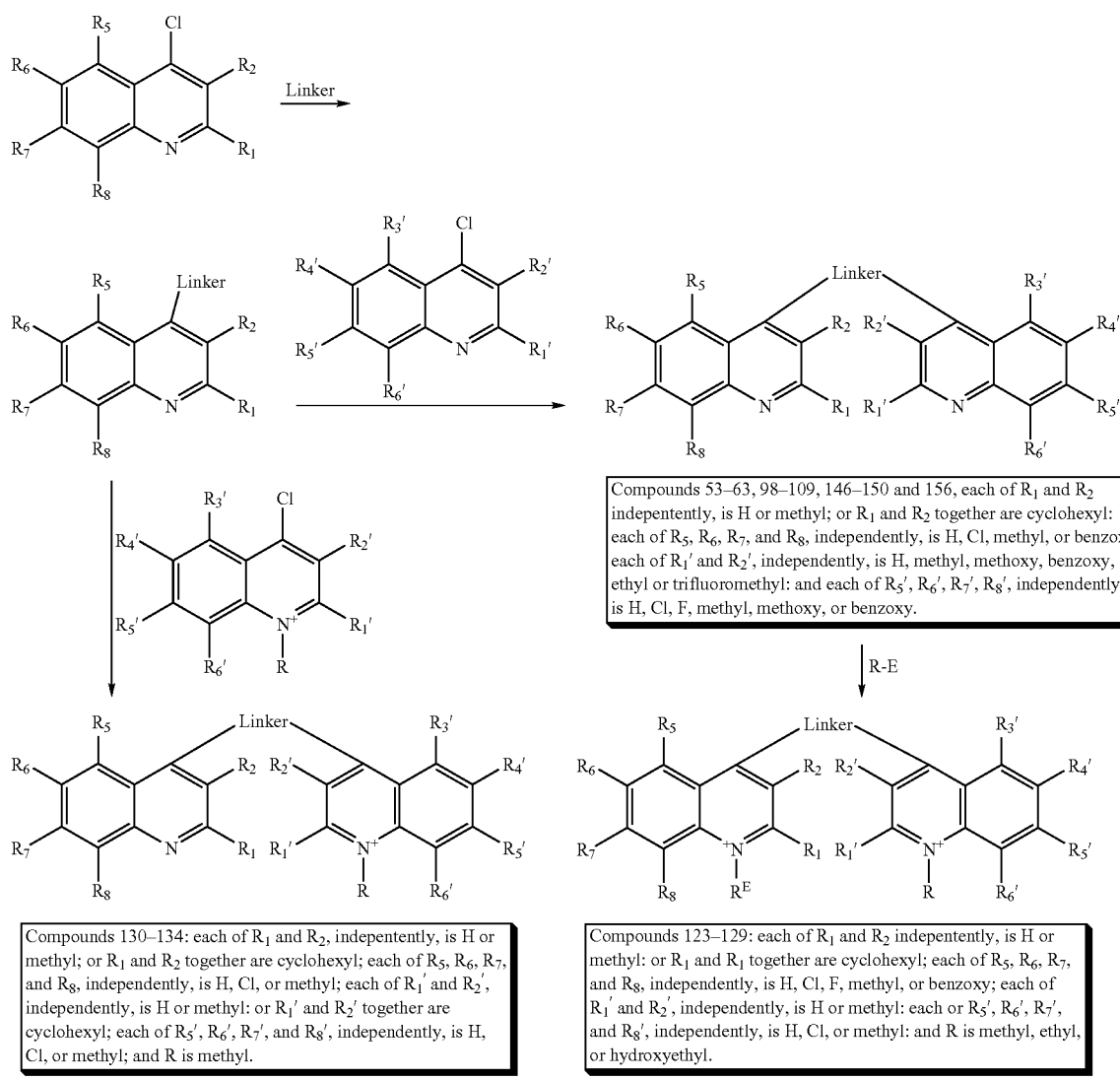

Route III

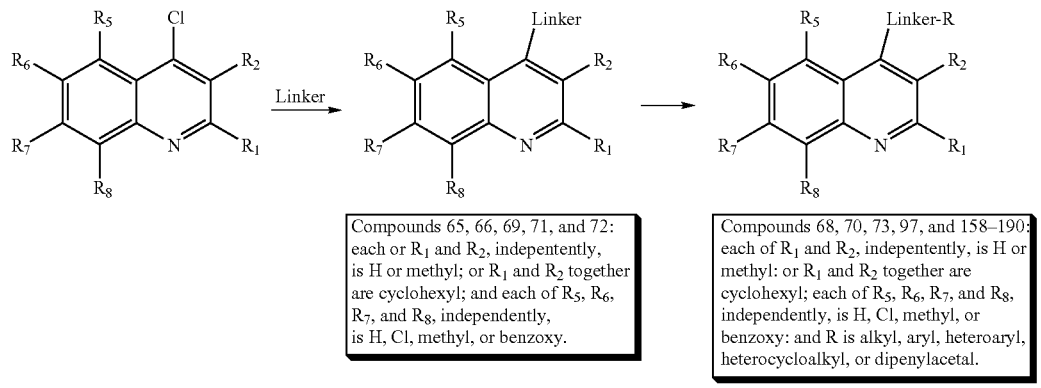

Route IV

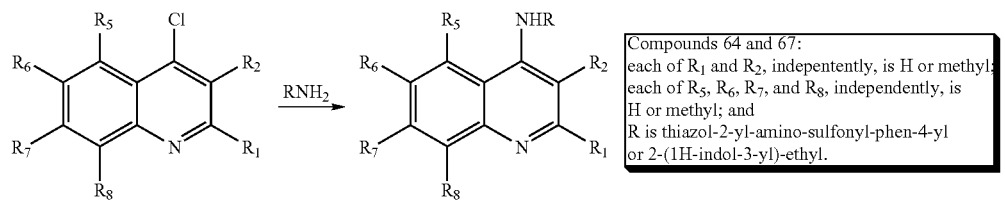

For example, referring to the scheme shown above, an aniline derivative is reacted with a β-keto ester to produce an enamine. A quinolinone derivative is formed through a ring closure reaction by heating the enamine at a high temperature for a short period time, and is then converted to a 4-chloro-quinoline derivative upon reacting with phosphorus oxychloride. A compound described in the summary section above can be obtained by (1) reacting the 4-chloro-quinoline derivative with a linker containing at least two amino groups in a 2/1 ratio (Route I), (2) reacting the 4-chloro-quinoline derivative with a linker in a 1/1 ratio and then with another chloro-containing compound in a 1/1 ratio (Routes II and III), or (3) reacting the 4-chloro-quinoline derivative with an amino-containing compound (Route IV).

Other amionquinoline compounds can be prepared using other suitable starting materials following the synthetic routes disclosed herein and other synthetic methods known in the art. The methods described above may also additionally include steps, either before or after the steps described specifically herein, to add or remove suitable protecting groups in order to ultimately allow synthesis of the amino-quinoline compounds. In addition, various synthetic steps may be performed in an alternate sequence or order to give the desired compounds. Synthetic chemistry transformations and protecting group methodologies (protection and deprotection) useful in synthesizing applicable aminoquinoline compounds are known in the art and include, for example, those described in R. Larock, Comprehensive Organic Transformations, VCH Publishers (1989); T. W. Greene and P. G. M. Wuts, Protective Groups in Organic Synthesis, 2nd Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The aminoquinoline compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition contains an effective amount of at least one aminoquinoline compound described above and a pharmaceutical acceptable carrier. Further, this invention covers a method of administering an effective amount of one or more of the aminoquinoline compounds to a patient with an inflammatory or immune disease. Effective doses will vary, as recognized by those skilled in the art, depending on the types of diseases treated, route of administration, excipient usage, and the possibility of co-usage with other therapeutic treatment.

To practice the method of the present invention, a composition having one or more aminoquinoline compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active aminoquinoline compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active aminoquinoline compound. Examples of other carriers include colloidal silicon oxide, magnesium stearate, cellulose, sodium lauryl sulfate, and D&C Yellow #10.

The aminoquinoline compounds of this invention can be preliminarily screened for their efficacy in treating inflammatory or immune diseases by an in vitro assay (See Example 191 below) and then confirmed by animal experiments and clinical trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Compound 1 was prepared following the procedures described below:

p-Toluenesulfonic acid (catalytic amount) was added to a solution of p-methylaniline (10.7 g, 100 mmol) and ethyl acetoacetate (13.0 g, 110 mmol) in benzene (250 mL) at room temperature. The reaction mixture was refluxed with a Dean-Stark apparatus over night. After cooling down to room temperature, the reaction mixture was concentrated and purified by column chromatography (5% ethyl acetate in n-hexane) to give 3-p-tolylamino-but-2-enoic acid ethyl ester (18.6 g, 85% yield).

3-p-Tolylamino-but-2-enoic acid ethyl ester (21.9 g, 100 mmol) thus obtained was dissolved in phenyl ether (17.0 g, 100 mmol). The solution was heated to 120° C. for 5 minutes. The temperature of reaction mixture was then quickly raised up to 250° C. for 15 min under nitrogen. After cooling down to room temperature, the reaction mixture was purified by re-crystallization from ethyl acetate (30 mL) to give 2,6-dimethyl-1H-quinolin-4-one (13.8 g, 80% yield).

A mixture of 2,6-dimethyl-1H-quinolin-4-one (17.3 g, 100 mmol) and phosphorus oxychloride (30 mL) was heated at 80° C. for 3 h. After cooling down to room temperature, the reaction mixture was poured onto ice. The resulting solution was carefully alkalinized to pH 8–9 with 0.5 N NaOH and saturated $Na_2CO_3$. The solution was extracted with $CH_2Cl_2$ (200 mL×3). The organic layer was separated, dried over magnesium sulfate, and concentrated under reduced pressure. The crude product was purified by column chromatography (10% ethyl acetate in n-hexane) to give 4-chloro-2,6-dimethyl-quinoline (12.4 g, 65% yield).

4-Chloro-2,6-dimethyl-quinoline (211 mg, 1.1 mmol) and 1,4-butadiamine (44 mg, 0.5 mmol) were dissolved in pentanol (5 mL). The solution was kept under reflux over night. After cooling down to room temperature, 0.5 N NaOH (5 mL) was added to the above reaction mixture. The reaction mixture was stirred at room temperature for another 30 minutes and then extracted with $CH_2Cl_2$ (10 mL×3). The organic layer was separated, dried over magnesium sulfate, and concentrated under reduced pressure. The crude product was then purified by column chromatography (2% $Et_3N$ in 1:1 n-hexane and ethyl acetate) to give compound 1.

LC/MS $(M+1)^+$: 399.0.

EXAMPLE 2

Compound 2 was prepared in a manner similar to that described in Example 1.
LC/MS $(M+1)^+$: 427.0.

EXAMPLE 3

Compound 3 was prepared in a manner similar to that described in Example 1.
LC/MS $(M+1)^+$: 441.0.

EXAMPLE 4

Compound 4 was prepared in a manner similar to that described in Example 1.
LC/MS $(M+1)^+$: 469.1.

EXAMPLE 5

Compound 5 was prepared in a manner similar to that described in Example 1.
LC/MS $(M+1)^+$: 413.1.

EXAMPLE 6

Compound 6 was prepared in a manner similar to that described in Example 1.
LC/MS $(M+1)^+$: 455.0.

EXAMPLE 7

Compound 7 was prepared in a manner similar to that described in Example 1.
LC/MS $(M+1)^+$: 431.1.

EXAMPLE 8

Compound 8 was prepared in a manner similar to that described in Example 1.
LC/MS $(M+1)^+$: 459.0.

EXAMPLE 9

Compound 9 was prepared in a manner similar to that described in Example 1.
LC/MS (M+1)$^+$: 461.2.

EXAMPLE 10

Compound 10 was prepared in a manner similar to that described in Example 1.
LC/MS (M+1)$^+$: 447.2.

EXAMPLE 11

Compound 11 was prepared in a manner similar to that described in Example 1.
LC/MS (M+1)$^+$: 611.2.

EXAMPLE 12

Compound 12 was prepared in a manner similar to that described in Example 1.
LC/MS (M+1)$^+$: 597.2.

EXAMPLE 13

Compound 13 was prepared in a manner similar to that described in Example 1.
LC/MS (M+1)$^+$: 583.2.

EXAMPLE 14

Compound 14 was prepared in a manner similar to that described in Example 1.
LC/MS (M+1)$^+$: 569.2.

EXAMPLE 15

Compound 15 was prepared in a manner similar to that described in Example 1.
LC/MS (M+1)$^+$: 463.1.

EXAMPLE 16

Compound 16 was prepared in a manner similar to that described in Example 1.
LC/MS (M+1)$^+$: 477.1.

EXAMPLE 17

Compound 17 was prepared in a manner similar to that described in Example 1.
LC/MS (M+1)$^+$: 491.1.

EXAMPLE 18

Compound 18 was prepared in a manner similar to that described in Example 1.
LC/MS (M+1)$^+$: 435.1.

EXAMPLE 19

Compound 19 was prepared in a manner similar to that described in Example 1.
LC/MS (M+1)$^+$: 466.9.

EXAMPLE 20

Compound 20 was prepared in a manner similar to that described in Example 1.
LC/MS (M+1)$^+$: 556.8.

EXAMPLE 21

Compound 21 was prepared in a manner similar to that described in Example 1.
LC/MS (M+1)$^+$: 481.2.

EXAMPLE 22

Compound 22 was prepared in a manner similar to that described in Example 1.
LC/MS (M+1)$^+$: 511.3.

EXAMPLE 23

Compound 23 was prepared in a manner similar to that described in Example 1.
LC/MS (M+1)$^+$: 736.8.

EXAMPLE 24

Compound 24 was prepared in a manner similar to that described in Example 1.
LC/MS (M+1)$^+$: 615.0.

EXAMPLE 25

Compound 25 was prepared in a manner similar to that described in Example 1.
LC/MS (M+1)$^+$: 479.2.

EXAMPLE 26

Compound 26 was prepared in a manner similar to that described in Example 1.
LC/MS (M+1)$^+$: 493.1.

EXAMPLE 27

Compound 27 was prepared in a manner similar to that described in Example 1.
LC/MS (M+1)$^+$: 507.3.

EXAMPLE 28

Compound 28 was prepared in a manner similar to that described in Example 1.
LC/MS (M+1)$^+$: 507.1.

EXAMPLE 29

Compound 29 was prepared in a manner similar to that described in Example 1.
LC/MS (M+1)$^+$: 599.1.

EXAMPLE 30

Compound 30 was prepared in a manner similar to that described in Example 1.
LC/MS (M+1)$^+$: 469.0.

EXAMPLE 31

Compound 31 was prepared in a manner similar to that described in Example 1.
LC/MS (M+1)$^+$: 463.1.

EXAMPLE 32

Compound 32 was prepared in a manner similar to that described in Example 1.
LC/MS (M+1)$^+$: 384.9.

EXAMPLE 33

Compound 33 was prepared in a manner similar to that described in Example 1.
LC/MS (M+1)$^+$: 447.2.

EXAMPLE 34

Compound 34 was prepared in a manner similar to that described in Example 1.
LC/MS (M+1)$^+$: 419.1.

EXAMPLE 35

Compound 35 was prepared in a manner similar to that described in Example 1.
LC/MS (M+1)$^+$: 469.2.

EXAMPLE 36

Compound 36 was prepared in a manner similar to that described in Example 1.
LC/MS (M+1)$^+$: 471.2.

EXAMPLE 37

Compound 37 was prepared in a manner similar to that described in Example 1.
LC/MS (M+1)$^+$: 562.0.

EXAMPLE 38

Compound 38 was prepared in a manner similar to that described in Example 1.
LC/MS (M+1)$^+$: 523.0.

EXAMPLE 39

Compound 39 was prepared in a manner similar to that described in Example 1.
LC/MS (M+1)$^+$: 559.2.

EXAMPLE 40

Compound 40 was prepared in a manner similar to that described in Example 1.
LC/MS (M+1)$^+$: 414.2.

EXAMPLE 41

Compound 41 was prepared in a manner similar to that described in Example 1.
LC/MS (M+1)$^+$: 584.0.

EXAMPLE 42

Compound 42 was prepared in a manner similar to that described in Example 1.
LC/MS (M+1)$^+$: 554.0.

EXAMPLE 43

Compound 43 was prepared in a manner similar to that described in Example 1.
LC/MS (M+1)$^+$: 568.0.

EXAMPLE 44

Compound 44 was prepared in a manner similar to that described in Example 1.
LC/MS (M+1)$^+$: 633.9.

EXAMPLE 45

Compound 45 was prepared in a manner similar to that described in Example 1.
LC/MS (M+1)$^+$: 431.2.

EXAMPLE 46

Compound 46 was prepared in a manner similar to that described in Example 1.
LC/MS (M+1)$^+$: 563.1.

EXAMPLE 47

Compound 47 was prepared in a manner similar to that described in Example 1.
LC/MS (M+1)$^+$: 652.8.

EXAMPLE 48

Compound 48 was prepared in a manner similar to that described in Example 1.
LC/MS (M+1)$^+$: 454.0.

EXAMPLE 49

Compound 57 was prepared in a manner similar to that described in Example 1.
LC/MS (M+1)$^+$: 598.1.

EXAMPLE 50

Compound 50 was prepared in a manner similar to that described in Example 1.
LC/MS (M+1)$^+$: 611.9.

EXAMPLE 51

Compound 51 was prepared in a manner similar to that described in Example 1.
LC/MS (M+1)$^+$: 623.9.

EXAMPLE 52

Compound 52 was prepared in a manner similar to that described in Example 1.
LC/MS (M+1)$^+$: 634.0.

EXAMPLE 53

Compound 53 was prepared following the procedures described below:

4-Chloro-2,6-dimethyl-quinoline (1.9 g, 10 mmol) obtained in Example 1 and 1,6-hexadiamine (2.3 g, 20 mmol) were dissolved in pentanol (40 mL). The solution was kept under reflux over night. After cooling down to room temperature, 0.5 N NaOH (5 mL) was added to the reaction mixture. The reaction mixture was stirred at room temperature for 30 minutes and then extracted with $CH_2Cl_2$ (10 mL×3). The organic layer was separated, dried over magnesium sulfate, and concentrated under reduced pressure. The crude product was purified by column chromatography (2% $Et_3N$ in 1:2 n-hexane and ethyl acetate) to give N1-(2,6-dimethyl-quinolin-4-yl)-hexane-1,5-diamine (1.9 g, 70% yield).

N1-(2,6-Dimethyl-quinolin-4-yl)-hexane-1,5-diamine (271 mg, 1.0 mmol) thus obtained, 4-chloro-6-methoxy-2-methyl-quinoline (228 mg, 1.1 mmol) (obtained following the procedure described in Example 1), and sodium iodide (catalytic amount) were added in pentanol (10 mL). The reaction mixture was kept under reflux over night. After cooling down to room temperature, 0.5 N NaOH (5 mL) was added to the reaction mixture. The reaction was stirred at room temperature for another 30 minutes and then extracted with $CH_2Cl_2$ (10 mL×3). The organic layer was separated, dried over magnesium sulfate, and concentrated under reduced pressure. The product was purified by column chromatography (2% $Et_3N$ in 1:1 n-hexane and ethyl acetate) to give compound 53.

LC/MS $(M+1)^+$: 430.2.

EXAMPLE 54

Compound 54 was prepared in a manner similar to that described in Example 53.
LC/MS $(M+1)^+$: 519.2.

EXAMPLE 55

Compound 55 was prepared in a manner similar to that described in Example 53.
LC/MS $(M+1)^+$: 427.2.

EXAMPLE 56

Compound 56 was prepared in a manner similar to that described in Example 53.
LC/MS $(M+1)^+$: 467.2.

EXAMPLE 57

Compound 57 was prepared in a manner similar to that described in Example 53.
LC/MS $(M+1)^+$: 453.2.

EXAMPLE 58

Compound 58 was prepared in a manner similar to that described in Example 53.
LC/MS $(M+1)^+$: 467.2.

EXAMPLE 59

Compound 59 was prepared in a manner similar to that described in Example 53.
LC/MS $(M+1)^+$: 615.0.

EXAMPLE 60

Compound 60 was prepared in a manner similar to that described in Example 53.
LC/MS $(M+1)^+$: 543.2.

EXAMPLE 61

Compound 61 was prepared in a manner similar to that described in Example 53.
LC/MS $(M+1)^+$: 537.2.

EXAMPLE 62

Compound 62 was prepared in a manner similar to that described in Example 53.
LC/MS $(M+1)^+$: 546.2.

EXAMPLE 63

Compound 63 was prepared in a manner similar to that described in Example 53.
LC/MS $(M+1)^+$: 635.2.

EXAMPLE 64

Compound 64 was prepared following the procedures described below:

4-Chloro-2,6-dimethyl-quinoline (191 mg, 1.0 mmol) obtained in Example 1 and 4-amino-N-thiazol-2-yl-benzenesulfonamide (280 mg, 1.1 mmol) were dissolved in pentanol (5 mL). The solution was kept under reflux over night. After cooling down to room temperature, 0.5 N NaOH (5 mL) was added to the reaction solution. The reaction mixture was stirred at room temperature for another 30 minutes and then extracted with $CH_2Cl_2$ (10 mL×3). The organic layer was separated, dried over magnesium sulfate, and concentrated under reduced pressure. The crude product was purified by column chromatography (2% $Et_3N$ in ratio 1:1 n-hexane and ethyl acetate) to give compound 64 (328 mg, 80% yield).

LC/MS $(M+1)^+$: 410.8.

EXAMPLE 65

Compound 65 was prepared following the procedures described in the first paragraph of Example 53.
LC/MS $(M+1)^+$: 272.0.

EXAMPLE 66

Compound 66 was prepared in a manner similar to that described in the first paragraph of Example 53.
LC/MS $(M+1)^+$: 258.2.

EXAMPLE 67

Compound 67 was prepared in a manner similar to that described in Example 64.
LC/MS $(M+1)^+$: 316.1.

EXAMPLE 68

Compound 68 was prepared following the procedures described below:

Pyridine-2-carbaldehyde (210 mg, 1.1 mmol), {2-[2-(2-amino-phenyl)-ethyl]-phenyl}-(2,6-dimethyl-quinolin-4- yl)-amine (367 mg, 1.0 mmol) (This compound was prepared in a manner similar to that described in step 1 of Example 53.), and 10 wt % Pd/C (catalytic amount) were dissolved in MeOH (20 mL). The reaction mixture was kept under pressure (60 psi) with $H_2$ over night. After releasing the pressure, the reaction mixture was filtered and concentrated. The crude product was purified by column chromatography (2% $Et_3N$ in 1:1 n-hexane and ethyl acetate) to give compound 68 (459 mg, 85% yield).

LC/MS $(M+1)^+$: 459.0.

EXAMPLE 69

Compound 69 was prepared in a manner similar to that described in the first paragraph of Example 53.

LC/MS $(M+1)^+$: 460.1.

EXAMPLE 70

Compound 70 was prepared in a manner similar to that described in Example 68.

LC/MS $(M+1)^+$: 551.2.

EXAMPLE 71

Compound 71 was prepared in a manner similar to that described in the first paragraph of Example 53.

LC/MS $(M+1)^+$: 387.1.

EXAMPLE 72

Compound 72 was prepared in a manner similar to that described in the first paragraph of Example 53.

LC/MS $(M+1)^+$: 298.2.

EXAMPLE 73

Compound 73 was prepared in a manner similar to that described in Example 53.

LC/MS $(M+1)^+$: 443.2.

EXAMPLE 74

Compound 74 was prepared in a manner similar to that described in Example 1.

LC/MS $(M+1)^+$: 651.1.

EXAMPLE 75

Compound 75 was prepared in a manner similar to that described in Example 1.

LC/MS $(M+1)^+$: 535.1.

EXAMPLE 76

Compound 76 was prepared in a manner similar to that described in Example 1.

LC/MS $(M+1)^+$: 479.3.

EXAMPLE 77

Compound 77 was prepared in a manner similar to that described in Example 1.

LC/MS $(M+1)^+$: 563.4.

EXAMPLE 78

Compound 78 was prepared in a manner similar to that described in Example 1.

LC/MS $(M+1)^+$: 495.3.

EXAMPLE 79

Compound 79 was prepared in a manner similar to that described in Example 1.

LC/MS $(M+1)^+$: 572.2.

EXAMPLE 80

Compound 80 was prepared in a manner similar to that described in Example 1.

LC/MS $(M+1)^+$: 598.3.

EXAMPLE 81

Compound 81 was prepared in a manner similar to that described in Example 1.

LC/MS $(M+1)^+$: 638.1.

EXAMPLE 82

Compound 82 was prepared in a manner similar to that described in Example 1.

LC/MS $(M+1)^+$: 756.1.

EXAMPLE 83

Compound 83 was prepared in a manner similar to that described in Example 1.

LC/MS $(M+1)^+$: 630.2.

EXAMPLE 84

Compound 84 was prepared in a manner similar to that described in Example 1.

LC/MS $(M+1)^+$: 634.2.

EXAMPLE 85

Compound 85 was prepared in a manner similar to that described in Example 1.

LC/MS $(M+1)^+$: 546.1.

EXAMPLE 86

Compound 86 was prepared in a manner similar to that described in Example 1.

LC/MS $(M+1)^+$: 614.1.

EXAMPLE 87

Compound 87 was prepared in a manner similar to that described in Example 1.

LC/MS $(M+1)^+$: 612.2.

EXAMPLE 88

Compound 88 was prepared in a manner similar to that described in Example 1.

LC/MS $(M+1)^+$: 652.1.

EXAMPLE 89

Compound 89 was prepared in a manner similar to that described in Example 1.
LC/MS (M+1)$^+$: 692.3.

EXAMPLE 90

Compound 90 was prepared in a manner similar to that described in Example 1.
LC/MS (M+1)$^+$: 702.0.

EXAMPLE 91

Compound 91 was prepared in a manner similar to that described in Example 1.
LC/MS (M+1)$^+$: 616.2.

EXAMPLE 92

Compound 92 was prepared in a manner similar to that described in Example 1.
LC/MS (M+1)$^+$: 560.2.

EXAMPLE 93

Compound 93 was prepared in a manner similar to that described in Example 1.
LC/MS (M+1)$^+$: 600.3.

EXAMPLE 94

Compound 94 was prepared in a manner similar to that described in Example 1.
LC/MS (M+1)$^+$: 588.2.

EXAMPLE 95

Compound 95 was prepared in a manner similar to that described in Example 1.
LC/MS (M+1)$^+$: 666.2.

EXAMPLE 96

Compound 96 was prepared in a manner similar to that described in Example 1.
LC/MS (M+1)$^+$: 574.2.

EXAMPLE 97

Compound 97 was prepared in a manner similar to that described in the first paragraph of Example 53, the intermediate thus obtained was then treated with biphenylacetyl chloride and worked up following the procedures described in Example 68.
LC/MS (M+1)$^+$: 528.1.

EXAMPLE 98

Compound 98 was prepared in a manner similar to that described in Example 53.
LC/MS (M+1)$^+$: 502.1.

EXAMPLE 99

Compound 99 was prepared in a manner similar to that described in Example 53.
LC/MS (M+1)$^+$: 508.5.

EXAMPLE 100

Compound 100 was prepared in a manner similar to that described in Example 53.
LC/MS (M+1)$^+$: 629.3.

EXAMPLE 101

Compound 101 was prepared in a manner similar to that described in Example 53.
LC/MS (M+1)$^+$: 636.2.

EXAMPLE 102

Compound 102 was prepared in a manner similar to that described in Example 53.
LC/MS (M+1)$^+$: 674.1.

EXAMPLE 103

Compound 103 was prepared in a manner similar to that described in Example 53.
LC/MS (M+1)$^+$: 622.2.

EXAMPLE 104

Compound 104 was prepared in a manner similar to that described in Example 53.
LC/MS (M+1)$^+$: 636.2.

EXAMPLE 105

Compound 105 was prepared in a manner similar to that described in Example 53.
LC/MS (M+1)$^+$: 650.2.

EXAMPLE 106

Compound 106 was prepared in a manner similar to that described in Example 53.
LC/MS (M+1)$^+$: 688.1.

EXAMPLE 107

Compound 107 was prepared in a manner similar to that described in Example 53.
LC/MS (M+1)$^+$: 692.2.

EXAMPLE 108

Compound 108 was prepared in a manner similar to that described in Example 53.
LC/MS (M+1)$^+$: 686.2.

EXAMPLE 109

Compound 109 was prepared in a manner similar to that described in Example 53.
LC/MS (M+1)$^+$: 580.2.

EXAMPLE 110

Compound 110 was prepared following the procedures described below:
Compound 26 (160 mg) and methyl iodide (460 mg) were added in 3 mL of THF and the mixture was refluxed for 3 hours. The precipitate thus obtained was collected by filtration, washed with ether, and dried to give the desired product.

LC/MS (M−1)$^+$: 520.2.

EXAMPLE 111

Compound 111 was prepared in a manner similar to that described in Example 110.

LC/MS (M−1)$^+$: 455.7.

EXAMPLE 112

Compound 112 was prepared in a manner similar to that described in Example 110.

LC/MS (M−1)$^+$: 550.2.

EXAMPLE 113

Compound 113 was prepared in a manner similar to that described in Example 110.

LC/MS (M−1)$^+$: 579.3.

EXAMPLE 114

Compound 114 was prepared in a manner similar to that described in Example 110.

LC/MS (M−1)$^+$: 523.3.

EXAMPLE 115

Compound 115 was prepared in a manner similar to that described in Example 110.

LC/MS (M−1)$^+$: 662.2.

EXAMPLE 116

Compound 116 was prepared in a manner similar to that described in Example 110.

LC/MS (M−1)$^+$: 666.2.

EXAMPLE 117

Compound 117 was prepared in a manner similar to that described in Example 110.

LC/MS (M−1)$^+$: 640.3.

EXAMPLE 118

Compound 118 was prepared in a manner similar to that described in Example 110.

LC/MS (M−1)$^+$: 680.2.

EXAMPLE 119

Compound 119 was prepared in a manner similar to that described in Example 110.

LC/MS (M−1)$^+$: 720.4.

EXAMPLE 120

Compound 120 was prepared in a manner similar to that described in Example 110.

LC/MS (M−1)$^+$: 588.2.

EXAMPLE 121

Compound 121 was prepared in a manner similar to that described in Example 110.

LC/MS (M−1)$^+$: 644.3.

EXAMPLE 122

Compound 122 was prepared in a manner similar to that described in Example 110.

LC/MS (M−1)$^+$: 616.2.

EXAMPLE 123

Compound 123 was prepared following the procedures described below:

Compound 54 (160 mg) was added in 5 mL of 2-iodoethanol and the solution was refluxed for 3 hours. The precipitate thus formed was collected by filtration, washed with ether, and dried to give the desired product.

LC/MS (M−1)$^+$: 607.8.

EXAMPLE 124

Compound 124 was prepared in a manner similar to that described in Example 123.

LC/MS (M−1)$^+$: 547.8.

EXAMPLE 125

Compound 125 was prepared in a manner similar to that described in Example 123.

LC/MS (M−1)$^+$: 664.2.

EXAMPLE 126

Compound 126 was prepared in a manner similar to that described in Example 123.

LC/MS (M−1)$^+$: 678.2.

EXAMPLE 127

Compound 127 was prepared in a manner similar to that described in Example 123.

LC/MS (M−1)$^+$: 702.1.

EXAMPLE 128

Compound 128 was prepared in a manner similar to that described in Example 123.

LC/MS (M−1)$^+$: 720.2.

EXAMPLE 129

Compound 129 was prepared in a manner similar to that described in Example 123.

LC/MS (M−1)$^+$: 714.3.

EXAMPLE 130

Compound 130 was prepared following the procedures described below:

Methyl iodide (3 mL) and 4,6-dichloro-2-methylquinoline (2 g) were heated in CH$_3$CN at 65° C. for 40 hours. The precipitate thus formed was collected by filtration, washed with ether, and dried by nitrogen flow and by vacuum to give a quaternary quinolinium salt (2.1 g).

Compound 81 (92.8 mg) and quinolinium salt (70.9 mg) obtained above were added in 3 mL of $CH_3CN$. The mixture was refluxed for 12 hours. The precipitation thus obtained was collected by filtration, washed with ether, and dried to give the desired product.

LC/MS $(M)^+$: 652.2.

EXAMPLE 131

Compound 131 was prepared in a manner similar to that described in Example 130.

LC/MS $(M)^+$: 515.

EXAMPLE 132

Compound 132 was prepared in a manner similar to that described in Example 130.

LC/MS $(M)^+$: 481.2.

EXAMPLE 133

Compound 133 was prepared in a manner similar to that described in Example 130.

LC/MS $(M)^+$: 521.2.

EXAMPLE 134

Compound 134 was prepared in a manner similar to that described in Example 130.

LC/MS $(M)^+$: 521.2.

EXAMPLE 135

Compound 135 was prepared in a manner similar to that described in Example 1.

LC/MS $(M+1)^+$: 643.

EXAMPLE 136

Compound 136 was prepared in a manner similar to that described in Example 1.

LC/MS $(M+1)^+$: 691.

EXAMPLE 137

Compound 137 was prepared in a manner similar to that described in Example 1.

LC/MS $(M+1)^+$: 612.

EXAMPLE 138

Compound 138 was prepared in a manner similar to that described in Example 1.

LC/MS $(M+1)^+$: 642.

EXAMPLE 139

Compound 139 was prepared in a manner similar to that described in Example 1.

LC/MS $(M+1)^+$: 642.

EXAMPLE 140

Compound 140 was prepared in a manner similar to that described in Example 1.

LC/MS $(M+1)^+$: 682.

EXAMPLE 141

Compound 141 was prepared in a manner similar to that described in Example 1.

LC/MS $(M+1)^+$: 642.

EXAMPLE 142

Compound 142 was prepared in a manner similar to that described in Example 1.

LC/MS $(M+1)^+$: 662.8.

EXAMPLE 143

Compound 143 was prepared in a manner similar to that described in Example 1.

LC/MS $(M+1)^+$: 704.7.

EXAMPLE 144

Compound 144 was prepared in a manner similar to that described in Example 1.

LC/MS $(M+1)^+$: 667.5.

EXAMPLE 145

Compound 145 was prepared in a manner similar to that described in Example 1.

LC/MS $(M+1)^+$: 738.4.

EXAMPLE 146

Compound 146 was prepared in a manner similar to that described in Example 53.

LC/MS $(M+1)^+$: 673.1.

EXAMPLE 147

Compound 147 was prepared in a manner similar to that described in Example 53.

LC/MS $(M+1)^+$: 665.0.

EXAMPLE 148

Compound 148 was prepared in a manner similar to that described in Example 53.

LC/MS $(M+1)^+$: 657.4.

EXAMPLE 149

Compound 149 was prepared in a manner similar to that described in Example 53.

LC/MS $(M+1)^+$: 625.4.

EXAMPLE 150

Compound 150 was prepared in a manner similar to that described in Example 53.

LC/MS $(M+1)^+$: 635.1.

EXAMPLE 151

Compound 151 was prepared in a manner similar to that described in Example 1.

LC/MS $(M+1)^+$: 653.4.

EXAMPLE 152

Compound 152 was prepared in a manner similar to that described in Example 1.
LC/MS (M+1)$^+$: 720.8.

EXAMPLE 153

Compound 153 was prepared in a manner similar to that described in Example 1.
LC/MS (M+1)$^+$: 682.6.

EXAMPLE 154

Compound 154 was prepared in a manner similar to that described in Example 1.
LC/MS (M+1)$^+$: 656.6.

EXAMPLE 155

Compound 155 was prepared in a manner similar to that described in Example 1.
LC/MS (M+1)$^+$: 672.4.

EXAMPLE 156

Compound 156 was prepared in a manner similar to that described in Example 53.
LC/MS (M+1)$^+$: 725.6.

EXAMPLE 157

Compound 157 was prepared in a manner similar to that described in Example 1.
LC/MS (M+1)$^+$: 801.4.

EXAMPLE 158

Compound 158 was prepared following the procedures described below:
A mixture of 3-[[2-(6-chloro-2-methyl-quinolin-4-ylamino)-ethyl]-(4-methoxy-benzenesulfonyl)-amino]-propionic acid (100 mg) (This compound was prepared in a manner similar to that described in step 1 of Example 53.) and 1-[3-(dimethylamino)-propyl]-3-ethylcarbodiimide hydrochloride (80 mg) was stirred in DMF (2 mL) for 30 minutes at room temperature, followed by addition of 4-amino-N-(2,6-dimethyl-pyrimidin-4-yl)-benzenesulfonamide (64 mg). The reaction mixture was stirred for 3 hours, and then the solvent was evaporated under vacuum. The residue was then quenched with $H_2O$ (2 mL) and extracted with $CHCl_3$ (10 mL). The combined extract was dried with $MgSO_4$, concentrated under vacuum, and purified by column chromatography to give compound 158.
LC/MS (M+1)$^+$: 737.8.

EXAMPLE 159

Compound 159 was prepared in a manner similar to that described in Example 158.
LC/MS (M+1)$^+$: 595.8.

EXAMPLE 160

Compound 160 was prepared in a manner similar to that described in Example 158.
LC/MS (M+1)$^+$: 637.8.

EXAMPLE 161

Compound 161 was prepared in a manner similar to that described in Example 158.
LC/MS (M+1)$^+$: 553.9.

EXAMPLE 162

Compound 162 was prepared in a manner similar to that described in Example 158.
LC/MS (M+1)$^+$: 610.9.

EXAMPLE 163

Compound 163 was prepared in a manner similar to that described in Example 158.
LC/MS (M+1)$^+$: 660.1.

EXAMPLE 164

Compound 164 was prepared in a manner similar to that described in Example 158.
LC/MS (M+1)$^+$: 568.9.

EXAMPLE 165

Compound 165 was prepared in a manner similar to that described in Example 158.
LC/MS (M+1)$^+$: 552.9.

EXAMPLE 166

Compound 166 was prepared in a manner similar to that described in Example 158.
LC/MS (M+1)$^+$: 609.1.

EXAMPLE 167

Compound 167 was prepared in a manner similar to that described in Example 158.
LC/MS (M+1)$^+$: 597.1.

EXAMPLE 168

Compound 168 was prepared in a manner similar to that described in Example 158.
LC/MS (M+1)$^+$: 568.9.

EXAMPLE 169

Compound 169 was prepared in a manner similar to that described in Example 158.
LC/MS (M+1)$^+$: 594.9.

EXAMPLE 170

Compound 170 was prepared in a manner similar to that described in Example 158.
LC/MS (M+1)$^+$: 584.1.

EXAMPLE 171

Compound 171 was prepared in a manner similar to that described in Example 68.
LC/MS (M+1)$^+$: 604.1.

EXAMPLE 172

Compound 172 was prepared in a manner similar to that described in Example 158.
LC/MS (M+1)+: 604.0.

EXAMPLE 173

Compound 173 was prepared in a manner similar to that described in Example 158.
LC/MS (M+1)+: 568.1.

EXAMPLE 174

Compound 174 was prepared in a manner similar to that described in Example 158.
LC/MS (M+1)+: 568.0.

EXAMPLE 175

Compound 175 was prepared in a manner similar to that described in Example 158.
LC/MS (M+1)+: 582.9.

EXAMPLE 176

Compound 176 was prepared in a manner similar to that described in Example 158.
LC/MS (M+1)+: 644.9.

EXAMPLE 177

Compound 177 was prepared in a manner similar to that described in Example 158.
LC/MS (M+1)+: 603.9.

EXAMPLE 178

Compound 178 was prepared in a manner similar to that described in Example 158.
LC/MS (M+1)+: 583.9.

EXAMPLE 179

Compound 179 was prepared in a manner similar to that described in Example 158.
LC/MS (M+1)+: 568.9.

EXAMPLE 180

Compound 180 was prepared in a manner similar to that described in Example 158.
LC/MS (M+1)+: 554.1.

EXAMPLE 181

Compound 181 was prepared in a manner similar to that described in Example 158.
LC/MS (M+1)+: 569.1.

EXAMPLE 182

Compound 182 was prepared in a manner similar to that described in Example 158.
LC/MS (M+1)+: 599.1.

EXAMPLE 183

Compound 183 was prepared in a manner similar to that described in Example 158.
LC/MS (M+1)+: 559.1.

EXAMPLE 184

Compound 184 was prepared in a manner similar to that described in Example 158.
LC/MS (M+1)+: 620.1.

EXAMPLE 185

Compound 185 was prepared in a manner similar to that described in Example 158.
LC/MS (M+1)+: 604.1.

EXAMPLE 186

Compound 186 was prepared in a manner similar to that described in Example 158.
LC/MS (M+1)+: 603.9.

EXAMPLE 187

Compound 187 was prepared in a manner similar to that described in Example 158.
LC/MS (M+1)+: 570.9.

EXAMPLE 188

Compound 188 was prepared in a manner similar to that described in Example 158.
LC/MS (M+1)+: 601.9.

EXAMPLE 189

Compound 189 was prepared in a manner similar to that described in Example 158.
LC/MS (M+1)+: 613.1.

EXAMPLE 190

Compound 190 was prepared in a manner similar to that described in Example 158.
LC/MS (M+1)+: 682.1.

EXAMPLE 191

Compounds 1–190 were tested for their efficacy in blocking activation of CXCR3 using a DELFIA GTP-binding kit (Wallac Oy, Turku, Finland). The DELFIA GTP-binding assay is a time-resolved fluorometric assay based on GDP-GTP exchange on G-protein subunits followed by activation of a G protein-coupled receptor by its agonists. Eu-GTP, obtained from Wallac Oy, was used in this assay to allow monitoring of agonist-dependent activation of G-protein. Stimulation of CXCR3 by interferon-α inducible protein 10 (IP-10) leads to the replacement of GDP by GTP on the α-subunit of G-protein. This GTP-Gα complex represents the activated form of G-protein. Eu-GTP, a non-hydrolysable analog of GTP, can be used to quantify the amount of activated G-protein. (Peltonen et al., Eur. J. Pharmacol. (1998) 355:275.)

Plasma membrane of CXCR3-expressing HEK293 cells was suspended in an assay buffer (50 mM NaCl, 100 µg/mL saponin, 3 mM $MgCl_2$, 3 µM GDP, 5% BSA, 50 mM HEPES, pH 7.4). An aliquot (4 µg protein) was added to each well of an AcroPlate (Pall Life Sciences, Ann Arbor, Mich.). After the addition of the test compounds (10 µM in 0.1% DMSO) and IP-10 (4 nM in the assay buffer), the assay plate was incubated in the dark at room temperature with slow shaking for 10 minutes. Eu-GTP was added to each well and the plate was incubated again for 60 minutes. The assay was terminated by washing the plate twice with a wash solution provided in the assay kit. Binding of Eu-GTP was determined based on the fluorescence signal from a Victor 2 multi-label reader.

Unexpectedly, 92 compounds showed $IC_{50}$ values lower than 1 µM, 33 compounds showed $IC_{50}$ values between 1 µM and 5 µM, and 30 compounds showed $IC_{50}$ values between 5 µM and 10 µM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

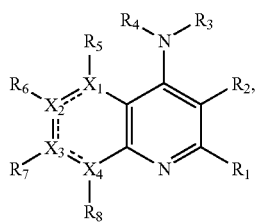

(I)

wherein
each ==== is a single bond or a double bond; provided that if one ==== is a double bond, its neighboring ==== is not a double bond;
each of ====$X_1$—, ====$X_2$—, ====$X_3$—, and ====$X_4$—, independently, is —C=, —$CR_a$—, —N=, —N—, —S—, —O—, or a single bond; at most one of ====$X_1$—, ====$X_2$—, ====$X_3$—, and ====$X_4$— being a single bond and at most two of ====$X_1$—, ====$X_2$—, ====$X_3$—, and ====$X_4$— being —N=, —N—, —S—, or —O—;
each of $R_1$ and $R_2$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $C_1$–$C_6$ alkylamino, $C_1$–$C_{12}$ dialkylamino, arylamino, diarylamino, —C(O)—$NR_bR_b'$, —OC(O)—$R_b$, —C(O)—$R_b$, or halogen; or $R_1$ and $R_2$ together are $C_5$–$C_8$ heterocycloalkyl;
each of $R_3$ and $R_4$, independently, is H or -A-N(B)-D; at most one of $R_3$ and $R_4$ being H; and
each of $R_5$, $R_6$, $R_7$, and $R_8$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, $NH_2$, $NO_2$, CN, $C_1$–$C_6$ alkylamino, $C_1$–$C_{12}$ dialkylamino, arylamino, diarylamino, —C(O)—$NR_cR_c'$, —C(O)—$OR_c$, —OC(O)—$R_c$, —C(O)—$R_c$, halogen, or deleted; or $R_5$ and $R_6$ together are $C_5$–$C_7$ cycloalkyl or $C_5$–$C_7$ heterocycloalkyl; or $R_6$ and $R_7$ together are $C_5$–$C_7$ cycloalkyl or $C_5$–$C_7$ heterocycloalkyl; or $R_7$ and $R_8$ together are $C_5$–$C_7$ cycloalkyl or $C_5$–$C_7$ heterocycloalkyl; provided that if $R_5$ is deleted, ====$X_1$— is —N=, —S—, —O—, or a single bond; if $R_6$ is deleted, ====$X_2$— is —N=, —S—, —O—, or a single bond; if $R_7$ is deleted, ====$X_3$— is —N=, —S—, —O—, or a single bond; and if $R_8$ is deleted, ====$X_4$— is —N=, —S—, —O—, or a single bond;
in which A is $C_1$–$C_{12}$ alkyl optionally containing 1–6 heteroatoms and substituted with sulfonyl, $C_1$–$C_6$ alkylsulfonyl, arylsulfonyl, or heteroarylsulfonyl, $C_2$–$C_{12}$ alkenyl optionally containing 1–6 heteroatoms, $C_2$–$C_{12}$ alkynyl optionally containing 1–6 heteroatoms, aryl, heteroaryl, $C_1$–$C_{10}$ alkylsulfonyl, arylsulfonyl, $C_1$–$C_{10}$ alkylcarbonyl containing 1–6 heteroatoms, $C_2$–$C_{20}$ alkylaryl optionally containing 1–6 heteroatoms, $C_2$–$C_{20}$ arylalkyl optionally containing 1–6 heteroatoms, $C_2$–$C_{20}$ alkylheteroaryl containing 1–6 heteroatoms, or $C_2$–$C_{20}$ heteroarylalkyl containing 2–6 heteroatoms; B is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, or heteroaryl; or B and A together are heteroaryl; and D is H, aryl, heteroaryl, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, —C(O)—$R_d$, —$SO_2$—$R_d$, —C(S)—$R_d$, —C(O)—$NR_dR_d'$, —C(O)—$OR_d$, —OC(O)—$R_d$, —C(O)—$SR_d$, or —SC(O)—$R_d$; or D and A together are heteroaryl; each of $R_a$, $R_b$, $R_b'$, $R_c$, $R_c'$, $R_d$, and $R_d'$, independently, being H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, or heteroaryl; or $R_d$ and $R_d'$ together being $C_5$–$C_7$ heterocycloalkyl;
or a salt thereof.

2. The compound of claim 1, wherein D is of formula (II),

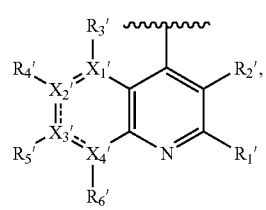

(II)

wherein
each ==== is a single bond or a double bond; provided that if one ==== is a double bond, its neighboring ==== is not a double bond;

each of ====X$_1$'—, ====X$_2$'—, ====X$_3$'—, and ====X$_4$'—, independently, is —C=, —CR$_e$—, —N=, —N—, —S—, —O—, or a single bond; at most one of ====X$_1$'—, ====X$_2$'—, ====X$_3$'—, and ====X$_4$'—, being a single bond, and at most two of ====X$_1$'—, ====X$_2$'—, ====X$_3$'—, and ====X$_4$'—, being —N=, —N—, —S—, or —O—;

each of R$_1$' and R$_2$', independently, is H, C$_1$–C$_8$ alkyl, C$_2$–C$_8$ alkenyl, C$_2$–C$_8$ alkynyl, C$_3$–C$_8$ cycloalkyl, C$_5$–C$_8$ cycloalkenyl, C$_3$–C$_8$ heterocycloalkyl, C$_5$–C$_8$ heterocycloalkenyl, aryl, heteroaryl, OH, C$_1$–C$_6$ alkoxy, aryloxy, heteroaryloxy, C$_1$–C$_6$ alkylthio, arylthio, NH$_2$, C$_1$–C$_6$ alkylamino, C$_1$–C$_{12}$ dialkylamino, arylamino, diarylamino, —C(O)—NR$_f$R$_f$', —OC(O)—R$_f$, —C(O)—R$_f$, or halogen; or R$_1$' and R$_2$' together are C$_5$–C$_8$ cycloalkyl or C$_5$–C$_8$ heterocycloalkyl;

each of R$_3$', R$_4$', R$_5$', and R$_6$', independently, is H, C$_1$–C$_8$ alkyl, C$_2$–C$_8$ alkenyl, C$_2$–C$_8$ alkynyl, C$_3$–C$_8$ cycloalkyl, C$_5$–C$_8$ cycloalkenyl, C$_3$–C$_8$ heterocycloalkyl, C$_5$–C$_8$ heterocycloalkenyl, aryl, heteroaryl, OH, C$_1$–C$_6$ alkoxy, aryloxy, heteroaryloxy, C$_1$–C$_6$ alkylthio, arylthio, NH$_2$, NO$_2$, CN, C$_1$–C$_6$ alkylamino, C$_1$–C$_{12}$ dialkylamino, arylamino, diarylamino, —C(O)—NR$_g$R$_g$', —C(O)—OR$_g$, —OC(O)—R$_g$, —C(O)—R$_g$, halogen, or deleted; or R$_3$' and R$_4$' together are C$_5$–C$_7$ cycloalkyl or C$_5$–C$_7$ heterocycloalkyl; or R$_4$' and R$_5$' together are C$_5$–C$_7$ cycloalkyl or C$_5$–C$_7$ heterocycloalkyl; or R$_5$' and R$_6$' together are C$_5$–C$_7$ cycloalkyl or C$_5$–C$_7$ heterocycloalkyl; provided that if R$_3$' is deleted, ====X$_1$'— is —N=, —S—, —O—, or a single bond; if R$_4$' is deleted, ====X$_2$'— is —N=, —S—, —O—, or a single bond; if R$_5$' is deleted, ====X$_3$'— is —N=, —S—, —O—, or a single bond; and if R$_6$' is deleted, ====X$_4$'— is —N=, —S—, —O—, or a single bond;

in which each of R$_e$, R$_f$, R$_f$', R$_g$, and R$_g$', independently, being H, C$_1$–C$_8$ alkyl, C$_2$–C$_8$ alkenyl, C$_2$–C$_8$ alkynyl, C$_3$–C$_8$ cycloalkyl, C$_5$–C$_8$ cycloalkenyl, C$_3$–C$_8$ heterocycloalkyl, C$_5$–C$_8$ heterocycloalkenyl, aryl, or heteroaryl.

3. The compound of claim 1, wherein each of ====X$_1$—, ====X$_2$—, ====X$_3$—, and ====X$_4$—, independently, is —C=, —CR$_a$—, —N=, —N—, —S—, or a single bond; each of R$_1$ and R$_2$, independently, is H, C$_1$–C$_8$ alkyl, C$_2$–C$_8$ alkenyl, C$_2$–C$_8$ alkynyl, C$_3$–C$_8$ heterocycloalkyl, aryl, heteroaryl, C$_1$–C$_6$ alkoxy, aryloxy, heteroaryloxy, C$_1$–C$_6$ alkylthio, arylamino, diarylamino, —C(O)—NR$_b$R$_b$', or —C(O)—R$_b$; or R$_1$ and R$_2$ together are C$_5$–C$_8$ heterocycloalkyl; each of R$_5$, R$_6$, R$_7$, and R$_8$, independently, is H, C$_1$–C$_8$ alkyl, C$_2$–C$_8$ alkenyl, C$_2$–C$_8$ alkynyl, C$_3$–C$_8$ cycloalkyl, C$_5$–C$_8$ cycloalkenyl, C$_3$–C$_8$ heterocycloalkyl, C$_5$–C$_8$ heterocycloalkenyl, OH, C$_1$–C$_6$ alkoxy, aryloxy, heteroaryloxy, C$_1$–C$_6$ alkylthio, arylthio, NO$_2$, —C(O)—NR$_c$R$_c$', —C(O)—R$_c$, halogen, or deleted; or R$_6$ and R$_7$ together are C$_5$–C$_7$ cycloalkyl or C$_5$–C$_7$ heterocycloalkyl; provided that if R$_5$ is deleted, ====X$_1$— is —N=, —S—, or a single bond; if R$_6$ is deleted, ====X$_2$— is —N=, —S—, or a single bond; if R$_7$ is deleted, ====X$_3$— is —N=, —S—, or a single bond; and if R$_8$ is deleted, ====X$_4$— is —N=, —S—, or a single bond; B is H, C$_1$–C$_8$ alkyl, C$_2$–C$_8$ alkenyl, C$_2$–C$_8$ alkynyl, aryl, or heteroaryl; or B and A together are heteroaryl; D is H, aryl, heteroaryl, C$_3$–C$_8$ heterocycloalkyl, or C$_1$–C$_8$ alkyl; or D and A together are heteroaryl; and each of R$_a$, R$_b$, R$_b$', R$_c$, R$_c$', R$_d$, and R$_d$', independently, is H, C$_5$–C$_8$ cycloalkenyl, C$_5$–C$_8$ heterocycloalkenyl, aryl, or heteroaryl.

4. The compound of claim 3, wherein each of ====X$_1$—, ====X$_2$—, ====X$_3$—, and ====X$_4$—, independently, is —C=, —CR$_a$—, or —N=; each of R$_1$ and R$_2$, independently, is H, C$_1$–C$_8$ alkyl, C$_2$–C$_8$ alkenyl, C$_2$–C$_8$ alkynyl, aryl, C$_1$–C$_6$ alkoxy, aryloxy, heteroaryloxy, or C$_1$–C$_6$ alkylthio; or R$_1$ and R$_2$ together are C$_5$–C$_8$ heterocycloalkyl; each of R$_5$, R$_6$, R$_7$, and R$_8$, independently, is H, C$_1$–C$_8$ alkyl, C$_2$–C$_8$ alkenyl, C$_2$–C$_8$ alkynyl, C$_3$–C$_8$ heterocycloalkyl, OH, C$_1$–C$_6$ alkoxy, aryloxy, heteroaryloxy, C$_1$–C$_6$ alkylthio, arylthio, halogen, or deleted; or R$_6$ and R$_7$ together are C$_5$–C$_7$ cycloalkyl or C$_5$–C$_7$ heterocycloalkyl; provided that if R$_5$ is deleted, ====X$_1$— is —N=; if R$_6$ is deleted, ====X$_2$— is —N=; if R$_7$ is deleted, ====X$_3$— is —N=; and if R$_8$ is deleted, ====X$_4$— is —N=; A is C$_1$–C$_{12}$ alkyl optionally containing 1–6 heteroatoms and substituted with sulfonyl, C$_1$–C$_6$ alkylsulfonyl, arylsulfonyl, or heteroarylsulfonyl, C$_2$–C$_{12}$ alkenyl optionally containing 1–6 heteroatoms, C$_2$–C$_{12}$ alkynyl optionally containing 1–6 heteroatoms, aryl, C$_1$–C$_{10}$ alkylsulfonyl, arylsulfonyl, C$_1$–C$_{10}$ alkylcarbonyl containing 1–6 heteroatoms, C$_2$–C$_{20}$ alkylaryl optionally containing 1–6 heteroatoms, or C$_2$–C$_{20}$ arylalkyl optionally containing 1–6 heteroatoms; D is H, aryl, heteroaryl, C$_3$–C$_8$ heterocycloalkyl, or C$_1$–C$_8$ alkyl; and each of R$_a$, R$_b$, R$_b$', R$_c$, R$_c$', R$_d$, and R$_d$', independently, is H, aryl, or heteroaryl.

5. The compound of claim 4, wherein A is arylsulfonyl, C$_1$–C$_{10}$ alkylcarbonyl containing 1–6 heteroatoms, C$_2$–C$_{20}$ arylalkyl, or C$_1$–C$_{12}$ alkyl optionally containing 1–6 heteroatoms and substituted with sulfonyl, C$_1$–C$_6$ alkylsulfonyl, arylsulfonyl, or heteroarylsulfonyl; or A and B together are heteroaryl.

6. The compound of claim 5, wherein each of ====X$_1$—, ====X$_2$—, ====X$_3$—, and ====X$_4$—, independently, is —C=; each of R$_1$ and R$_2$, independently, is H or C$_1$–C$_8$ alkyl; each of R$_5$, R$_6$, R$_7$, and R$_8$, independently, is H, C$_1$–C$_8$ alkyl, C$_1$–C$_6$ alkoxy, or halogen; and B is H or B and A together are heteroaryl.

7. The compound of claim 6, wherein the compound is

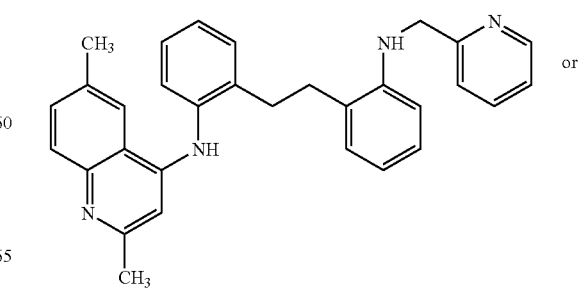

or

-continued

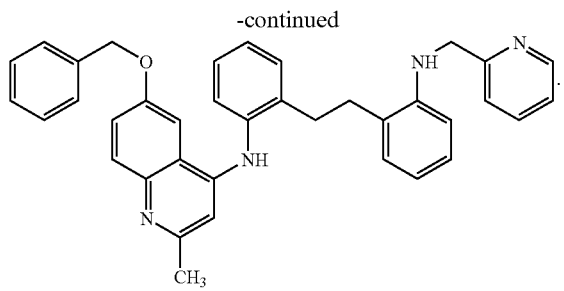

8. The compound of claim 4, wherein D is of formula (II),

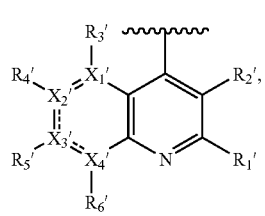

wherein
each ==== is a single bond or a double bond; provided that if one ==== is a double bond, its neighboring ==== is not a double bond;
each of ===$X_1'$—, ===$X_2'$—, ===$X_3'$—, and ===$X_4'$—, independently, is —C=, —CR$_e$—, or —N=; at most two of ===$X_1'$—, ===$X_2'$—, ===$X_3'$—, and ===$X_4'$— being —N=;
each of $R_1'$ and $R_2'$, independently, is H, $C_1$–$C_8$ alkyl, $C_2$–$C_8$ alkenyl, $C_2$–$C_8$ alkynyl, aryl, $C_1$–$C_6$ alkoxy, aryloxy, heteroaryloxy, or $C_1$–$C_6$ alkylthio; or $R_1'$ and $R_2'$ together are $C_5$–$C_8$ cycloalkyl or $C_5$–$C_8$ heterocycloalkyl; and
each of $R_3'$, $R_4'$, $R_5'$, and $R_6'$, independently, is H, $C_1$–$C_8$ alkyl, $C_2$–$C_8$ alkenyl, $C_2$–$C_8$ alkynyl, $C_3$–$C_8$ heterocycloalkyl, OH, $C_1$–$C_6$ alkoxy, aryloxy, heteroaryloxy, $C_1$–$C_6$ alkylthio, arylthio, or halogen; or $R_4'$ and $R_5'$ together are $C_5$–$C_7$ heterocycloalkyl
in which $R_e$ is H, aryl, or heteroaryl.

9. The compound of claim 8, wherein A is $C_1$–$C_{12}$ alkyl containing 1–6 heteroatoms and substituted with sulfonyl, $C_1$–$C_6$ alkylsulfonyl, arylsulfonyl, or heteroarylsulfonyl.

10. The compound of claim 8, wherein A is $C_2$–$C_{20}$ alkylaryl optionally containing 1–6 heteroatoms.

11. The compound of claim 8, wherein A is aryl, or A and B together are heteroaryl.

12. The compound of claim 9, wherein each of ===$X_1$—, ===$X_2$—, ===$X_3$—, and ===$X_4$—, independently, is —C=; each of $R_1$ and $R_2$, independently, is H or $C_1$–$C_8$ alkyl; each of $R_5$, $R_6$, $R_7$, and $R_8$, independently, is H, $C_1$–$C_8$ alkyl, $C_1$–$C_6$ alkoxy, aryloxy, $C_1$–$C_6$ alkylthio, or halogen; B is H; each of ===$X_1'$—, ===$X_2'$—, ===$X_3'$—, and ===$X_4'$—, independently, is —C=; each of $R_1'$ and $R_2'$, independently, is H or $C_1$–$C_8$ alkyl; or $R_1'$ and $R_2'$ together are $C_5$–$C_8$ cycloalkyl; each of $R_3'$, $R_4'$, $R_5'$, and $R_6'$, independently, is H, $C_1$–$C_8$ alkyl, $C_1$–$C_6$ alkoxy, aryloxy, $C_1$–$C_6$ alkylthio, or halogen.

13. The compound of claim 12, wherein the compound is one

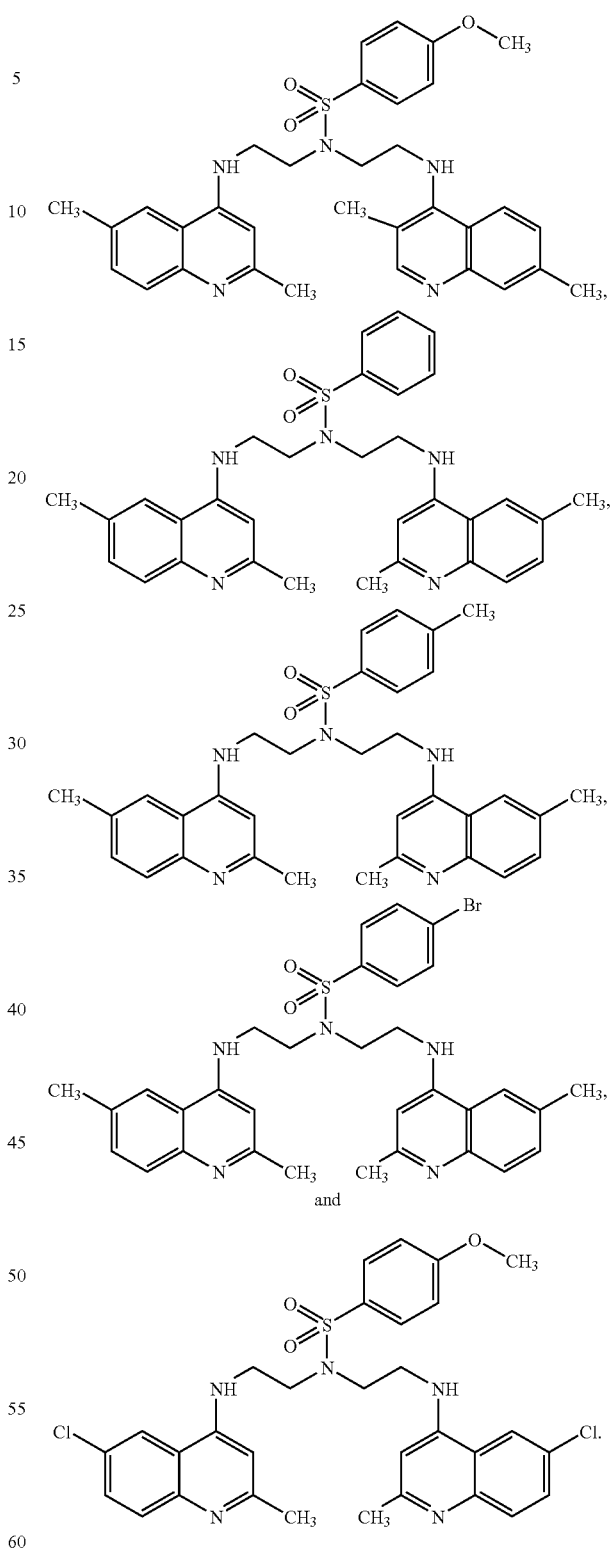

and

14. The compound of claim 10, wherein each of ===$X_1$—, ===$X_2$—, ===$X_3$—, and ===$X_4$—, independently, is —C=; each of $R_1$ and $R_2$, independently, is H or $C_1$–$C_8$ alkyl; each of $R_5$, $R_6$, $R_7$, and $R_8$, independently, is H, $C_1$–$C_8$ alkyl, $C_1$–$C_6$ alkoxy, aryloxy, or halogen; B is H; each of ===$X_1'$—, ===$X_2'$—, ===$X_3'$—, and ===$X_4'$—, independently, is —C═; each of R₁' and R₂', independently, is H or C₁–C₈ alkyl; each of R₃', R₄', R₅', and R₆', independently, is H, C₁–C₈ alkyl, C₁–C₆ alkoxy, aryloxy, or halogen.

15. The compound of claim 14, wherein the compound is one of

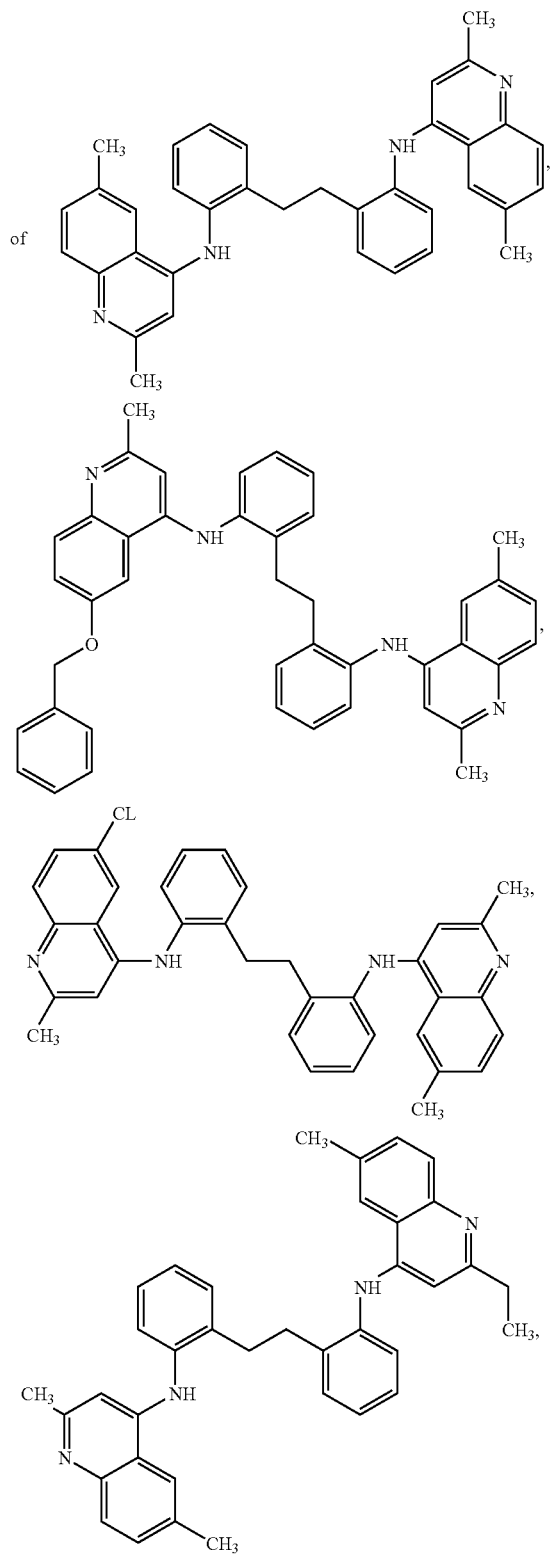

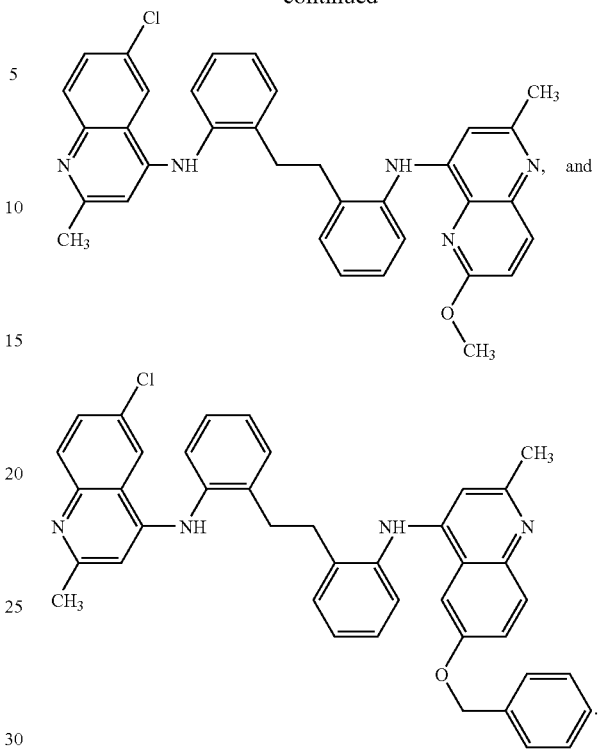

16. The compound of claim 11, wherein each of ═══X₁═, ═══X₂═, ═══X₃═, and ═══X₄═, independently, is —C═; each of R₁ and R₂, independently, is H or C₁–C₈ alkyl; each of R₅, R₆, R₇, and R₈, independently, is H or C₁–C₈ alkyl; B is H; or B and A together are heteroaryl; each of ═══X₁'═, ═══X₂'═, ═══X₃'═, and ═══X₄'═, independently, is —C═; each of R₁' and R₂', independently, is H or C₁–C₈ alkyl; each of R₃', R₄', R₅', and R₆', independently, is H or C₁–C₈ alkyl.

17. The compound of claim 16, wherein the compound is compound 36.

18. A compound of formula (I):

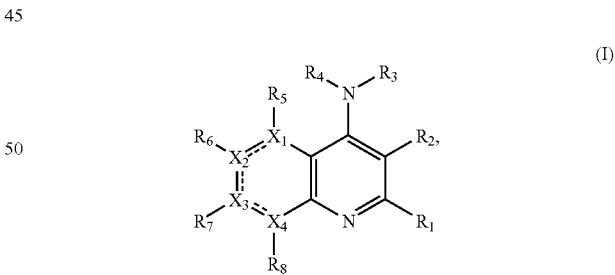

wherein
  each ═══ is a single bond or a double bond; provided that if one ═══ is a double bond, its neighboring ═══ is not a double bond;
  each of ═══X₁═, ═══X₂═, ═══X₃═, and ═══X₄═, independently, is —C═, CR$_a$, —N═, —N—, —S—, —O—, or a single bond; at most one of ═══X₁═, ═══X₂═, ═══X₃═, and ═══X₄═ being a single bond and at most two of ═══X₁═, ═══X₂═, ═══X₃═, and ═══X₄═ being —N═, —N—, —S—, or —O—;

R₁ is C₂–C₈ alkenyl, C₂–C₈ alkynyl, C₃–C₈ cycloalkyl, C₅–C₈ cycloalkenyl, C₃–C₈ heterocycloalkyl, C₅–C₈ heterocycloalkenyl, heteroaryl, OH, C₁–C₆ alkoxy, aryloxy, heteroaryloxy, C₁–C₆ alkylthio, arylthio, NH₂, C₁–C₆ alkylamino, C₁–C₁₂ dialkylamino, arylamino, diarylamino, —C(O)—NR$_b$R$_b$', —OC(O)—R$_b$, —C(O)—R$_b$, or halogen; R₂ is H, C₁–C₈ alkyl, C₂–C₈ alkenyl, C₂–C₈ alkynyl, C₃–C₈ cycloalkyl, C₅–C₈ cycloalkenyl, C₃–C₈ heterocycloalkyl, C₅–C₈ heterocycloalkenyl, aryl, heteroaryl, OH, C₁–C₆ alkoxy, aryloxy, heteroaryloxy, C₁–C₆ alkylthio, arylthio, NH₂, C₁–C₆ alkylamino, C₁–C₁₂ dialkylamino, arylamino, diarylamino, —C(O)—NR$_b$R$_b$', —OC(O)—R$_b$, —C(O)—R$_b$, or halogen; or R₁ and R₂ together are C₅–C₈ cycloalkyl or C₅–C₈ heterocycloalkyl;

each of R₃ and R₄, independently, is H or -A-N(B)-D; at most one of R₃ and R₄ being H; and each of R₅, R₆, R₇, and R₈, independently, is H, C₁–C₈ alkyl, C₂–C₈ alkenyl, C₂–C₈ alkynyl, C₃–C₈ cycloalkyl, C₅–C₈ cycloalkenyl, C₃–C₈ heterocycloalkyl, C₅–C₈ heterocycloalkenyl, aryl, heteroaryl, OH, C₁–C₆ alkoxy, aryloxy, heteroaryloxy, C₁–C₆ alkylthio, arylthio, NH₂, NO₂, CN, C₁–C₆ alkylamino, C₁–C₁₂ dialkylamino, arylamino, diarylamino, —C(O)—NR$_c$R$_c$', —C(O)—OR$_c$, —OC(O)—R$_c$, —C(O)—R$_c$, or deleted; or R₅ and R₆ together are C₅–C₇ cycloalkyl or C₅–C₇ heterocycloalkyl; or R₆ and R₇ together are C₅–C₇ cycloalkyl or C₅–C₇ heterocycloalkyl; or R₇ and R₈ together are C₅–C₇ cycloalkyl or C₅–C₇ heterocycloalkyl; provided that if R₅ is deleted, =====X₁— is —N=, —S—, —O—, or a single bond; if R₆ is deleted, =====X₂— is —N=, —S—, —O—, or a single bond; if R₇ is deleted, =====X₃— is —N=, —S—, —O—, or a single bond; and if R₈ is deleted, =====X₄— is —N=, —S—, —O—, or a single bond; and further provided that not all of R₅, R₆, R₇, and R₈ are H;

in which A is C₁–C₁₂ alkyl optionally containing 1–6 heteroatoms, C₂–C₁₂ alkenyl optionally containing 1–6 heteroatoms, C₂–C₁₂ alkynyl optionally containing 1–6 heteroatoms, aryl, heteroaryl, C₁–C₁₀ alkylsulfonyl, arylsulfonyl, C₁–C₁₀ alkylcarbonyl containing 1–6 heteroatoms, C₂–C₂₀ alkylaryl optionally containing 1–6 heteroatoms, C₂–C₂₀ arylalkyl optionally containing 1–6 heteroatoms, C₂–C₂₀ alkylheteroaryl containing 1–6 heteroatoms, or C₂–C₂₀ heteroarylalkyl containing 1–6 heteroatoms; B is H, C₁–C₈ alkyl, C₂–C₈ alkenyl, C₂–C₈ alkynyl, C₃–C₈ cycloalkyl, C₅–C₈ cycloalkenyl, C₃–C₈ heterocycloalkyl, C₅–C₈ heterocycloalkenyl, aryl, or heteroaryl; or B and A together are heteroaryl; and D is H, aryl, heteroaryl, C₂–C₈ alkenyl, C₂–C₈ alkynyl, C₃–C₈ cycloalkyl, C₅–C₈ cycloalkenyl, C₃–C₈ heterocycloalkyl, C₅–C₈ heterocycloalkenyl, —C(O)—R$_d$, —SO₂—R$_d$, —C(S)—R$_d$, —C(O)—NR$_d$R$_d$', —C(O)—OR$_d$, —OC(O)—R$_d$, —C(O)—SR$_d$, or —SC(O)—R$_d$; or D and A together are heteroaryl; each of R$_a$, R$_b$, R$_b$', R$_c$, R$_c$', R$_d$, and R$_d$', independently, being H, C₁–C₈ alkyl, C₂–C₈ alkenyl, C₂–C₈ alkynyl, C₃–C₈ cycloalkyl, C₅–C₈ cycloalkenyl, C₃–C₈ heterocycloalkyl, C₅–C₈ heterocycloalkenyl, aryl, or heteroaryl; or R$_d$ and R$_d$' together being C₅–C₇ heterocycloalkyl;

or a salt thereof.

19. The compound of claim 18, wherein D is of formula (II),

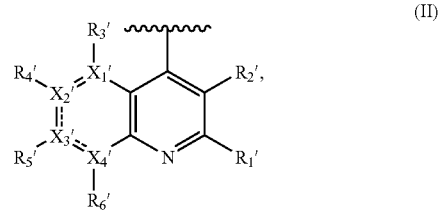

wherein
each ===== is a single bond or a double bond; provided that if one ===== is a double bond, its neighboring ===== is not a double bond;

each of =====X₁', =====X₂', =====X₃', and =====X₄', independently, is —C=, —CR$_e$—, —N=, —N—, —S—, —O—, or a single bond; at most one of =====X₁'—, =====X₂'—, =====X₃'—, and =====X₄'—, being a single bond, and at most two of =====X₁'—, =====X₂'—, =====X₃'—, and =====X₄'—, being —N=, —N—, —S—, or —O—;

each of R₁' and R₂', independently, is H, C₁–C₈ alkyl, C₂–C₈ alkenyl, C₂–C₈ alkynyl, C₃–C₈ cycloalkyl, C₅–C₈ cycloalkenyl, C₃–C₈ heterocycloalkyl, C₅–C₈ heterocycloalkenyl, aryl, heteroaryl, OH, C₁–C₆ alkoxy, aryloxy, heteroaryloxy, C₁–C₆ alkylthio, arylthio, NH₂, C₁–C₆ alkylamino, C₁–C₁₂ dialkylamino, arylamino, diarylamino, —C(O)—NR$_f$R$_f$', —OC(O)—R$_f$, —C(O)—R$_f$, or halogen; or R₁' and R₂' together are C₅–C₈ cycloalkyl or C₅–C₈ heterocycloalkyl;

each of R₃', R₄', R₅', and R₆', independently, is H, C₁–C₈ alkyl, C₂–C₈ alkenyl, C₂–C₈ alkynyl, C₃–C₈ cycloalkyl, C₅–C₈ cycloalkenyl, C₃–C₈ heterocycloalkyl, C₅–C₈ heterocycloalkenyl, aryl, heteroaryl, OH, C₁–C₆ alkoxy, aryloxy, heteroaryloxy, C₁–C₆ alkylthio, arylthio, NH₂, NO₂, CN, C₁–C₆ alkylamino, C₁–C₁₂ dialkylamino, arylamino, diarylamino, —C(O)—NR$_g$R$_g$', —OC(O)—R$_g$, —C(O)R$_g$, or deleted; or R₃' and R₄' together are C₅–C₇ cycloalkyl or C₅–C₇ heterocycloalkyl; or R₄' and R₅' together are C₅–C₇ cycloalkyl or C₅–C₇ heterocycloalkyl; or R₅' and R₆' together are C₅–C₇ cycloalkyl or C₅–C₇ heterocycloalkyl; provided that if R₃' is deleted, =====X₁'— is —N=, —S—, —O—, or a single bond; if R₄' is deleted, ====X₂'— is —N=, —S—, —O—, or a single bond; if R₅' is deleted, ====X₃'— is —N=, —S—, —O—, or a single bond; if R₆' is deleted, ====X₄'— is —N=, —S—, —O—, or a single bond; and further provided that not all of R₃', R₄', R₅', and R₆' are H;

in which each of R$_e$, R$_f$, R$_f$', R$_g$, and R$_g$', independently, being H, C₁–C₈ alkyl, C₂–C₈ alkenyl, C₂–C₈ alkynyl, C₃–C₈ cycloalkyl, C₅–C₈ cycloalkenyl, C₃–C₈ heterocycloalkyl, C₅–C₈ heterocycloalkenyl, aryl, or heteroaryl.

20. The compound of claim 18, wherein each of ===X₁—, ===X₂—, ===X₃—, and ===X₄—, independently, is —C=, —CR$_a$—, —N=, —N—, —S—, or a single bond; R₁ is C₂–C₈ alkenyl, C₂–C₈ alkynyl, C₃–C₈ heterocycloalkyl, heteroaryl, C₁–C₆ alkoxy, aryloxy, heteroaryloxy, C₁–C₆ alkylthio, arylamino, diarylamino, —C(O)—NR$_b$R$_b$', or —C(O)—R$_b$; R₂ is H, C₁–C₈ alkyl, C₂–C₈ alkenyl, C₂–C₈ alkynyl, C₃–C₈ heterocycloalkyl, aryl, heteroaryl, C₁–C₆ alkoxy, aryloxy, heteroaryloxy, C₁–C₆ alkylthio, arylamino, diarylamino, —C(O)—NR$_b$R$_b$', or —C(O)—R$_b$; or R₁ and R₂ together are C₅–C₈ cycloalkyl or $C_5$–$C_8$ heterocycloalkyl; each of $R_5$, $R_6$, $R_7$, and $R_8$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, OH, $C_1$–$C_6$ alkoxy, aryloxy, heteroaryloxy, $C_1$–$C_6$ alkylthio, arylthio, $NO_2$, —C(O)—$NR_cR_c'$, —C(O)—$R_c$, or deleted; or $R_6$ and $R_7$ together are $C_5$–$C_7$ cycloalkyl or $C_5$–$C_7$ heterocycloalkyl; provided that if $R_5$ is deleted, ═══$X_1$— is —N═, —S—, or a single bond; if $R_6$ is deleted, ═══$X_2$— is —N═, —S—, or a single bond; if $R_7$ is deleted, ═══$X_3$— is —N═, —S—, or a single bond; and if $R_8$ is deleted, ═══$X_4$— is —N═, —S—, or a single bond; B is H, $C_1$–$C_8$ alkyl, $C_2$–$C_8$ alkenyl, $C_2$–$C_8$ alkynyl, aryl, or heteroaryl; or B and A together are heteroaryl; D is H, aryl, heteroaryl, $C_3$–$C_8$ heterocycloalkyl, or —C(O)—$R_d$; or D and A together are heteroaryl; and each of $R_a$, $R_b$, $R_b'$, $R_c$, $R_c'$, $R_d$, and $R_d'$, independently, is H, $C_5$–$C_8$ cycloalkenyl, $C_5$–$C_8$ heterocycloalkenyl, aryl, or heteroaryl.

21. The compound of claim 20, wherein each of ═══$X_1$—, ═══$X_2$—, ═══$X_3$—, and ═══$X_4$—, independently, is —C═, —$CR_a$—, or —N═; $R_1$ is $C_2$–$C_8$ alkenyl, $C_2$–$C_8$ alkynyl, $C_1$–$C_6$ alkoxy, aryloxy, heteroaryloxy, or $C_1$–$C_6$ alkylthio; $R_2$ is H, $C_1$–$C_8$ alkyl, $C_2$–$C_8$ alkenyl, $C_2$–$C_8$ alkynyl, aryl, $C_1$–$C_6$ alkoxy, aryloxy, heteroaryloxy, or $C_1$–$C_6$ alkylthio; or $R_1$ and $R_2$ together are $C_5$–$C_8$ cycloalkyl or $C_5$–$C_8$ heterocycloalkyl; each of $R_5$, $R_6$, $R_7$, and $R_8$, independently, is H, $C_1$–$C_8$ alkyl, $C_2$–$C_8$ alkenyl, $C_2$–$C_8$ alkynyl, $C_3$–$C_8$ heterocycloalkyl, OH, $C_1$–$C_6$ alkoxy, aryloxy, heteroaryloxy, $C_1$–$C_6$ alkylthio, arylthio, or deleted; or $R_6$ and $R_7$ together are $C_5$–$C_7$ cycloalkyl or $C_5$–$C_7$ heterocycloalkyl; provided that if $R_5$ is deleted, ═══$X_1$— is —N═; if $R_6$ is deleted, ═══$X_2$— is —N═; if $R_7$ is deleted, ═══$X_3$— is —N═; and if $R_8$ is deleted, ═══$X_4$— is —N═; A is $C_1$–$C_{12}$ alkyl optionally containing 1–6 heteroatoms, $C_2$–$C_{12}$ alkenyl optionally containing 1–6 heteroatoms, $C_2$–$C_{12}$ alkynyl optionally containing 1–6 heteroatoms, aryl, $C_1$–$C_{10}$ alkylsulfonyl, arylsulfonyl, $C_1$–$C_{10}$ alkylcarbonyl containing 1–6 heteroatoms, $C_2$–$C_{20}$ alkylaryl optionally containing 1–6 heteroatoms, or $C_2$–$C_{20}$ arylalkyl optionally containing 1–6 heteroatoms; D is H, aryl, heteroaryl, $C_3$–$C_8$ heterocycloalkyl, or —C(O)—$R_d$; and each of $R_a$, $R_b$, $R_b'$, $R_c$, $R_c'$, $R_d$, and $R_d'$, independently, is H, aryl, or heteroaryl.

22. The compound of claim 21, wherein A is $C_1$–$C_{12}$ alkyl.

23. The compound of claim 22, wherein each of ═══$X_1$—, ═══$X_2$—, ═══$X_3$—, and ═══$X_4$—, independently, is —C═; $R_1$ and $R_2$ together are $C_5$–$C_8$ cycloalkyl; each of $R_5$, $R_6$, $R_7$, and $R_8$, independently, is H or $C_1$–$C_8$ alkyl; B is H; and D is H, heteroaryl, or —C(O)—$R_d$.

24. The compound of claim 23, wherein the compound is

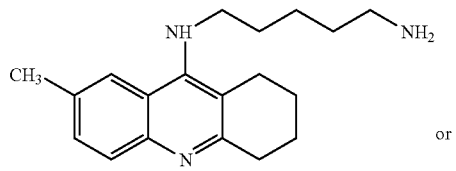

or

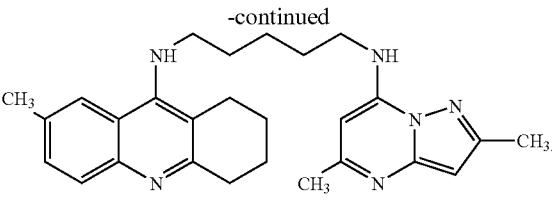

25. The compound of claim 21, wherein D is of formula (II),

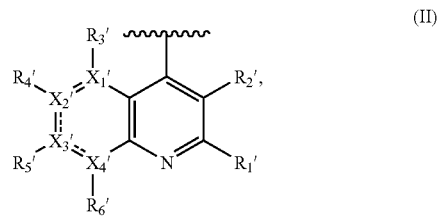

wherein each ═══ is a single bond or a double bond; provided that if one ═══ is a double bond, its neighboring ═══ is not a double bond;

each of ═══$X_1'$—, ═══$X_2'$—, ═══$X_3'$—, and ═══$X_4'$—, independently, is —C═, —$CR_e$—, or —N═; at most two of ═══$X_1'$—, ═══$X_2'$—, ═══$X_3'$—, and ═══$X_4'$— being —N═;

each of $R_1'$ and $R_2'$, independently, is H, $C_1$–$C_8$ alkyl, $C_2$–$C_8$ alkenyl, $C_2$–$C_8$ alkynyl, aryl, $C_1$–$C_6$ alkoxy, aryloxy, heteroaryloxy, or $C_1$–$C_6$ alkylthio; or $R_1'$ and $R_2'$ together are $C_5$–$C_8$ cycloalkyl or $C_5$–$C_8$ heterocycloalkyl; and each of $R_3'$, $R_4'$, $R_5'$, and $R_6'$, independently, is H, $C_1$–$C_8$ alkyl, $C_2$–$C_8$ alkenyl, $C_2$–$C_8$ alkynyl, $C_3$–$C_8$ heterocycloalkyl, OH, $C_1$–$C_6$ alkoxy, aryloxy, heteroaryloxy, $C_1$–$C_6$ alkylthio, or arylthio; or $R_4'$ and $R_5'$ together are $C_5$–$C_7$ cycloalkyl or $C_5$–$C_7$ heterocycloalkyl in which $R_e$ is H, aryl, or heteroaryl.

26. The compound of claim 25, wherein A is $C_1$–$C_{12}$ alkyl.

27. The compound of claim 25, wherein A is $C_1$–$C_{12}$ alkyl containing 1–6 heteroatoms and optionally substituted with sulfonyl, $C_1$–$C_6$ alkylsulfonyl, arylsulfonyl, or heteroarylsulfonyl.

28. The compound of claim 26, wherein each of ═══$X_1$—, ═══$X_2$—, ═══$X_3$—, and ═══$X_4$—, independently, is —C═; $R_1$ and $R_2$ together are $C_5$–$C_8$ cycloalkyl; each of $R_5$, $R_6$, $R_7$, and $R_8$, independently, is H, $C_1$–$C_8$ alkyl, $C_1$–$C_6$ alkoxy, or halogen; B is H; each of ═══$X_1'$—, ═══$X_2'$—, ═══$X_3'$—, and ═══$X_4'$—, independently, is —C═; each of $R_1'$ and $R_2'$, independently, is H or $C_1$–$C_8$ alkyl; or $R_1'$ and $R_2'$ together are $C_5$–$C_8$ cycloalkyl; each of $R_3'$, $R_4'$, $R_5'$, and $R_6'$, independently, is H, $C_1$–$C_8$ alkyl, or $C_1$–$C_6$ alkoxy.

29. The compound of claim 28, wherein the compound is one

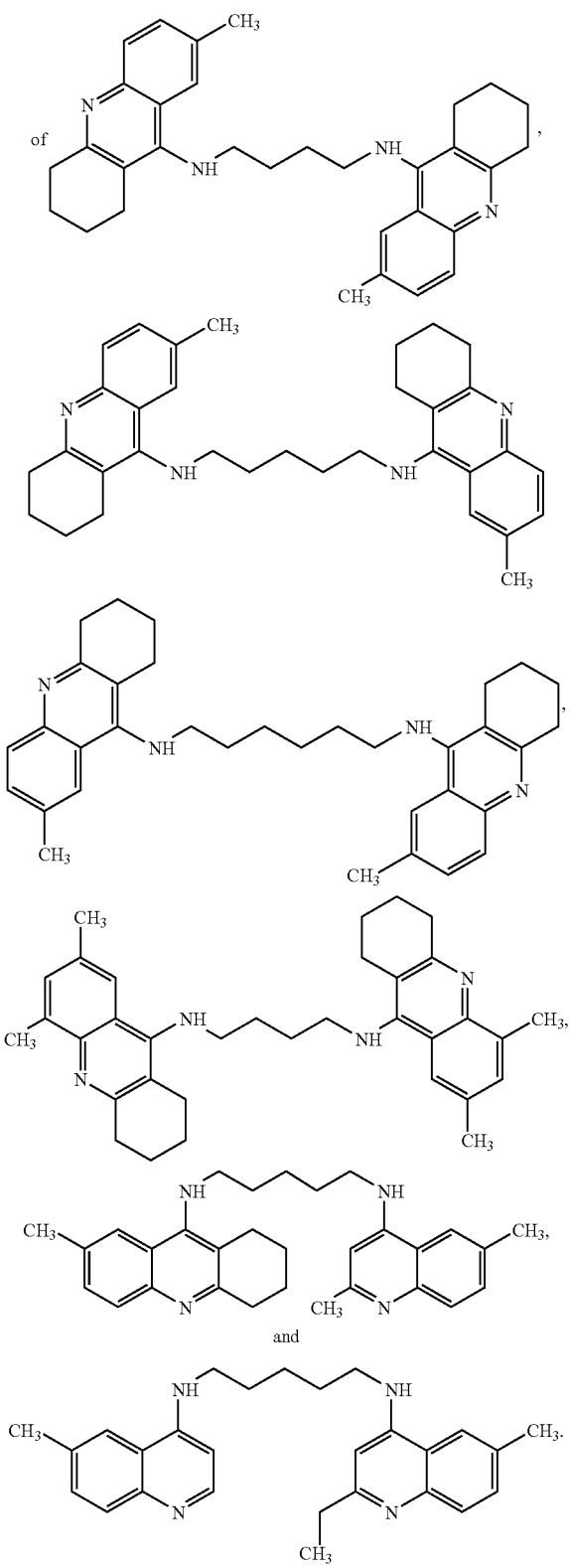

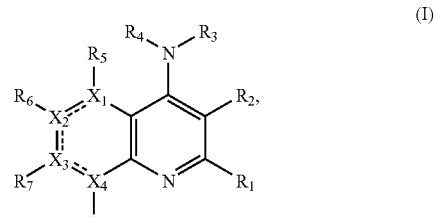

30. The compound of claim 27, wherein each of ===X$_1$—, ===X$_2$—, ===X$_3$—, and ===X$_4$—, independently, is —C=; R$_1$ and R$_2$ together are C$_5$–C$_8$ cycloalkyl; each of R$_5$, R$_6$, R$_7$, and R$_8$, independently, is H or C$_1$–C$_8$ alkyl; B is H; each of ====X$_1'$—, ====X$_2'$—, ====X$_3'$—, and ====X$_4'$—, independently, is —C=; R$_1'$ and R$_2'$ together are C$_5$–C$_8$ cycloalkyl; each of R$_3'$, R$_4'$, R$_5'$, and R$_6'$, independently, is H or C$_1$–C$_8$ alkyl.

31. A pharmaceutical composition comprising a compound of formula (I):

(I)

wherein
each ==== is a single bond or a double bond; provided that if one ==== is a double bond, its neighboring ==== is not a double bond;
each of ===X$_1$—, ===X$_2$—, ===X$_3$—, and ===X$_4$—, independently, is —C=, —CR$_a$—, —N=, —N—, —S—, —O—, or a single bond; at most one of ====X$_1$—, ====X$_2$—, ====X$_3$—, and ====X$_4$— being a single bond and at most two of ====X$_1$—, ====X$_2$—, ====X$_3$—, and ====X$_4$— being —N=, —N—, —S—, or —O—;
each of R$_1$ and R$_2$, independently, is H, C$_1$–C$_8$ alkyl, C$_2$–C$_8$ alkenyl, C$_2$–C$_8$ alkynyl, C$_3$–C$_8$ cycloalkyl, C$_5$–C$_8$ cycloalkenyl, C$_3$–C$_8$ heterocycloalkyl, C$_5$–C$_8$ heterocycloalkenyl, aryl, heteroaryl, OH, C$_1$–C$_6$ alkoxy, aryloxy, heteroaryloxy, C$_1$–C$_6$ alkylthio, arylthio, NH$_2$, C$_1$–C$_6$ alkylamino, C$_1$–C$_{12}$ dialkylamino, arylamino, diarylamino, —C(O)—NR$_b$R$_b'$, —C(O)—OR$_b$, —OC(O)—R$_b$, —C(O)—R$_b$, or halogen; or R$_1$ and R$_2$ together are C$_5$–C$_8$ cycloalkyl or C$_5$–C$_8$ heterocycloalkyl;
each of R$_3$ and R$_4$, independently, is H or -A-N(B)-D; and
each of R$_5$, R$_6$, R$_7$, and R$_8$, independently, is H, C$_1$–C$_8$ alkyl, C$_2$–C$_8$ alkenyl, C$_2$–C$_8$ alkynyl, C$_3$–C$_8$ cycloalkyl, C$_5$–C$_8$ cycloalkenyl, C$_3$–C$_8$ heterocycloalkyl, C$_5$–C$_8$ heterocycloalkenyl, aryl, heteroaryl, OH, C$_1$–C$_6$ alkoxy, aryloxy, heteroaryloxy, C$_1$–C$_6$ alkylthio, arylthio, NH$_2$, NO$_2$, CN, C$_1$–C$_6$ alkylamino, C$_1$–C$_{12}$ dialkylamino, arylamino, diarylamino, —C(O)—NR$_c$R$_c'$, —C(O)—OR$_c$, —OC(O)—R$_c$, —C(O)—R$_c$, halogen, or deleted; or R$_5$ and R$_6$ together are C$_5$–C$_7$ cycloalkyl or C$_5$–C$_7$ heterocycloalkyl; or R$_6$ and R$_7$ together are C$_5$–C$_7$ cycloalkyl or C$_5$–C$_7$ heterocycloalkyl; or R$_7$ and R$_8$ together are C$_5$–C$_7$ cycloalkyl or C$_5$–C$_7$ heterocycloalkyl; provided that if R$_5$ is deleted, ====X$_1$— is —N=, —S—, —O—, or a single bond; if R$_6$ is deleted, ====X$_2$— is —N=, —S—, —O—, or a single bond; if R$_7$ is deleted, ====X$_3$— is —N=, —S—, —O—, or a single bond; and if R$_8$ is deleted, ====X$_4$— is —N=, —S—, —O—, or a single bond;
in which A is C$_1$–C$_{12}$ alkyl optionally containing 1–6 heteroatoms and substituted with sulfonyl, C$_1$–C$_6$ alkylsulfonyl, arylsulfonyl, or heteroarylsulfonyl, C$_2$–C$_{12}$ alkenyl optionally containing 1–6 heteroatoms, C$_2$–C$_{12}$ alkynyl optionally containing 1–6 heteroatoms, aryl, heteroaryl, C$_1$–C$_{10}$ alkylsulfonyl, arylsulfonyl, C$_1$–C$_{10}$ alkylcarbonyl containing 1–6 heteroatoms, C$_2$–C$_{20}$ alkylaryl optionally containing 1–6 heteroatoms, $C_2$–$C_{20}$ arylalkyl optionally containing 1–6 heteroatoms, $C_2$–$C_{20}$ alkylheteroaryl containing 1–6 heteroatoms, or $C_2$–$C_{20}$ heteroarylalkyl containing 2–6 heteroatoms; B is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, or heteroaryl; or B and A together are $C_5$–$C_7$ heterocycloalkyl or heteroaryl; and D is H, aryl, heteroaryl, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, —C(O)—$R_d$, —SO$_2$—$R_d$, —C(S)—$R_d$, —C(O)—NR$_d$R$_d$', —C(O)—OR$_d$, —OC(O)—$R_d$, —C(O)—SR$_d$, or —SC(O)—$R_d$; or D and A together are $C_5$–$C_7$ heterocycloalkyl or heteroaryl; each of $R_a$, $R_b$, $R_b'$, $R_c$, $R_c'$, $R_d$, and $R_d'$, independently, being H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, or heteroaryl; or $R_d$ and $R_d'$ together being $C_5$–$C_7$ heterocycloalkyl; or a salt thereof; and a pharmaceutically acceptable carrier.

32. The composition of claim 31, wherein D is of formula (II),

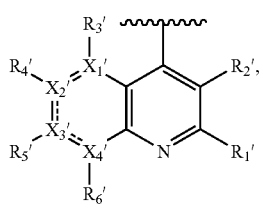

(II)

wherein
each ==== is a single bond or a double bond; provided that if one ==== is a double bond, its neighboring ==== is not a double bond; each of ====$X_1'$—, ====$X_2'$—, ====$X_3'$—, and ====$X_4'$—, independently, is —C=, —CR$_e$—, —N=, —N—, —S—, —O—, or a single bond; at most one of ====$X_1'$—, ====$X_2'$—, ====$X_3'$—, and ====$X_4'$—, being a single bond, and at most two of ====$X_1'$—, ====$X_2'$—, ====$X_3'$—, and ====$X_4'$—, being —N=, —N—, —S—, or —O—;

each of $R_1'$ and $R_2'$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, NH$_2$, $C_1$–$C_6$ alkylamino, $C_1$–$C_{12}$ dialkylamino, arylamino, diarylamino, —C(O)—NR$_f$R$_f'$, —C(O)—OR$_f$, —OC(O)—$R_f$, —C(O)—$R_f$, or halogen; or $R_1'$ and $R_2'$ together are $C_5$–$C_8$ cycloalkyl or $C_5$–$C_8$ heterocycloalkyl;

each of $R_3'$, $R_4'$, $R_5'$, and $R_6'$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, heteroaryl, OH, $C_1$–$C_6$ alkoxy, aryloxy, heteroaryloxy, $C_1$–$C_6$ alkylthio, arylthio, NH$_2$, NO$_2$, CN, $C_1$–$C_6$ alkylamino, $C_1$–$C_{12}$ dialkylamino, arylamino, diarylamino, —C(O)—NR$_g$R$_g'$, —C(O)—OR$_g$, —OC(O)—$R_g$, C(O)R$_g$, halogen, or deleted; or $R_3'$ and $R_4'$ together are $C_5$–$C_7$ cycloalkyl or $C_5$–$C_7$ heterocycloalkyl; or $R_4'$ and $R_5'$ together are $C_5$–$C_7$ cycloalkyl or $C_5$–$C_7$ heterocycloalkyl; or $R_5'$ and $R_6'$ together are $C_5$–$C_7$ cycloalkyl or $C_5$–$C_7$ heterocycloalkyl; provided that if $R_3'$ is deleted, ====$X_1'$— is —N=, —S—, —O—, or a single bond; if $R_4'$ is deleted, ====$X_2'$— is —N=, —S—, —O—, or a single bond; if $R_5'$ is deleted, ====$X_3'$— is —N=, —S—, —O—, or a single bond; and if $R_6'$ is deleted, ====$X_4'$— is —N=, —S—, —O—, or a single bond;

in which each of $R_e$, $R_f$, $R_f'$, $R_g$, and $R_g'$, independently, being H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, aryl, or heteroaryl.

33. The composition of claim 31, wherein each of ====$X_1$—, ====$X_2$—, ====$X_3$—, and ====$X_4$—, independently, is —C=, —CR$_a$—, —N=, —N—, —S—, or a single bond; each of $R_1$ and $R_2$, independently, is H, $C_1$–$C_8$ alkyl, $C_2$–$C_8$ alkenyl, $C_2$–$C_8$ alkynyl, $C_3$–$C_8$ heterocycloalkyl, aryl, heteroaryl, $C_1$–$C_6$ alkoxy, aryloxy, heteroaryloxy, $C_1$–$C_6$ alkylthio, arylamino, diarylamino, —C(O)—NR$_b$R$_b'$, or —C(O)—$R_b$; or $R_1$ and $R_2$ together are $C_5$–$C_7$ cycloalkyl or $C_5$–$C_7$ heterocycloalkyl; each of $R_5$, $R_6$, $R_7$, and $R_8$, independently, is H, $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, $C_3$–$C_8$ heterocycloalkyl, $C_5$–$C_8$ heterocycloalkenyl, OH, $C_1$–$C_6$ alkoxy, aryloxy, heteroaryloxy, $C_1$–$C_6$ alkylthio, arylthio, NO$_2$, —C(O)—NR$_c$R$_c'$, —C(O)—R$_c$, halogen, or deleted; or $R_6$ and $R_7$ together are $C_5$–$C_7$ cycloalkyl or $C_5$–$C_7$ heterocycloalkyl; provided that if $R_5$ is deleted, ====$X_1$— is —N=, —S—, or a single bond; if $R_6$ is deleted, ====$X_2$— is —N=, —S—, or a single bond; if $R_7$ is deleted, ====$X_3$— is —N=, —S—, or a single bond; and if $R_8$ is deleted, ====$X_4$— is —N=, —S—, or a single bond; B is H, $C_1$–$C_8$ alkyl, $C_2$–$C_8$ alkenyl, $C_2$–$C_8$ alkynyl, aryl, or heteroaryl; or B and A together are $C_5$–$C_7$ heterocycloalkyl or heteroaryl; D is H, aryl, heteroaryl, $C_1$–$C_8$ alkyl, $C_3$–$C_8$ heterocycloalkyl, or —C(O)—$R_d$; or D and A together are $C_5$–$C_7$ heterocycloalkyl or heteroaryl; and each of $R_a$, $R_b$, $R_b'$, $R_c$, $R_c'$, $R_d$, and $R_d'$, independently, being H, $C_5$–$C_8$ cycloalkenyl, $C_5$–$C_8$ heterocycloalkenyl, aryl, or heteroaryl.

34. The composition of claim 33, wherein each of ====$X_1$—, ====$X_2$—, ====$X_3$—, and ====$X_4$—, independently, is —C=, —CR$_a$—, or —N=; each of $R_1$ and $R_2$, independently, is H, $C_1$–$C_8$ alkyl, $C_2$–$C_8$ alkenyl, $C_2$–$C_8$ alkynyl, aryl, $C_1$–$C_6$ alkoxy, aryloxy, heteroaryloxy, or $C_1$–$C_6$ alkylthio; or $R_1$ and $R_2$ together are $C_5$–$C_8$ cycloalkyl or $C_5$–$C_8$ heterocycloalkyl; each of $R_5$, $R_6$, $R_7$, and $R_8$, independently, is H, $C_1$–$C_8$ alkyl, $C_2$–$C_8$ alkenyl, $C_2$–$C_8$ alkynyl, $C_3$–$C_8$ heterocycloalkyl, OH, $C_1$–$C_6$ alkoxy, aryloxy, heteroaryloxy, $C_1$–$C_6$ alkylthio, arylthio, halogen, or deleted; or $R_6$ and $R_7$ together are $C_5$–$C_7$ cycloalkyl or $C_5$–$C_7$ heterocycloalkyl; provided that if $R_5$ is deleted, ====$X_1$— is —N=; if $R_6$ is deleted, ====$X_2$— is —N=; if $R_7$ is deleted, ====$X_3$— is —N=; and if $R_8$ is deleted, ====$X_4$— is —N=; A is $C_1$–$C_{12}$ alkyl optionally containing 1–6 heteroatoms and substituted with sulfonyl, $C_1$–$C_6$ alkylsulfonyl, arylsulfonyl, or heteroarylsulfonyl, $C_2$–$C_{12}$ alkenyl optionally containing 1–6 heteroatoms, $C_2$–$C_{12}$ alkynyl optionally containing 1–6 heteroatoms, aryl, $C_1$–$C_{10}$ alkylsulfonyl, arylsulfonyl, $C_1$–$C_{10}$ alkylcarbonyl containing 1–6 heteroatoms, $C_2$–$C_{20}$ alkylaryl optionally containing 1–6 heteroatoms, or $C_2$–$C_{20}$ arylalkyl optionally containing 1–6 heteroatoms; D is H, aryl, heteroaryl, $C_1$–$C_8$ alkyl, $C_3$–$C_8$ heterocycloalkyl, or —C(O)—$R_d$; and each of $R_a$, $R_b$, $R_b'$, $R_c$, $R_c'$, $R_d$, and $R_d'$, independently, being H, aryl, or heteroaryl.

35. The composition of claim 34, wherein A is arylsulfonyl, $C_1$–$C_{10}$ alkylcarbonyl containing 1–6 heteroatoms, $C_2$–$C_{20}$ arylalkyl, or $C_1$–$C_{12}$ alkyl optionally containing 1–6 heteroatoms and substituted with sulfonyl, $C_1$–$C_6$ alkylsulfonyl, arylsulfonyl, or heteroarylsulfonyl or A and B together are heteroaryl.

36. The composition of claim 35, wherein each of ====$X_1$—, ====$X_2$—, ====$X_3$—, and ====$X_4$—, independently, is —C=; each of $R_1$ and $R_2$, independently, is H or $C_1$–$C_8$ alkyl; or $R_1$ and $R_2$ together are $C_5$–$C_8$ cycloalkyl; each of $R_5$, $R_6$, $R_7$, and $R_8$, independently, is H, $C_1$–$C_8$ alkyl, $C_1$–$C_6$ alkoxy, or halogen; and B is H or B and A together are heteroaryl.

37. The composition of claim 34, wherein D is of formula (II),

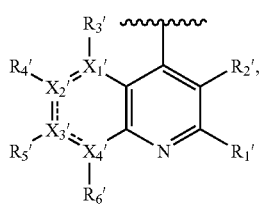

(II)

wherein
each ==== is a single bond or a double bond; provided that if one ==== is a double bond, its neighboring ==== is not a double bond;
each of ====$X_1$'—, ====$X_2$'—, ====$X_3$'—, and ====$X_4$'—, independently, is —C=, —$CR_e$—, or —N=; at most two of ====$X_1$'—, ====$X_2$'—, ====$X_3$'—, and ====$X_4$'— being —N=;
each of $R_1$' and $R_2$', independently, is H, $C_1$–$C_8$ alkyl, $C_2$–$C_8$ alkenyl, $C_2$–$C_8$ alkynyl, aryl, $C_1$–$C_6$ alkoxy, aryloxy, heteroaryloxy, or $C_1$–$C_6$ alkylthio; or $R_1$' and $R_2$' together are $C_5$–$C_8$ cycloalkyl or $C_5$–$C_8$ heterocycloalkyl; and
each of $R_3$', $R_4$', $R_5$', and $R_6$', independently, is H, $C_1$–$C_8$ alkyl, $C_2$–$C_8$ alkenyl, $C_2$–$C_8$ alkynyl, $C_3$–$C_8$ heterocycloalkyl, OH, $C_1$–$C_6$ alkoxy, aryloxy, heteroaryloxy, $C_1$–$C_6$ alkylthio, arylthio, or halogen; or $R_4$' and $R_5$' together are $C_5$–$C_7$ cycloalkyl or $C_5$–$C_7$ heterocycloalkyl in which $R_e$ is H, aryl, or heteroaryl.

38. The composition of claim 37, wherein A is $C_1$–$C_{12}$ alkyl containing 1–6 heteroatoms and substituted with sulfonyl, $C_1$–$C_6$ alkylsulfonyl, arylsulfonyl, or heteroarylsulfonyl.

39. The composition of claim 37, wherein A is $C_2$–$C_{20}$ alkylaryl optionally containing 1–6 heteroatoms.

40. The composition of claim 37, wherein A is aryl, or A and B together are heteroaryl.

41. The composition of claim 38, wherein each of ====$X_1$—, ====$X_2$—, ====$X_3$—, and ====$X_4$—, independently, is —C=; each of $R_1$ and $R_2$, independently, is H or $C_1$–$C_8$ alkyl; or $R_1$ and $R_2$ together are $C_5$–$C_8$ cycloalkyl; each of $R_5$, $R_6$, $R_7$, and $R_8$, independently, is H, $C_1$–$C_8$ alkyl, $C_1$–$C_6$ alkoxy, aryloxy, $C_1$–$C_6$ alkylthio, or halogen; B is H; each of ====$X_1$'—, ====$X_2$'—, ====$X_3$'—, and ====$X_4$'—, independently, is —C=; each of $R_1$' and $R_2$', independently, is H or $C_1$–$C_8$ alkyl; or $R_1$' and $R_2$' together are $C_5$–$C_8$ cycloalkyl; each of $R_3$', $R_4$', $R_5$', and $R_6$', independently, is H, $C_1$–$C_8$ alkyl, $C_1$–$C_6$ alkoxy, aryloxy, $C_1$–$C_6$ alkylthio, or halogen.

42. The composition of claim 39, wherein each of ====$X_1$—, ====$X_2$—, ====$X_3$—, and ====$X_4$—, independently, is —C=; each of $R_1$ and $R_2$, independently, is H or $C_1$–$C_8$ alkyl; each of $R_5$, $R_6$, $R_7$, and $R_8$, independently, is H, $C_1$–$C_8$ alkyl, $C_1$–$C_6$ alkoxy, aryloxy, or halogen; B is H; each of ====$X_1$'—, ====$X_2$'—, ====$X_3$'—, and ====$X_4$'—, independently, is —C=; each of $R_1$' and $R_2$', independently, is H or $C_1$–$C_8$ alkyl; each of $R_3$', $R_4$', $R_5$', and $R_6$', independently, is H, $C_1$–$C_8$ alkyl, $C_1$–$C_6$ alkoxy, aryloxy, or halogen.

43. The composition of claim 40, wherein each of ====$X_1$—, ====$X_2$—, ====$X_3$—, and ====$X_4$—, independently, is —C=; each of $R_1$ and $R_2$, independently, is H or $C_1$–$C_8$ alkyl; each of $R_5$, $R_6$, $R_7$, and $R_8$, independently, is H or $C_1$–$C_8$ alkyl; B is H; or B and A together are heteroaryl; each of ====$X_1$'—, ====$X_2$'—, ====$X_3$'—, and ====$X_4$'—, independently, is —C=; each of $R_1$' and $R_2$', independently, is H or $C_1$–$C_8$ alkyl; each of $R_3$', $R_4$', $R_5$', and $R_6$', independently, is H or $C_1$–$C_8$ alkyl.

44. A pharmaceutical composition comprising a compound of claim 18 and a pharmaceutically acceptable carrier.

45. A compound selected from the group consisting of

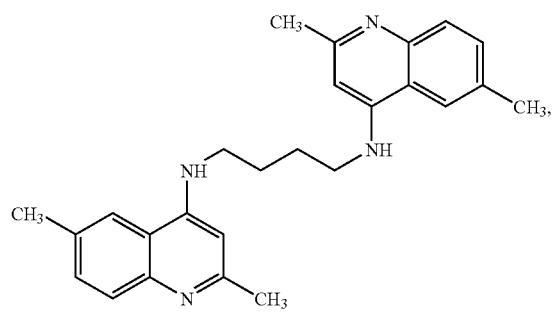

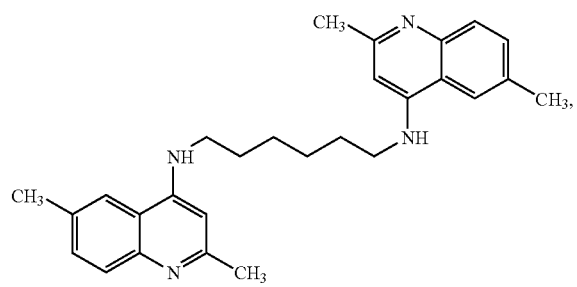

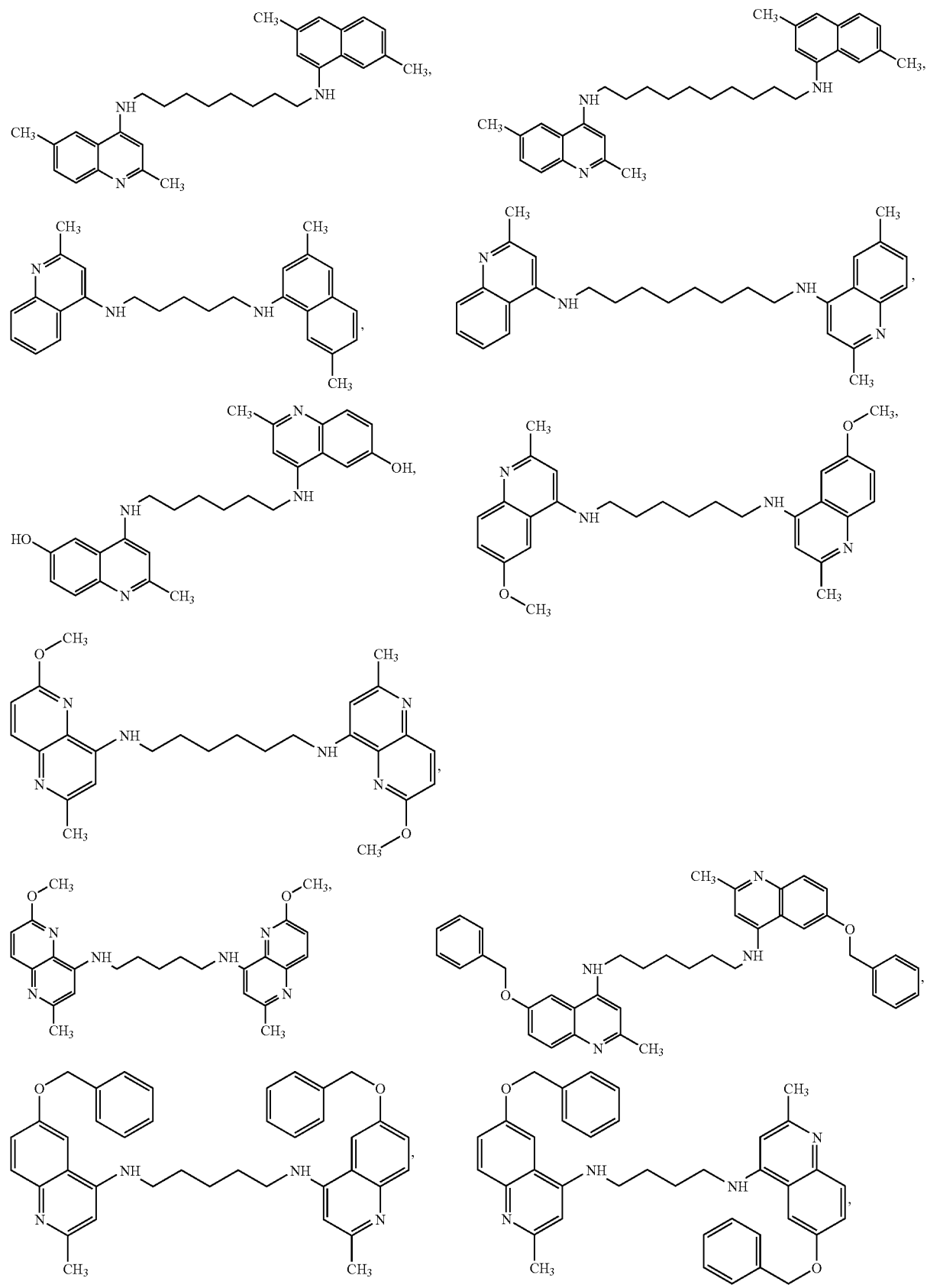

-continued
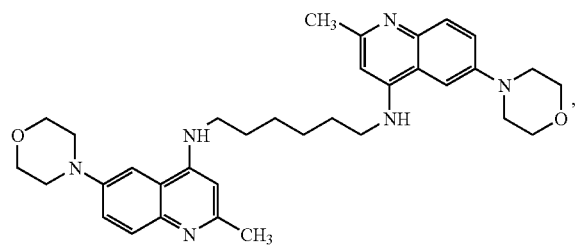
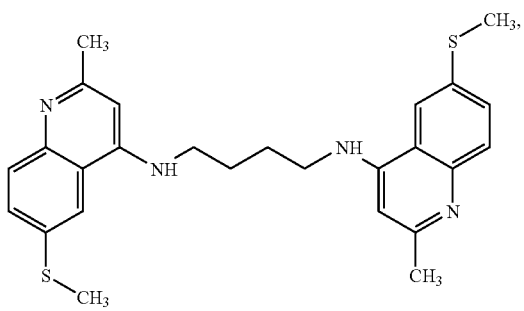
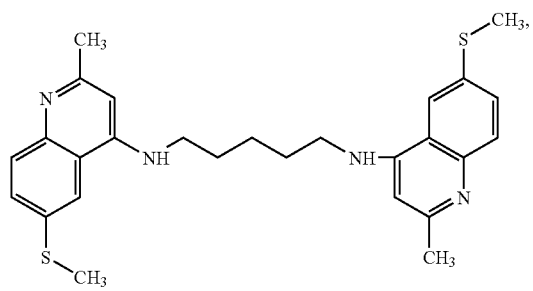
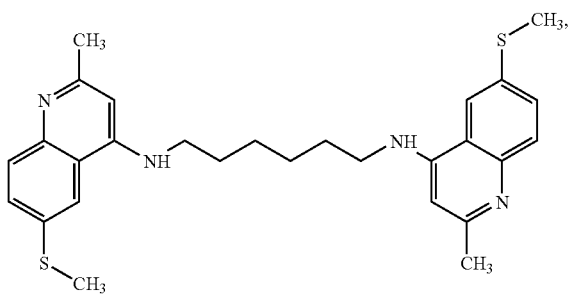
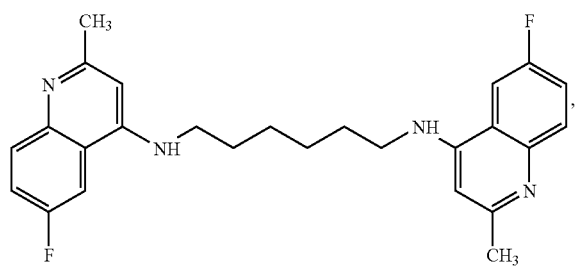
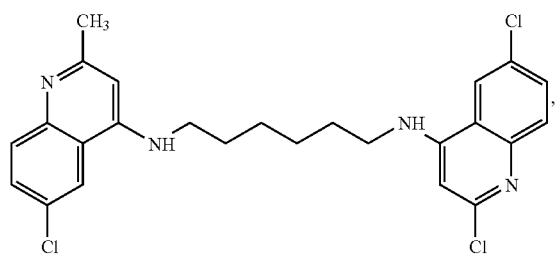
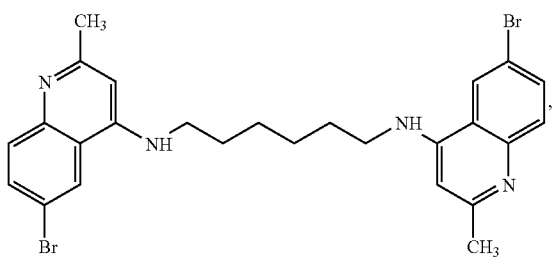
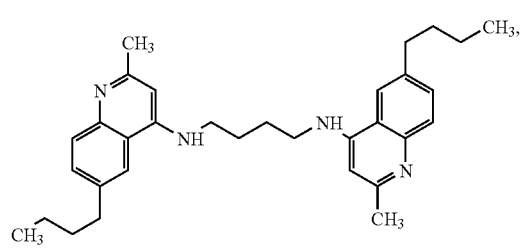

-continued
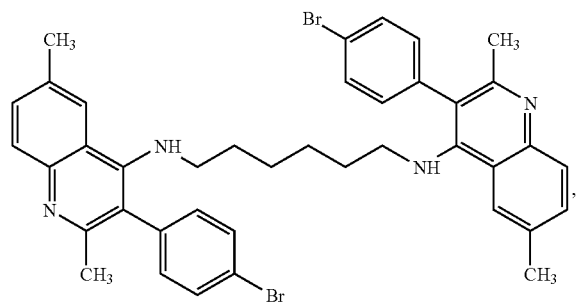
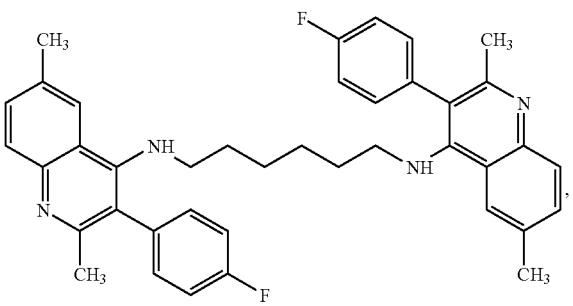
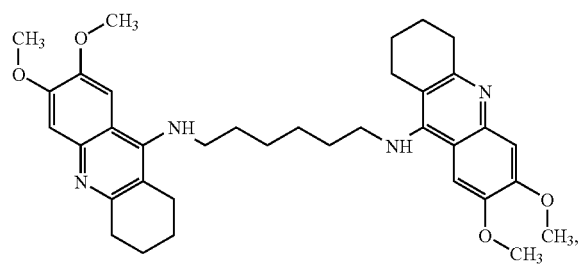
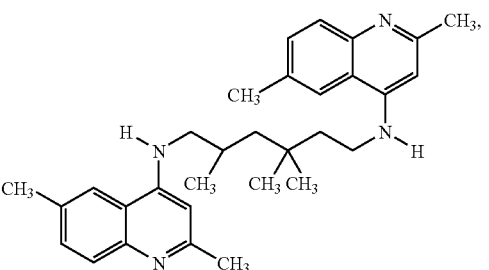
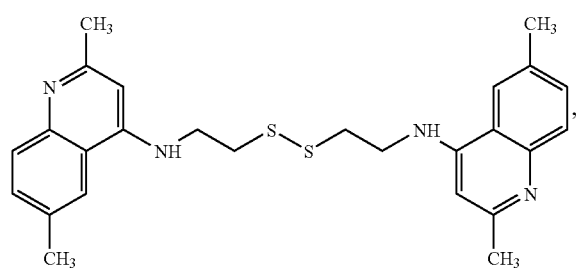
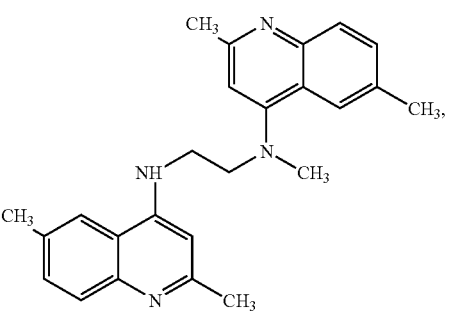
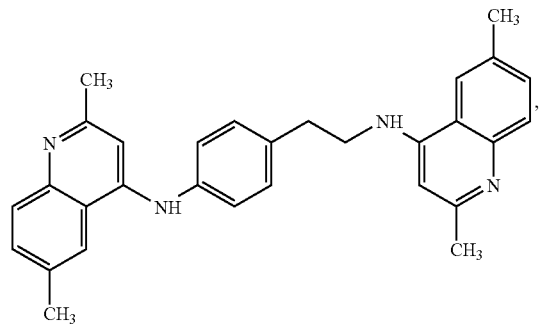
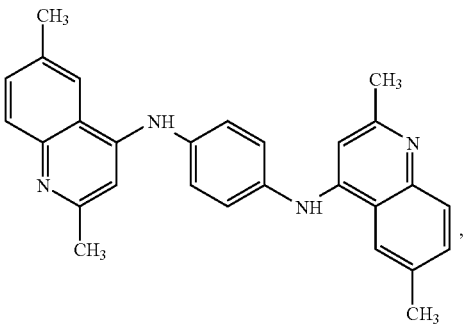
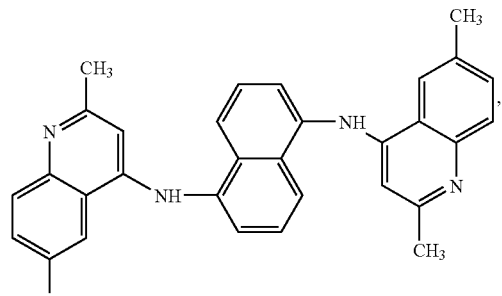
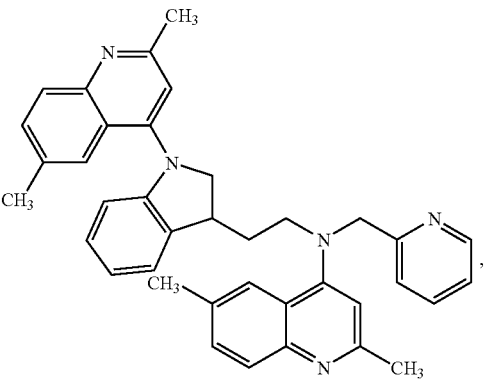

-continued
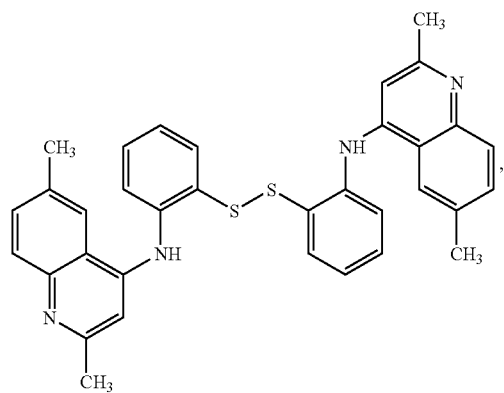
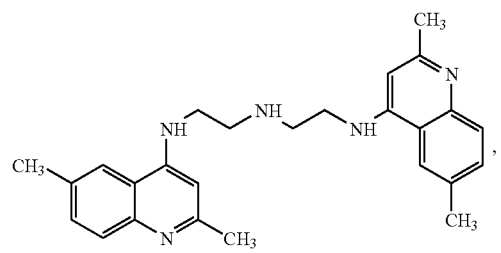
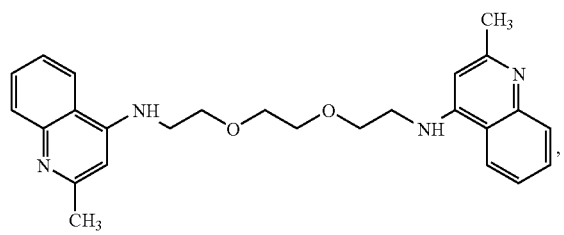
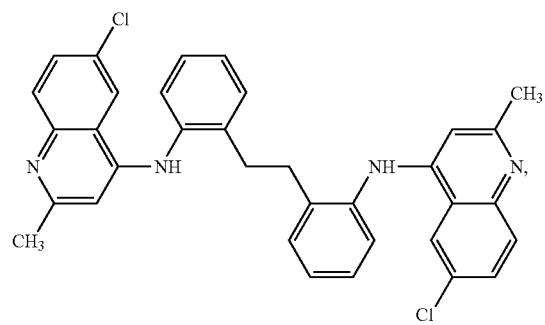
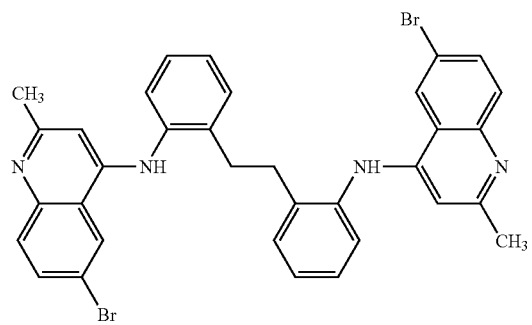
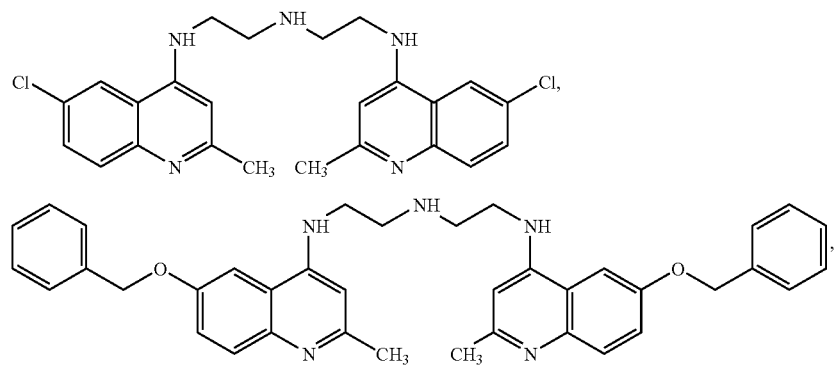

-continued
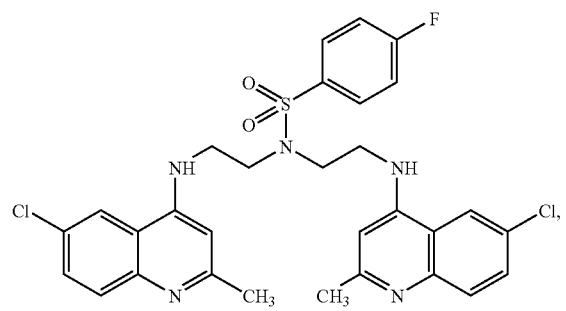
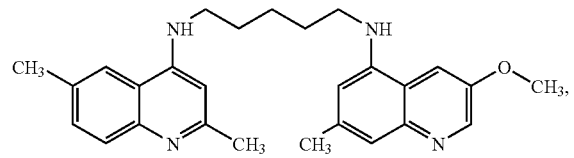
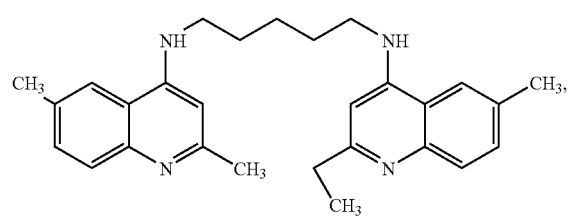
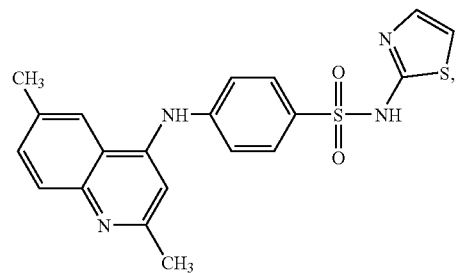
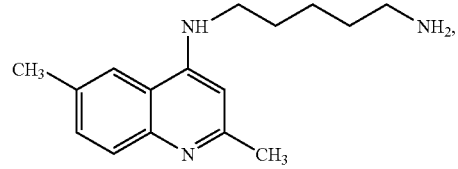
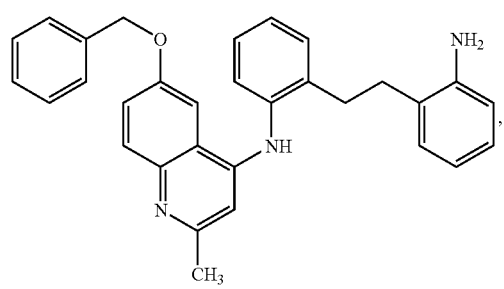
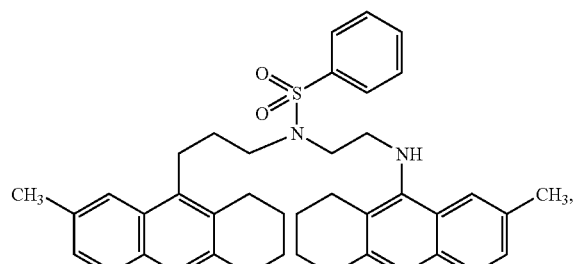
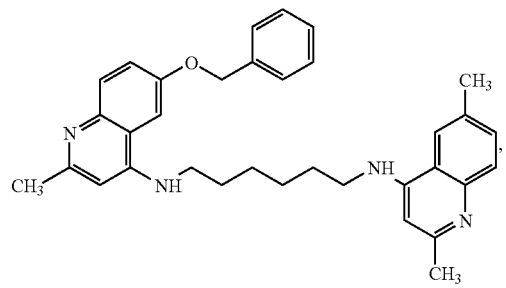
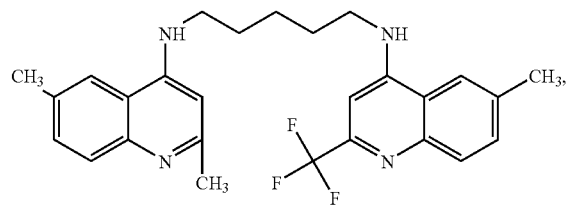
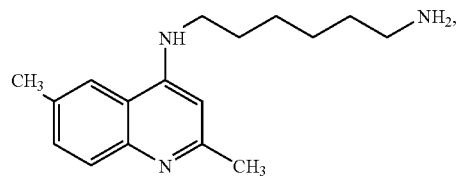
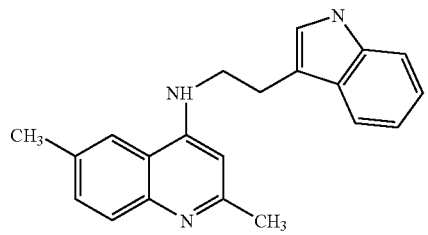
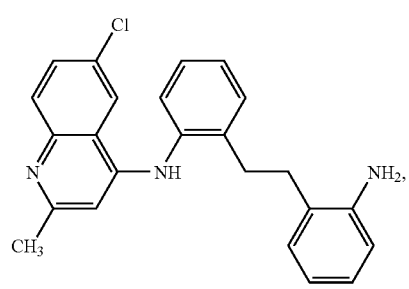

-continued
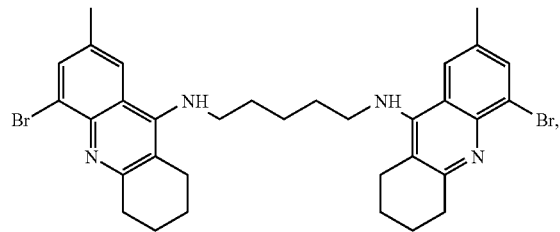
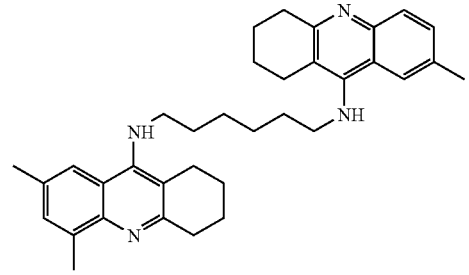
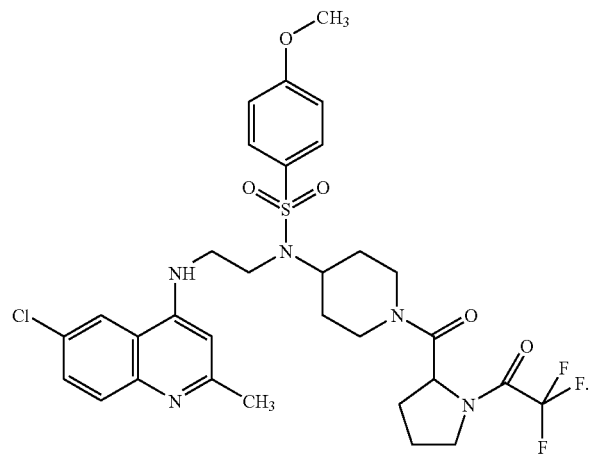
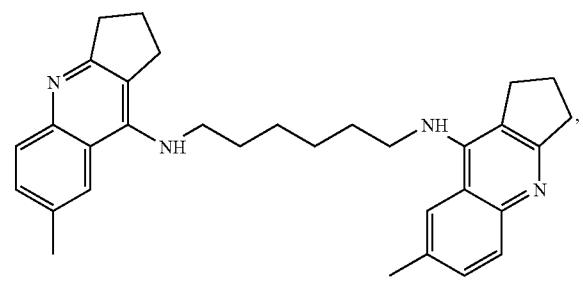
-continued
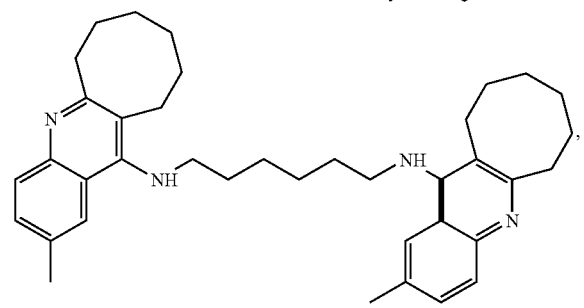
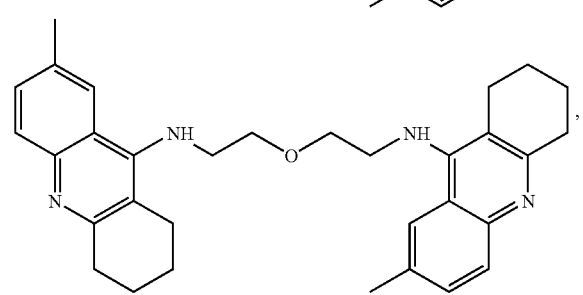

-continued
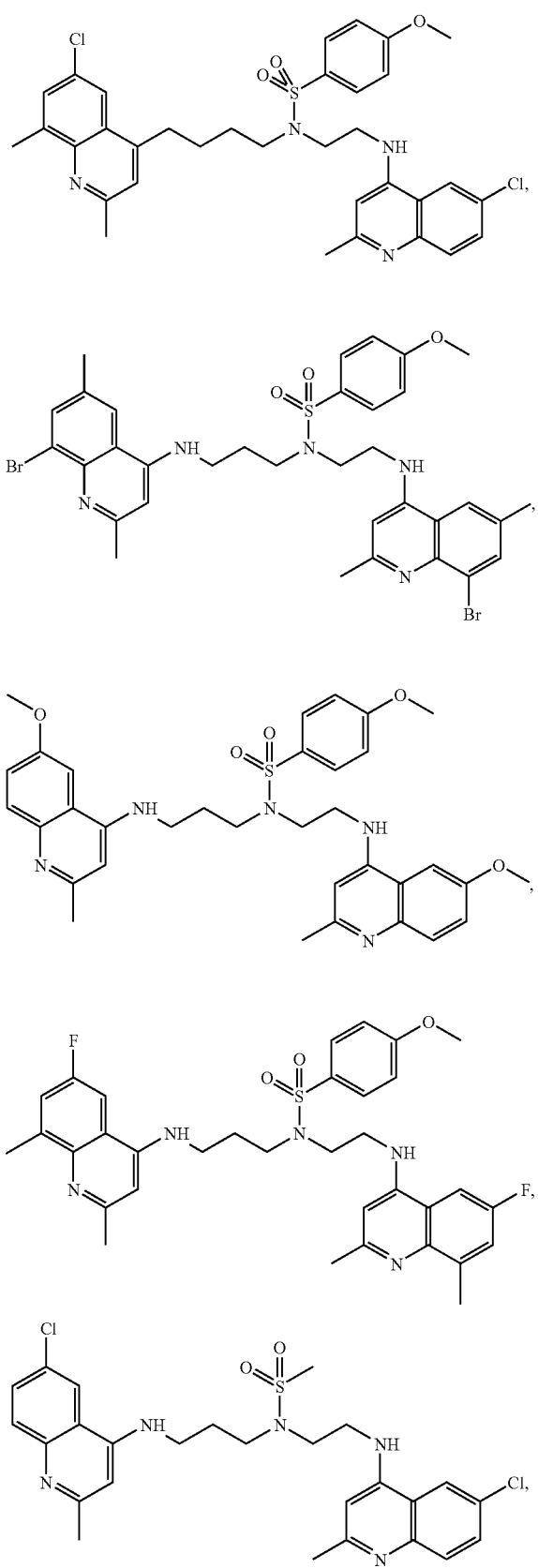
-continued
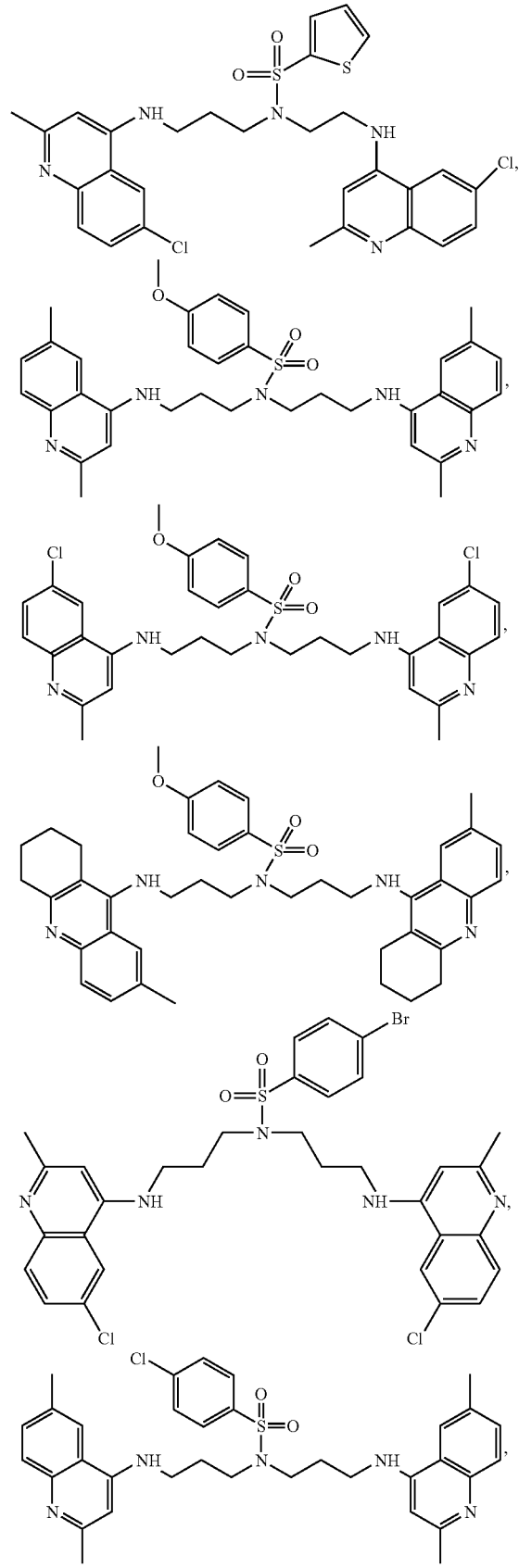

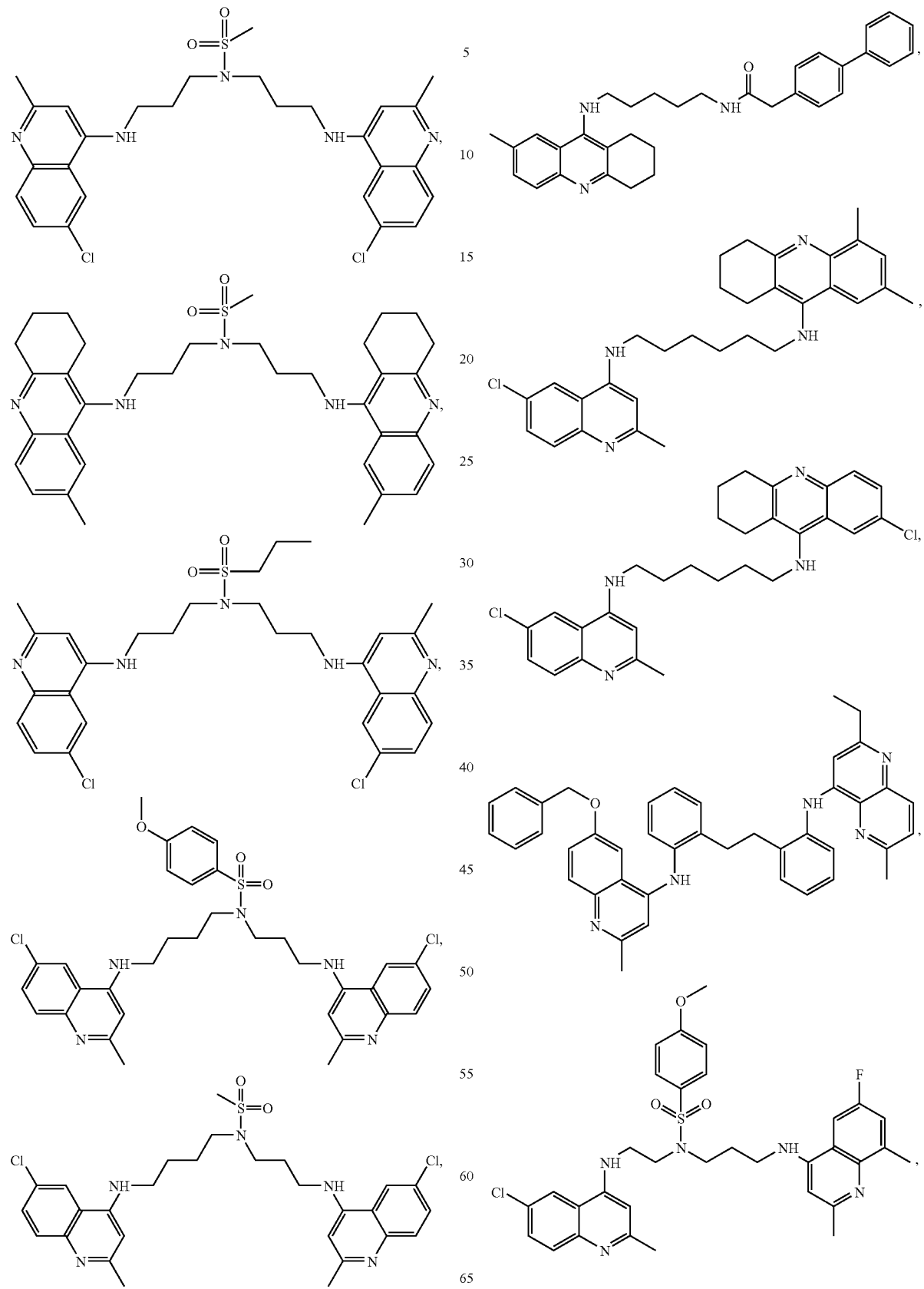

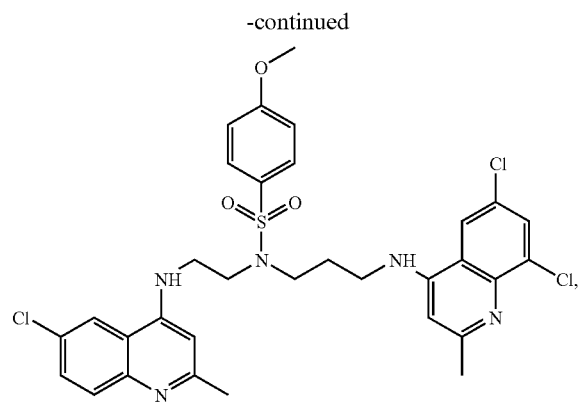
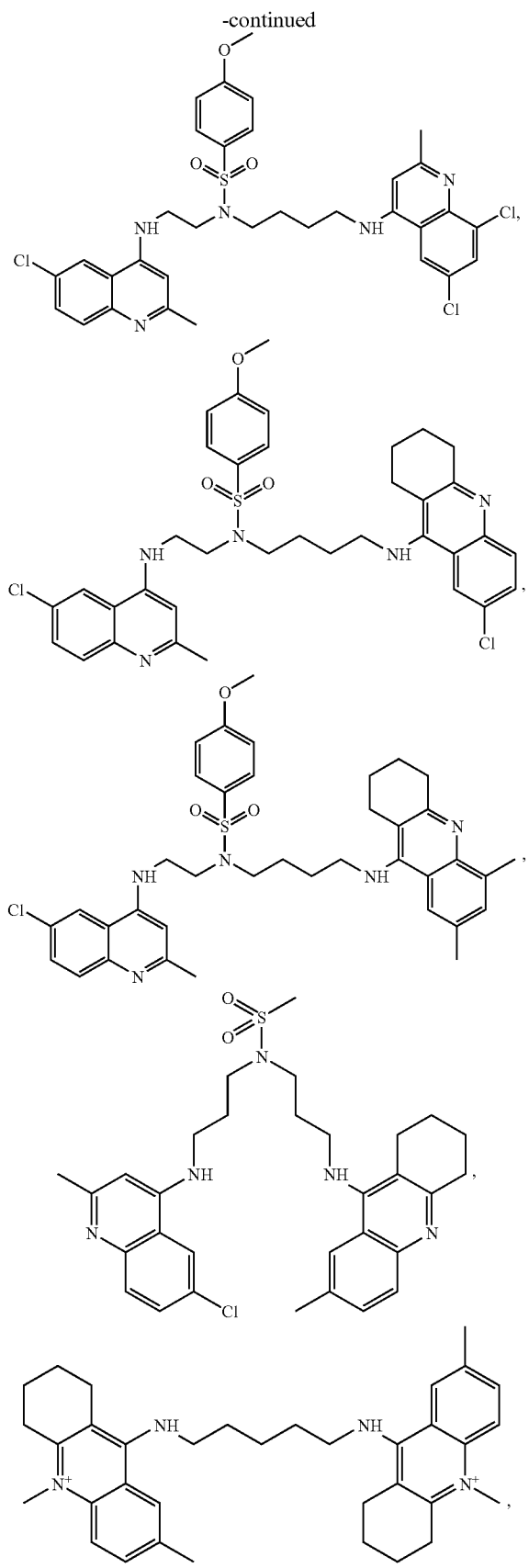

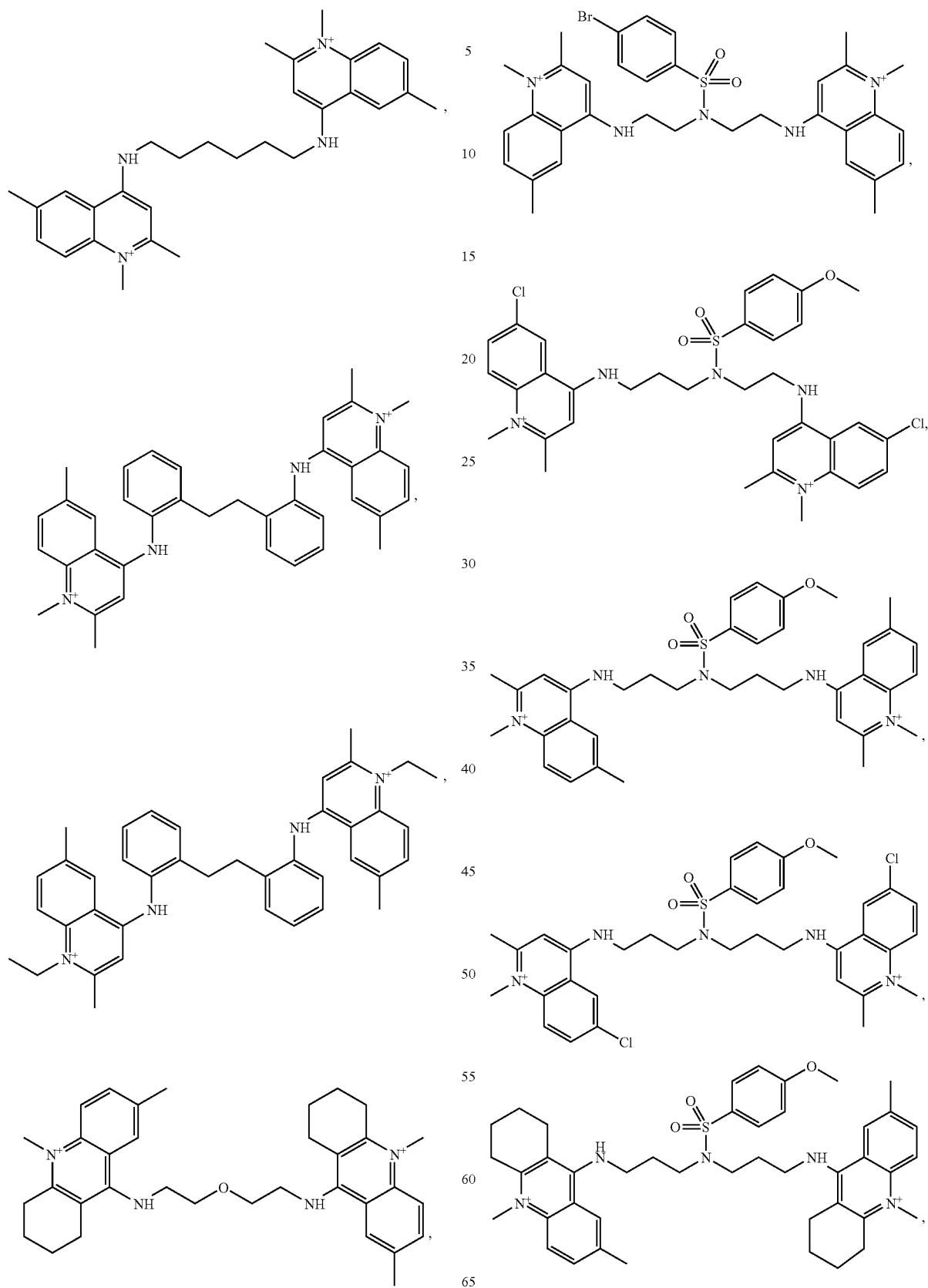

-continued
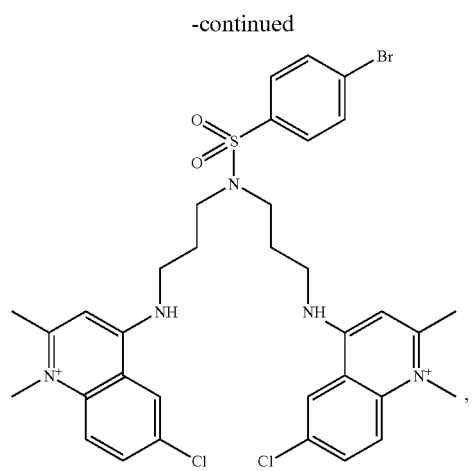
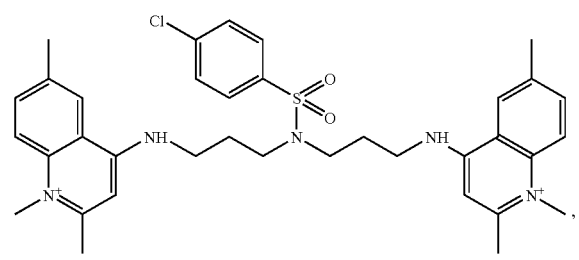
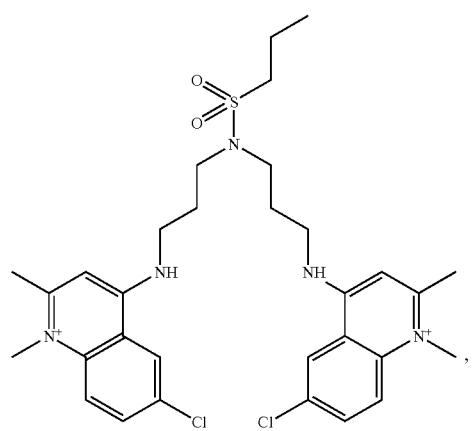
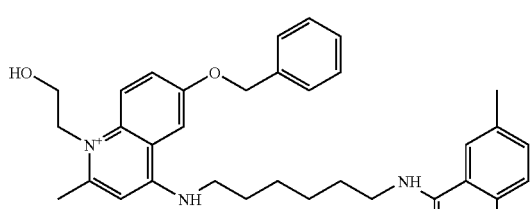
-continued
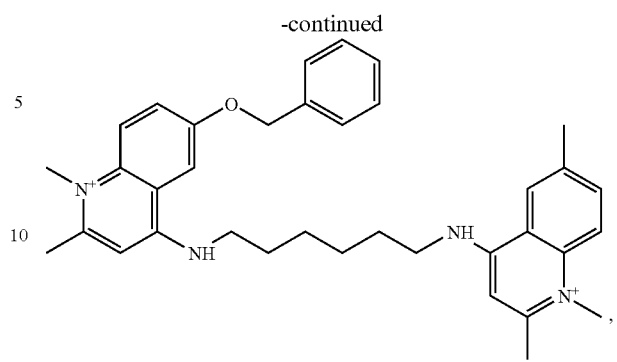
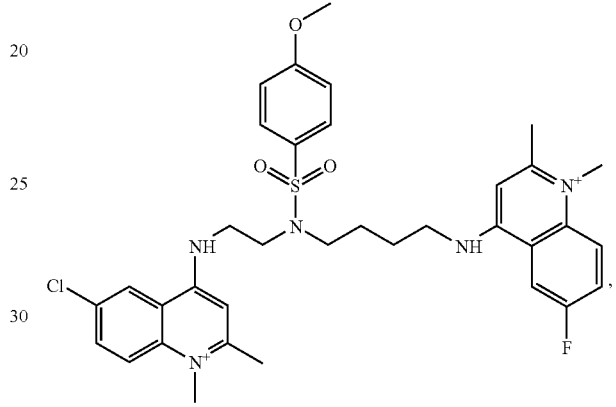
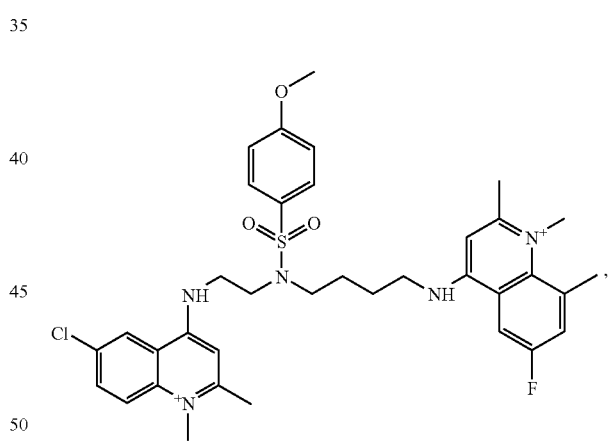
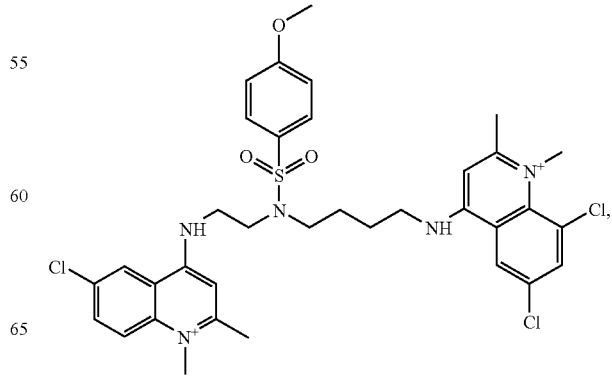

121
-continued
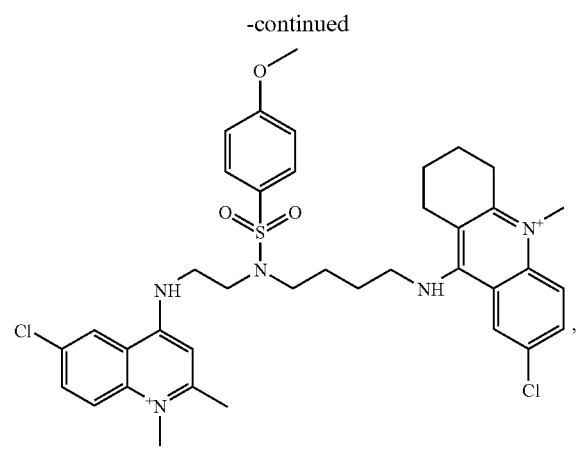
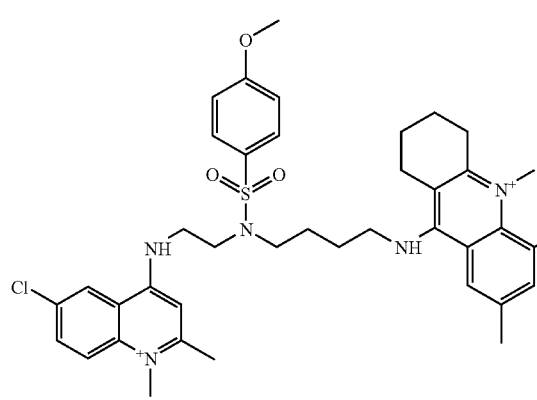
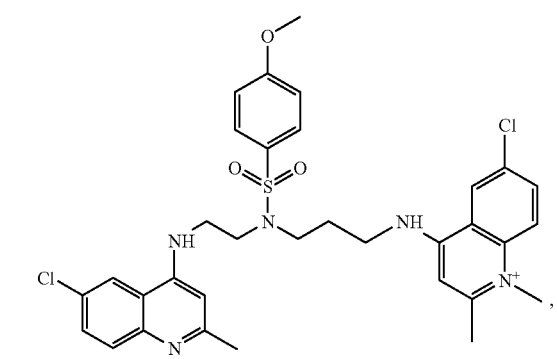
122
-continued
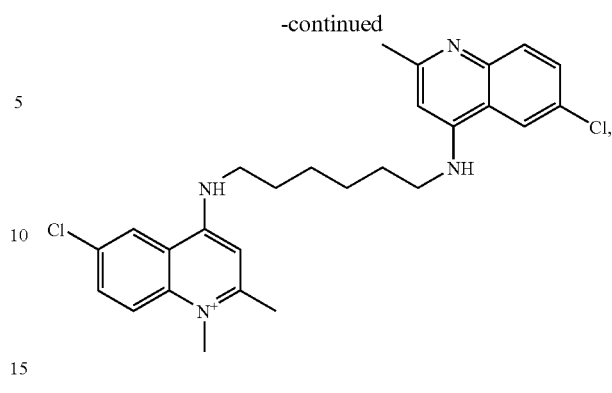
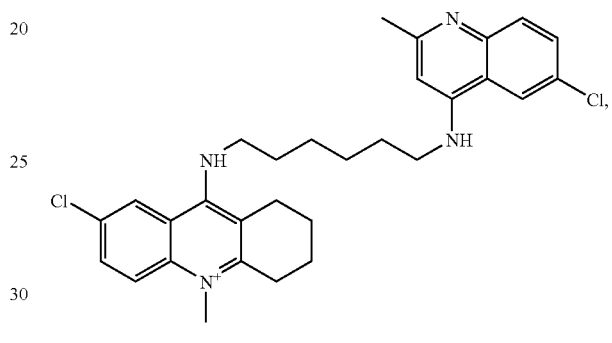
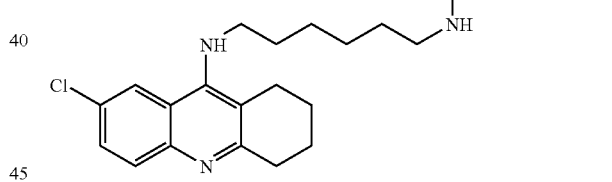
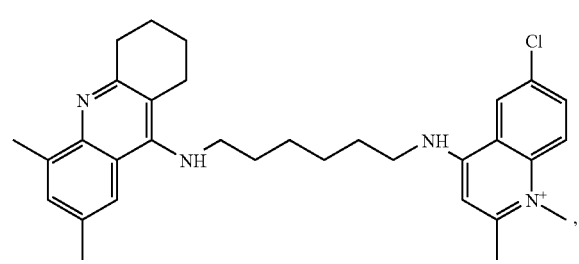
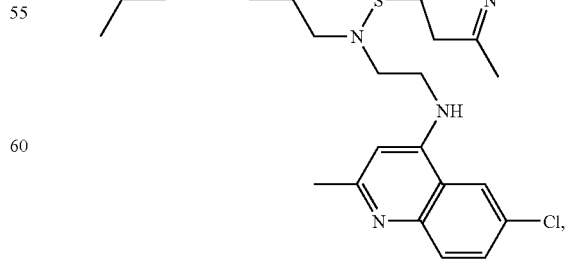

123
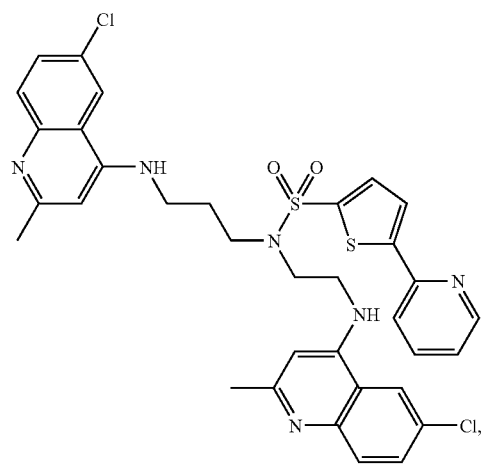
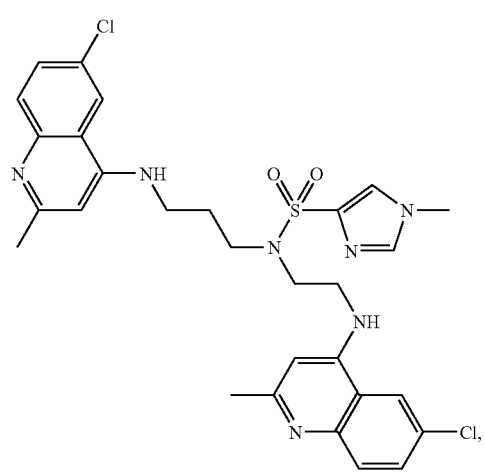
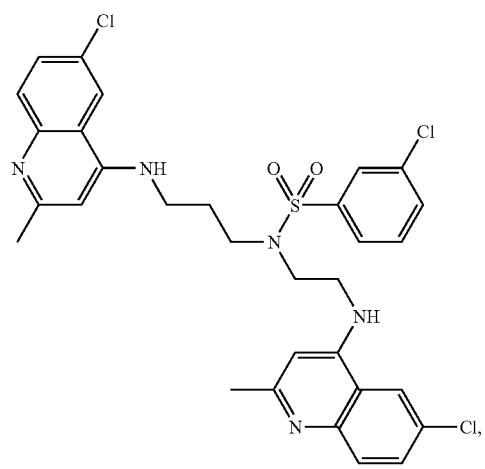
124
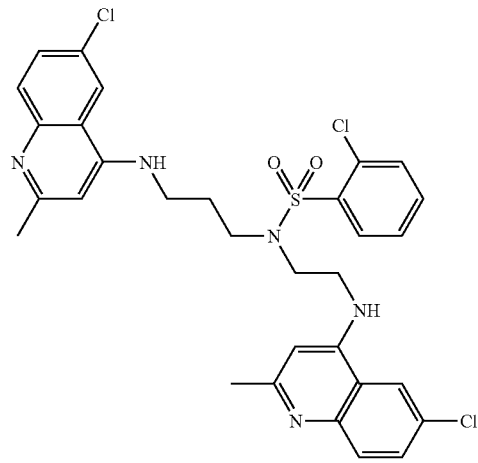
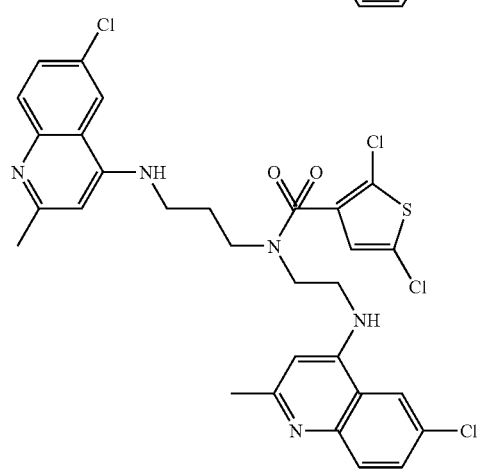
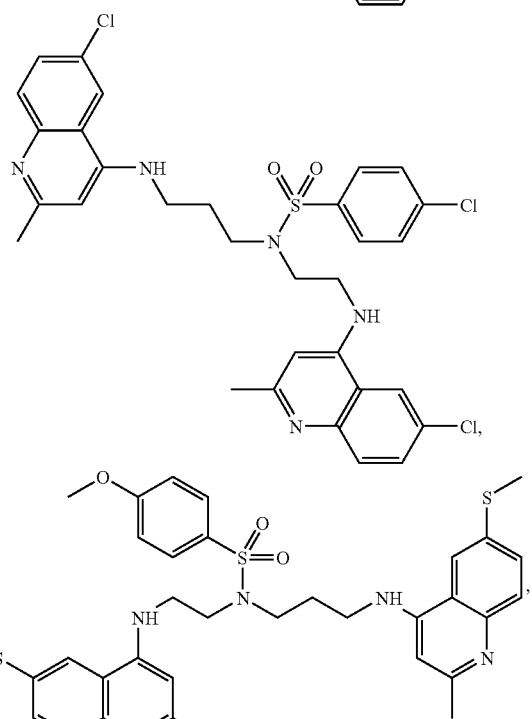

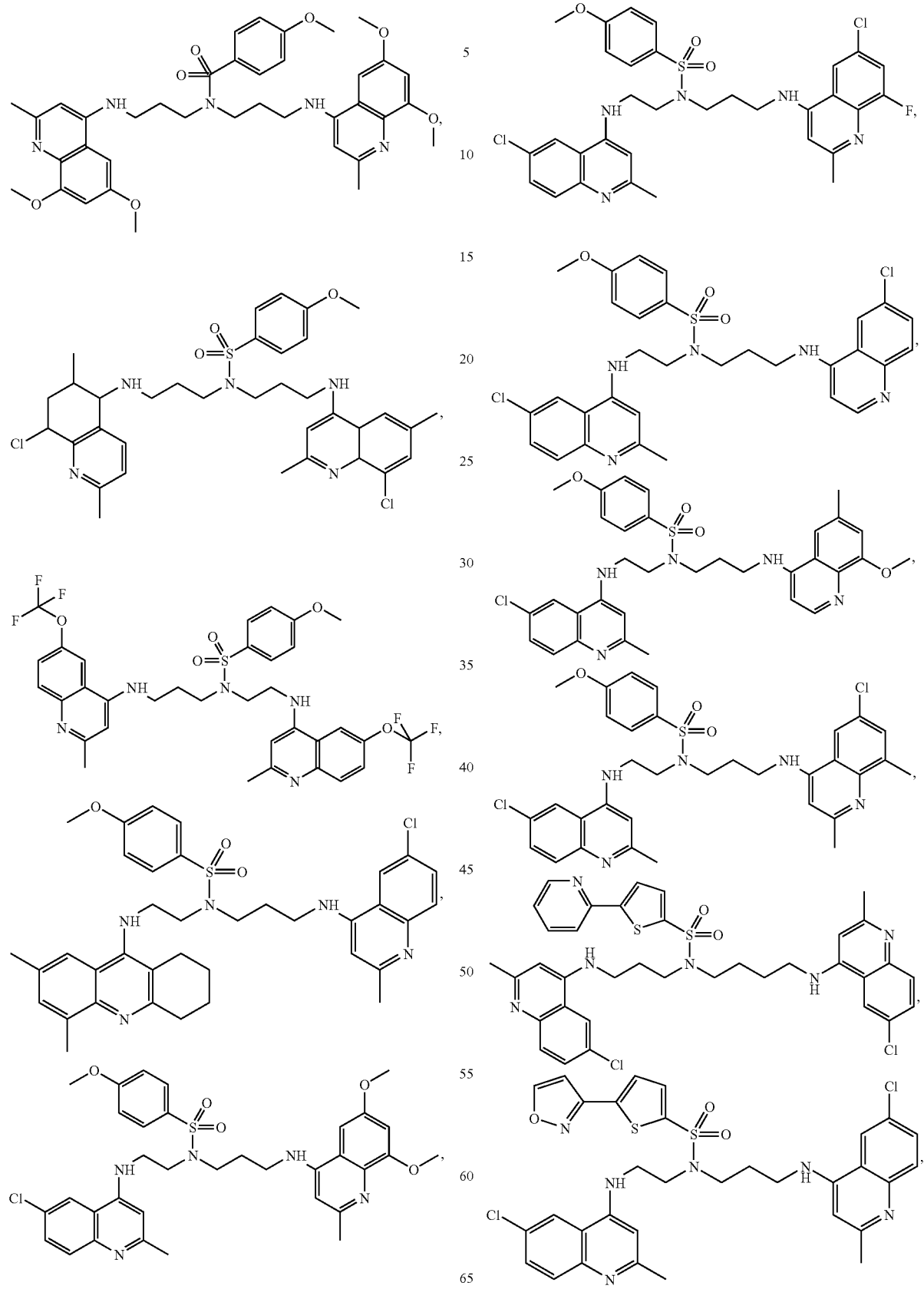

127
-continued
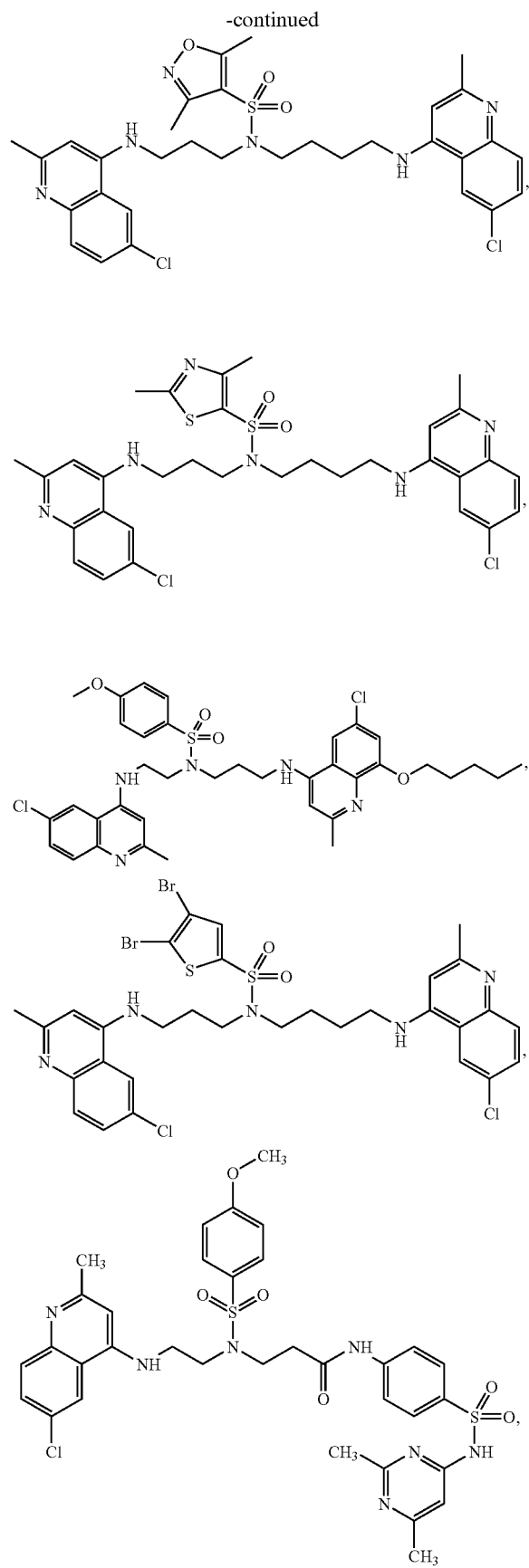
128
-continued
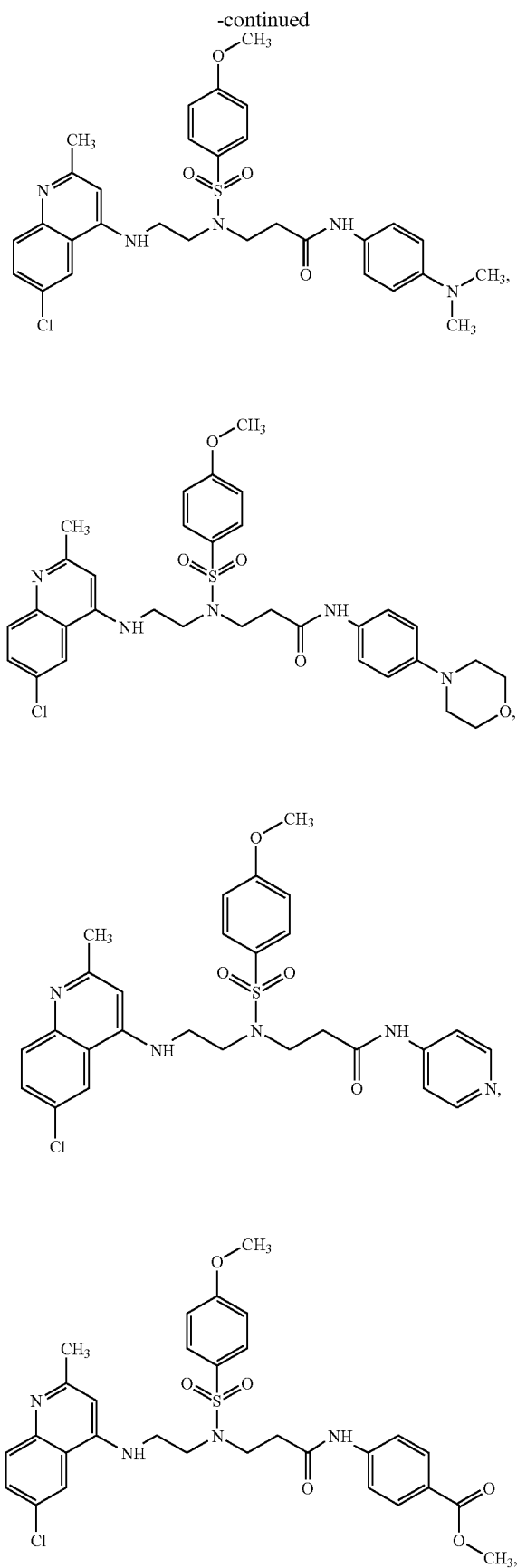

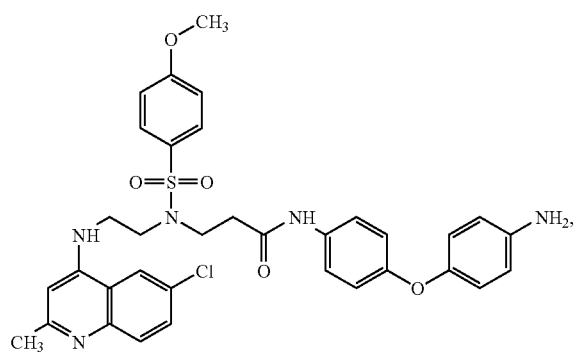
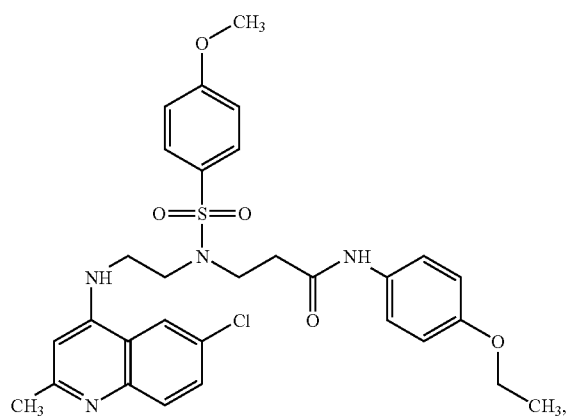
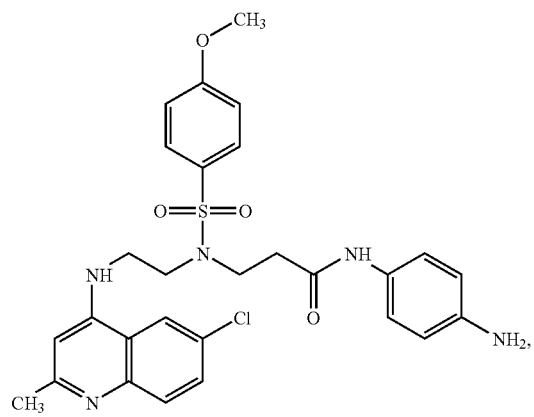
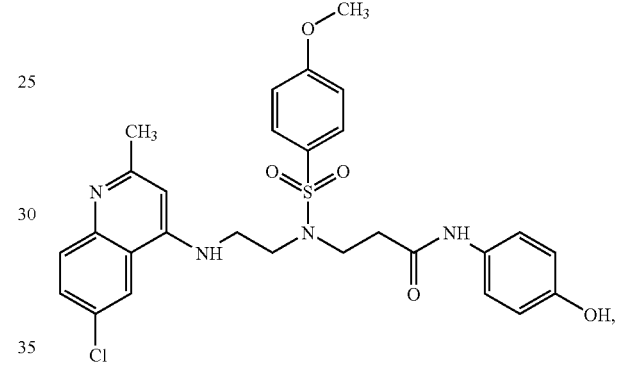
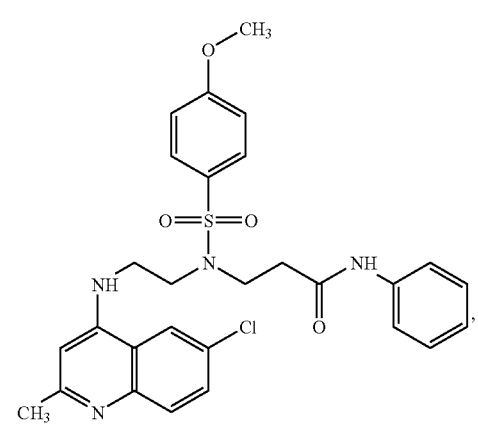
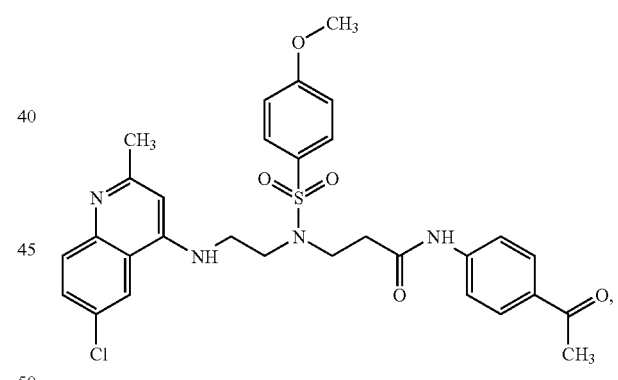
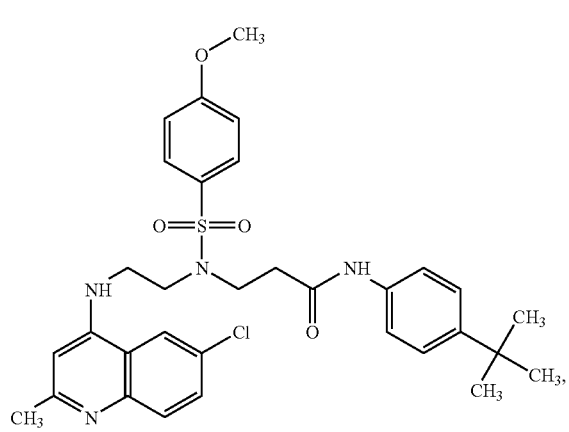
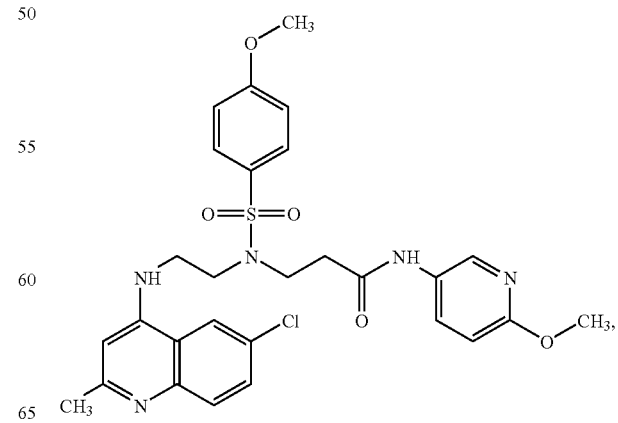

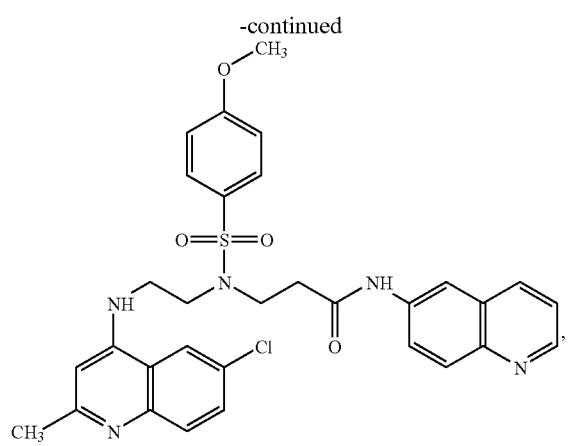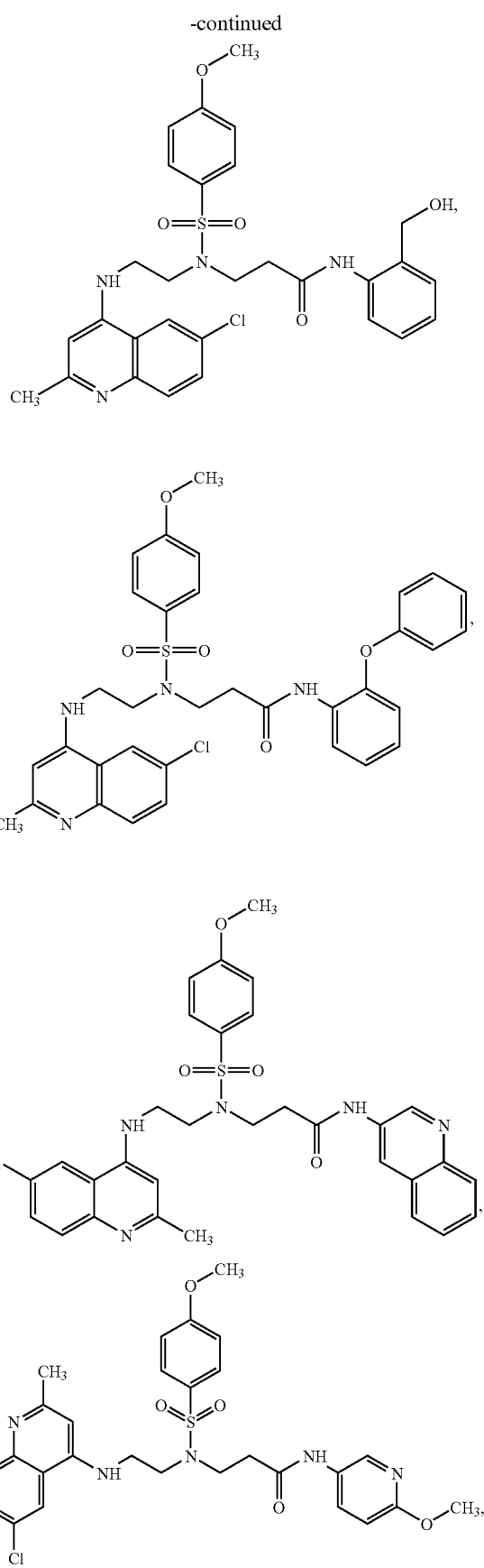

133
-continued
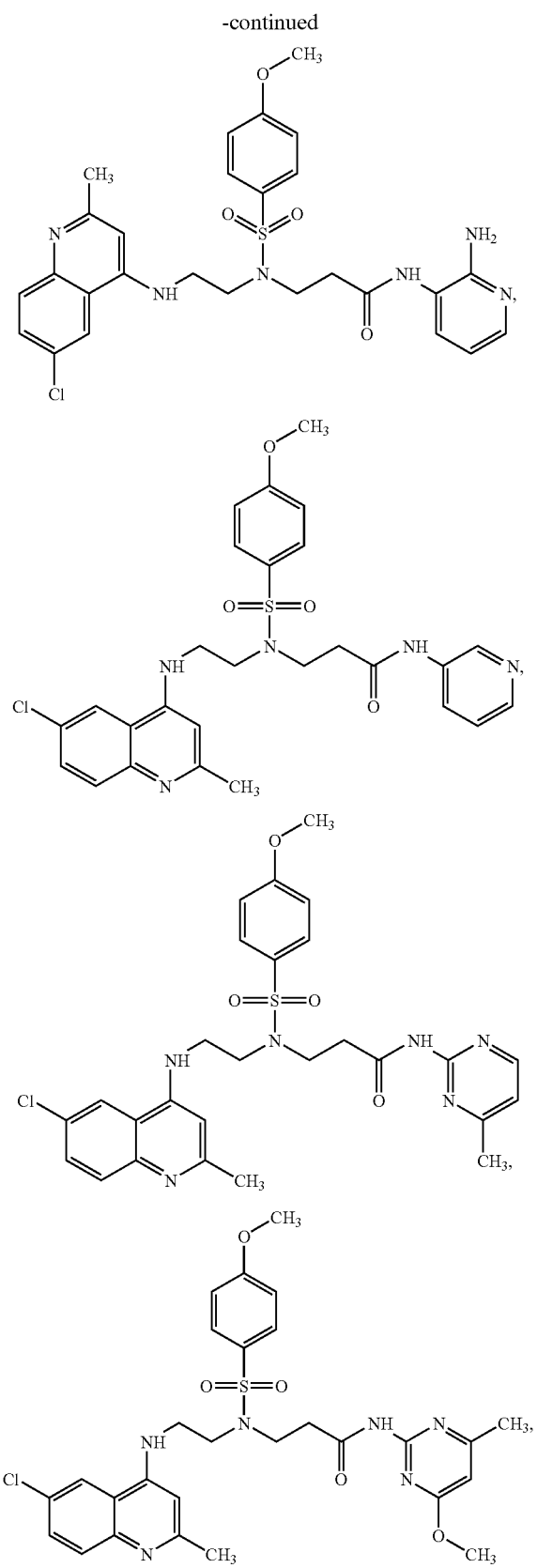
134
-continued
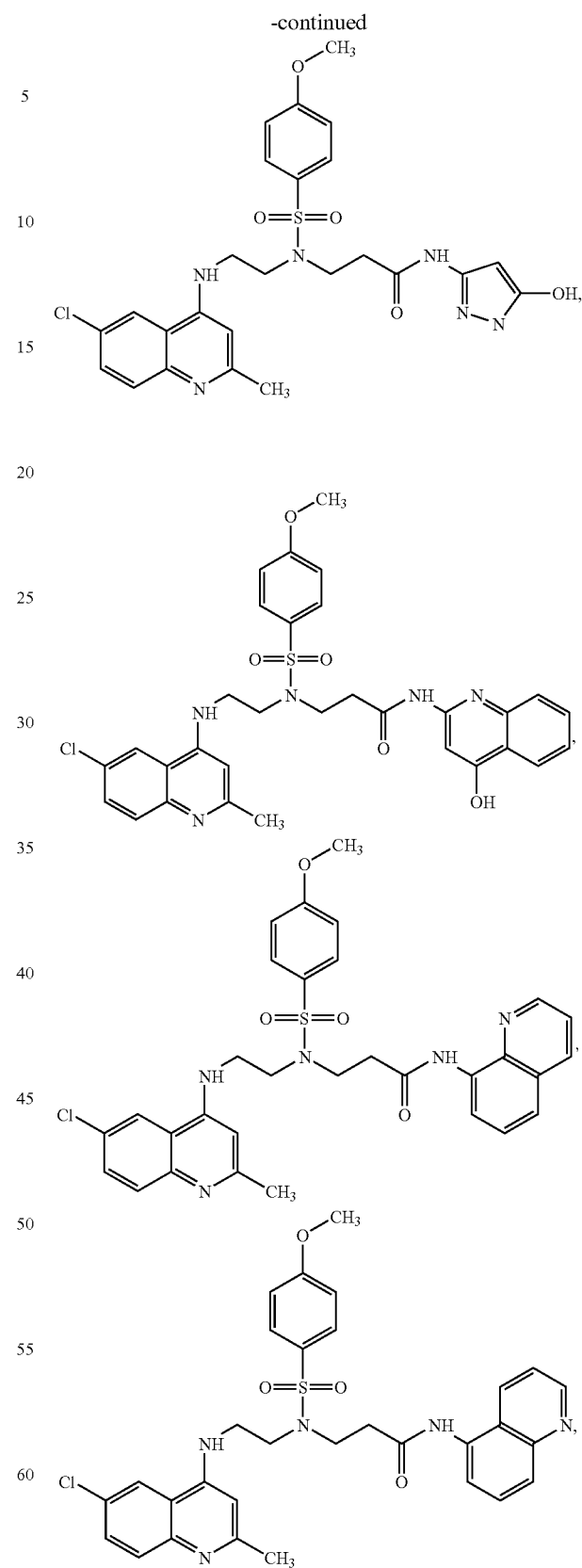

-continued
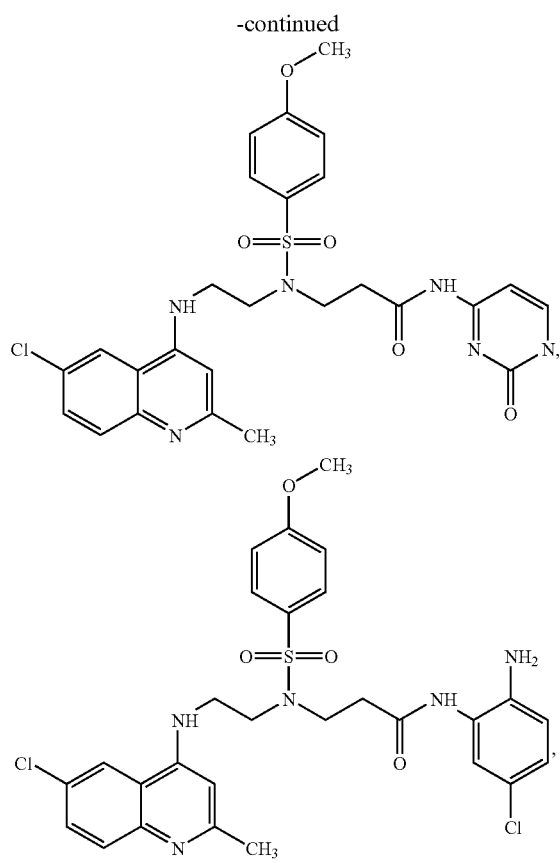
and
-continued
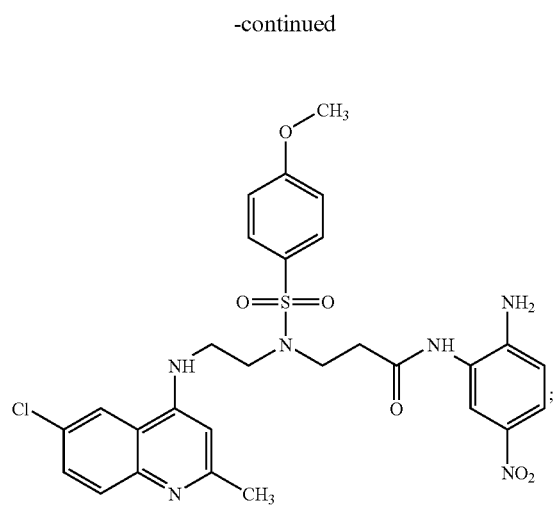
or a salt thereof.
46. A pharmaceutical composition comprising a compound of claim 45 and a pharmaceutically acceptable carrier.
* * * * *